United States Patent [19]

Suzuki et al.

[11] Patent Number: 5,674,182

[45] Date of Patent: Oct. 7, 1997

[54] ENDOSCOPE SYSTEM INCLUDING ENDOSCOPE AND PROTECTION COVER

[75] Inventors: Akira Suzuki, Yamanashi Pref.; Hisao Yabe; Yoshihiro Iida, both of Hachioji; Hideo Ito, Akishima; Yoshio Tashiro, Hino; Minoru Yamazaki, Hachioji; Osamu Tamada, Hachioji; Hiroshi Ishii, Hachioji; Jin Kira, Tokyo; Takeshi Yokoi, Hino, all of Japan

[73] Assignee: Olympus Optical Co., Ltd., Tokyo, Japan

[21] Appl. No.: 361,678

[22] Filed: Dec. 22, 1994

Related U.S. Application Data

[63] Continuation-in-part of Ser. No. 38,092, Mar. 30, 1993, abandoned.

[30] Foreign Application Priority Data

| Feb. 26, 1993 | [JP] | Japan | 5-7455 |
| Feb. 26, 1993 | [JP] | Japan | 5-7456 |
| Mar. 1, 1993 | [JP] | Japan | 5-7890 |
| Dec. 22, 1993 | [JP] | Japan | 5-325311 |
| Dec. 27, 1993 | [JP] | Japan | 5-331839 |
| Dec. 28, 1993 | [JP] | Japan | 5-337227 |

[51] Int. Cl.$^6$ .................................................. A61B 1/04
[52] U.S. Cl. .......................... 600/129; 600/121; 600/123
[58] Field of Search .................................. 600/121, 122, 600/123, 124, 125, 127, 128, 129, 139, 140, 142, 203, 206, 144

[56] References Cited

U.S. PATENT DOCUMENTS

| 3,035,691 | 5/1962 | Rasmussen et al. . |
| 3,633,758 | 1/1972 | Morse . |
| 4,108,211 | 8/1978 | Tanaka . |
| 4,216,767 | 8/1980 | Aoshiro . |
| 4,288,882 | 9/1981 | Takeuchi . |

(List continued on next page.)

FOREIGN PATENT DOCUMENTS

| 0341719A1 | 11/1989 | European Pat. Off. . |
| 0349479A1 | 1/1990 | European Pat. Off. . |
| 2805298A1 | 8/1978 | Germany . |
| 3-76128B2 | 10/1989 | Japan . |
| 3264037A | 11/1991 | Japan . |
| 4325138 | 11/1992 | Japan . |

*Primary Examiner*—Beverly M. Flanagan
*Attorney, Agent, or Firm*—Watson Cole Stevens Davis, P.L.L.C.

[57] ABSTRACT

An endoscope system including an endoscope having an insertion section which extends from a proximal end to a distal end and is inserted into a cavity under inspection and an operation section connected to the proximal end of the insertion section, and a protection cover including an insertion section inserting channel which extends from a proximal end to a distal end and into which said insertion section of the endoscope is insertable and a conduit channel which extends from the proximal end to the distal end, the improvement being characterized in that a distal end portion of the insertion section has a non-circular cross section such as a semicircular or oval cross section and a proximal end portion of the insertion section has a substantially circular cross section. A distal end member of the insertion section inserting channel has an accommodating portion which is a corresponding non-circular cross section.

13 Claims, 43 Drawing Sheets

U.S. PATENT DOCUMENTS

| | | |
|---|---|---|
| 4,366,901 | 1/1983 | Short . |
| 4,404,963 | 9/1983 | Kohri . |
| 4,646,722 | 3/1987 | Silverstein et al. . |
| 4,715,360 | 12/1987 | Akui et al. . |
| 4,721,097 | 1/1988 | D'Amelio . |
| 4,741,326 | 5/1988 | Sidall et al. . |
| 4,779,727 | 10/1988 | Taterka et al. . |
| 4,825,850 | 5/1989 | Opie et al. . |
| 4,858,001 | 8/1989 | Milbank et al. . |
| 4,869,238 | 9/1989 | Opie et al. . |
| 4,877,033 | 10/1989 | Seitz, Jr. ................... 126/4 X |
| 4,878,485 | 11/1989 | Adair ................... 126/6 |
| 4,907,395 | 3/1990 | Opie et al. . |
| 4,947,827 | 8/1990 | Opie et al. . |
| 4,991,564 | 2/1991 | Takahashi et al. . |
| 4,991,565 | 2/1991 | Takahashi et al. . |
| 5,025,778 | 6/1991 | Silverstein et al. . |
| 5,042,112 | 8/1991 | Dunklee . |
| 5,050,585 | 9/1991 | Takahashi . |
| 5,105,942 | 4/1992 | van Veen et al. . |
| 5,131,537 | 7/1992 | Gonzales . |
| 5,198,894 | 3/1993 | Hicks ................... 126/4 X |
| 5,201,908 | 4/1993 | Jones . |
| 5,217,001 | 6/1993 | Nakao et al. . |
| 5,237,984 | 8/1993 | Williams, III et al. ................... 126/4 |
| 5,257,617 | 11/1993 | Takahashi ................... 600/123 |
| 5,301,657 | 4/1994 | Lafferty et al. ................... 126/6 |
| 5,334,142 | 8/1994 | Paradis . |
| 5,363,843 | 11/1994 | Daneshvar . |
| 5,419,311 | 5/1995 | Yabe et al. . |

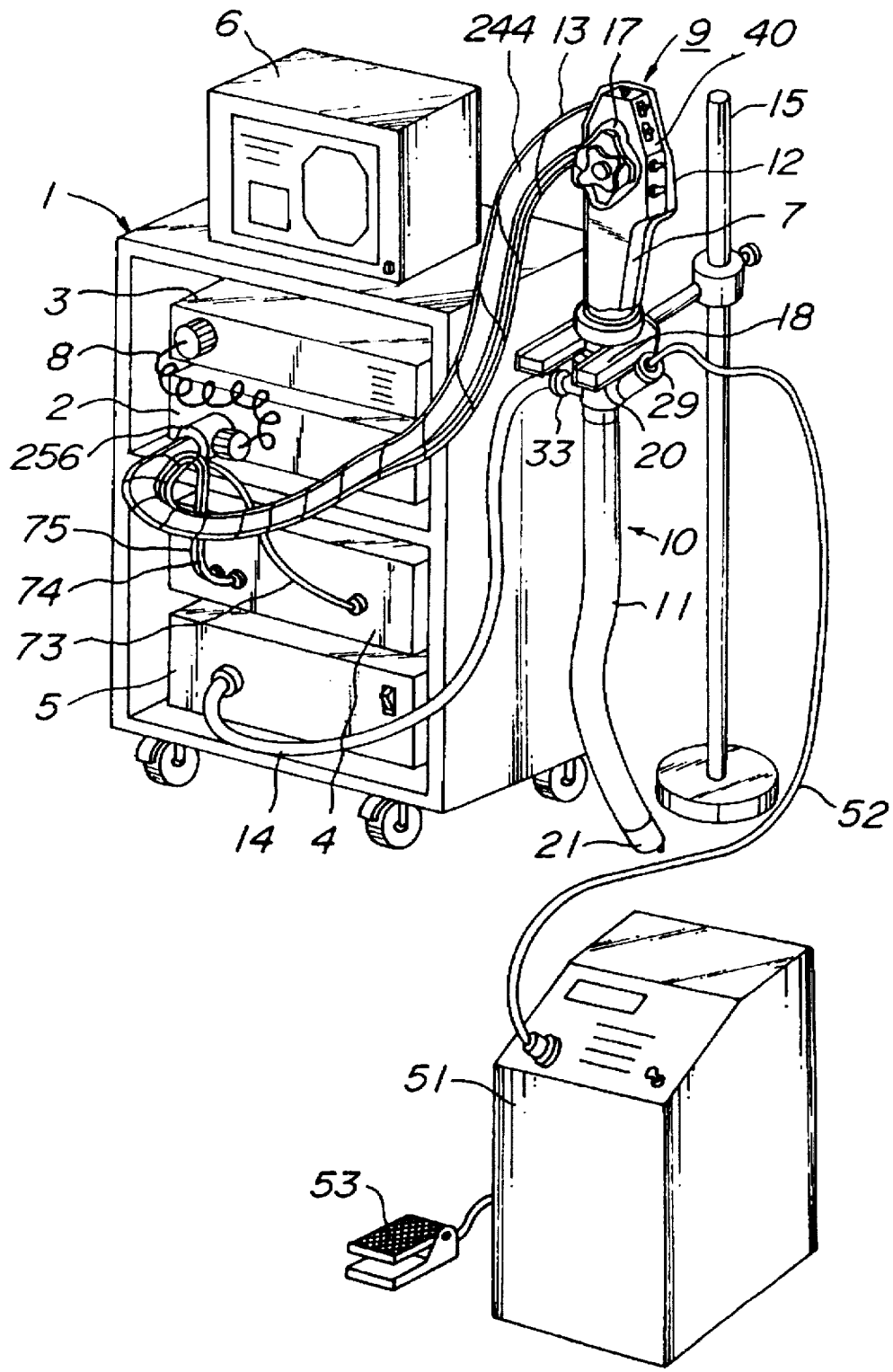
FIG_1

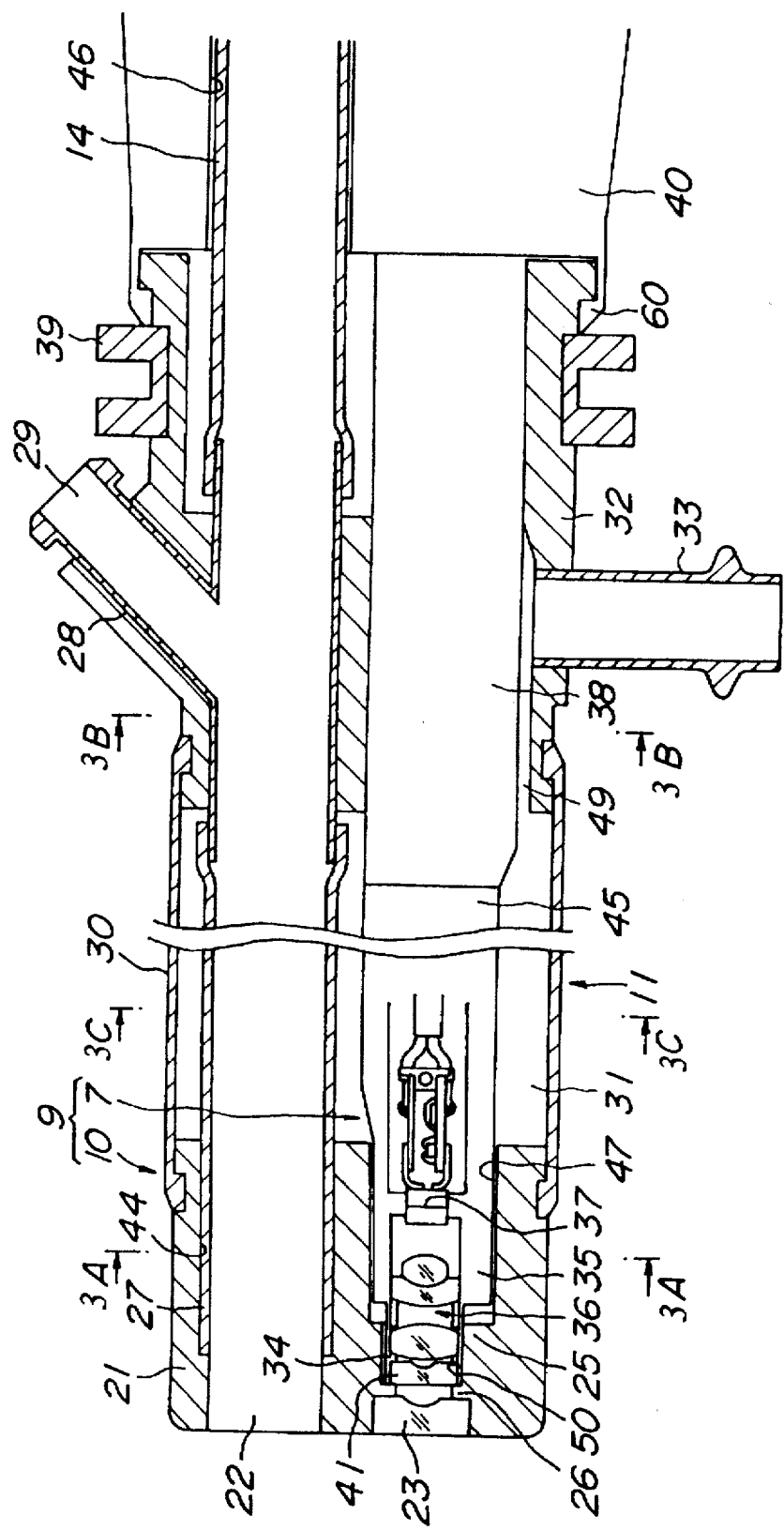

FIG_3A
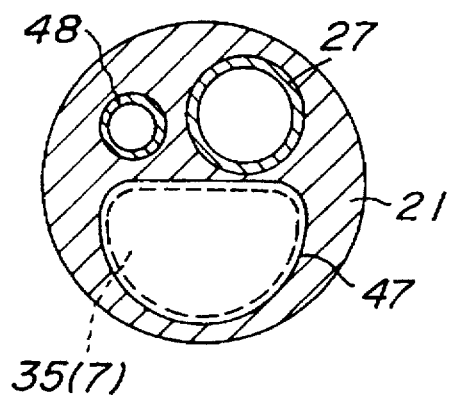
FIG_3B
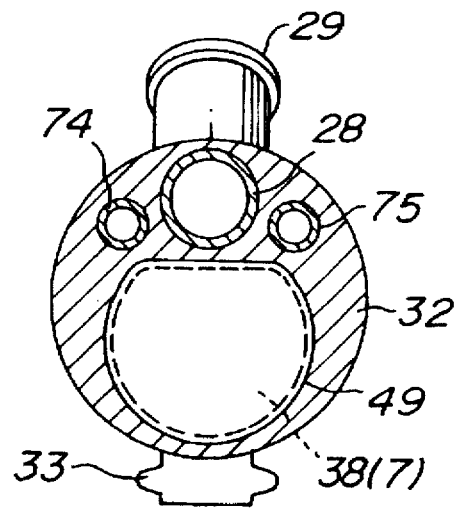
FIG_3C
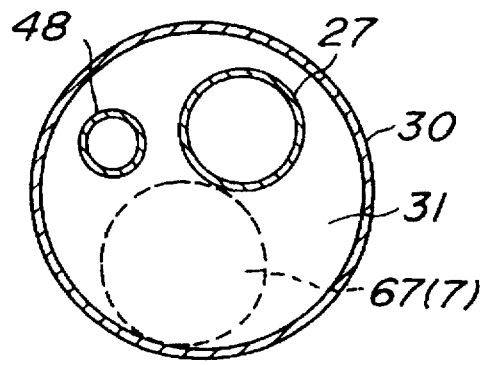

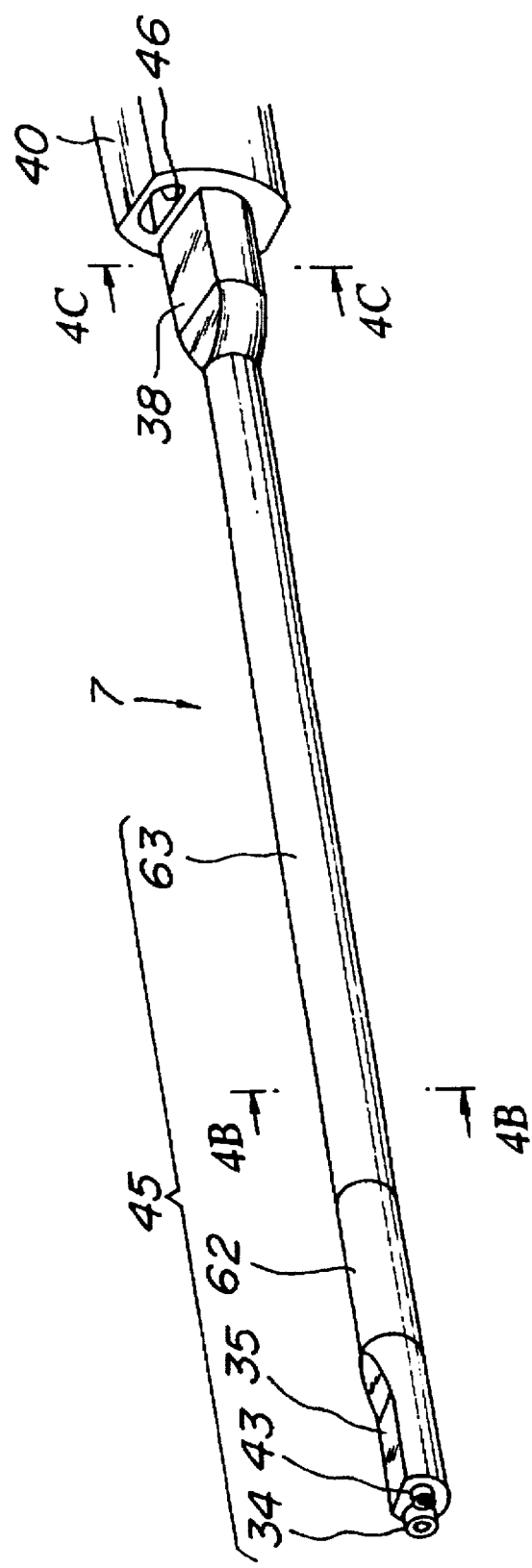

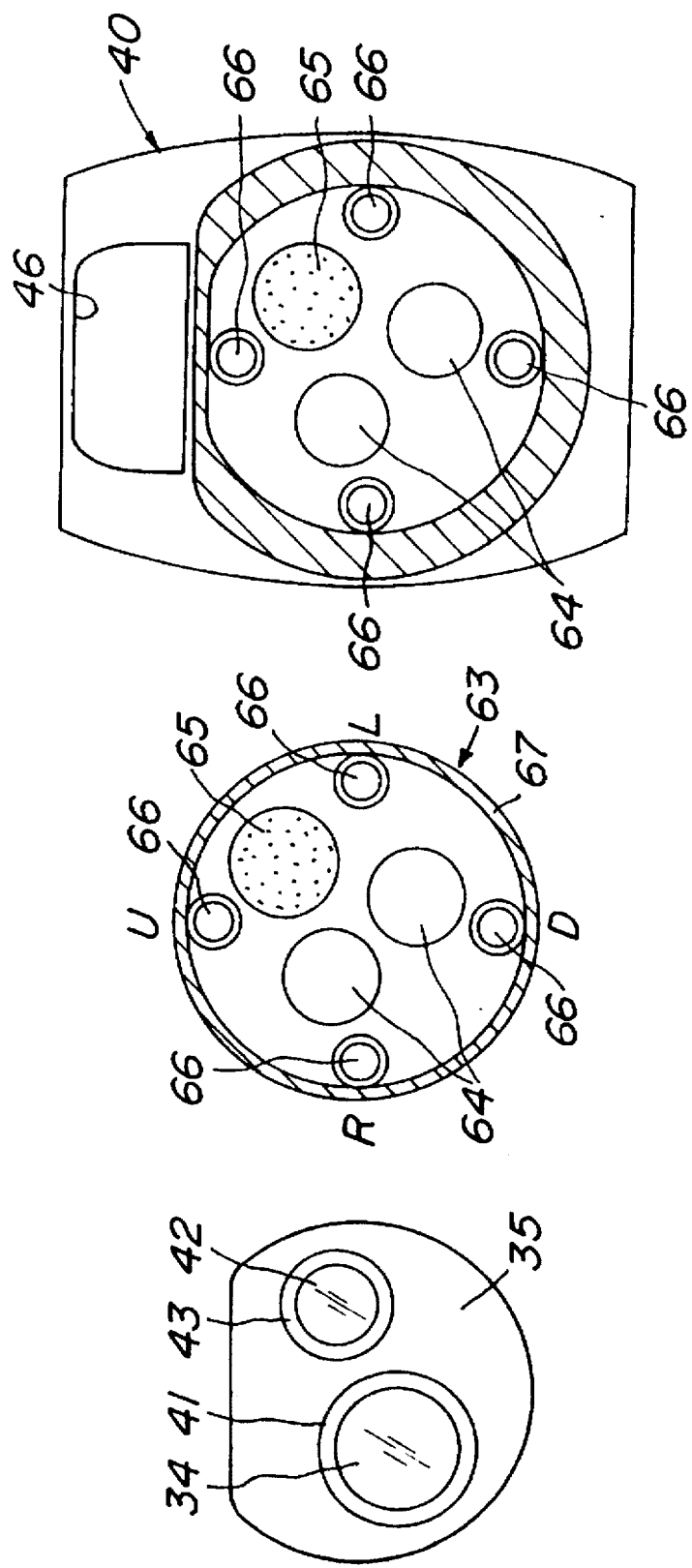
FIG._5C
FIG._5B
FIG._5A

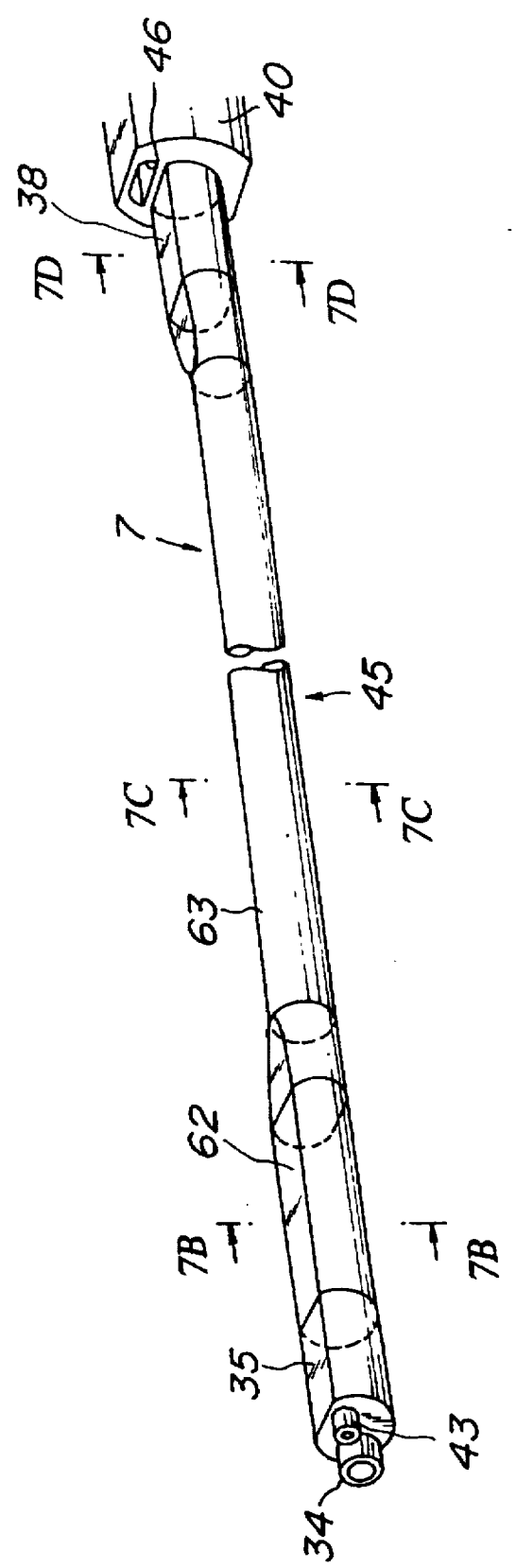

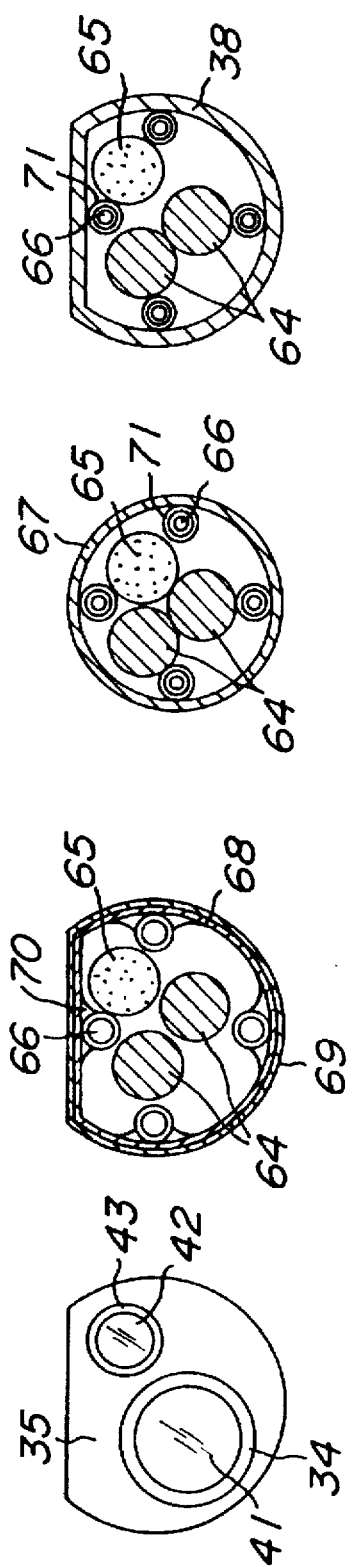

FIG_8
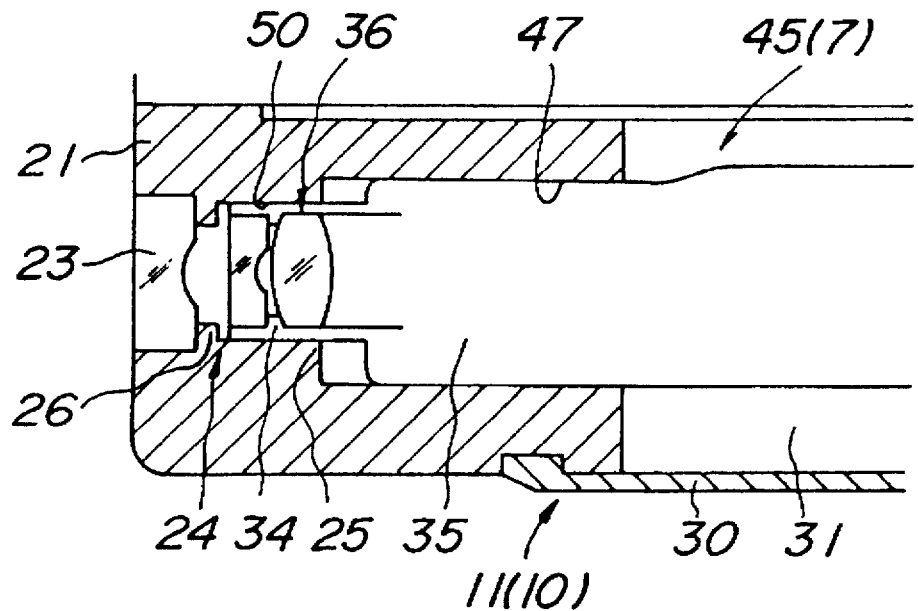
FIG_9
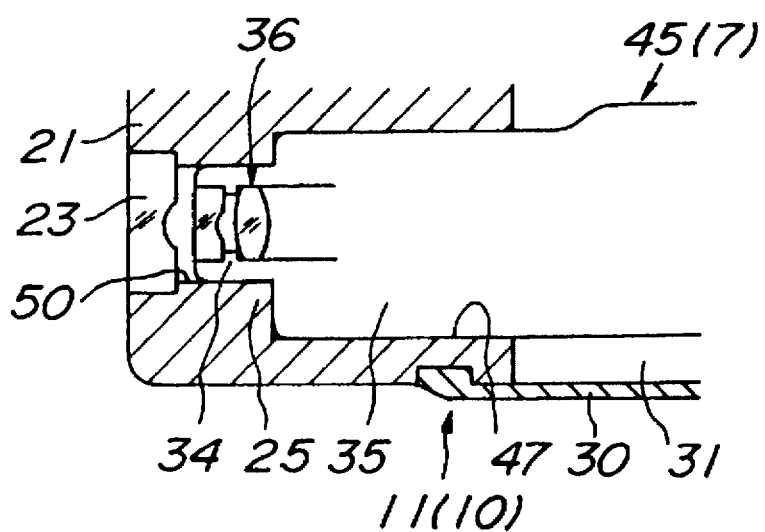

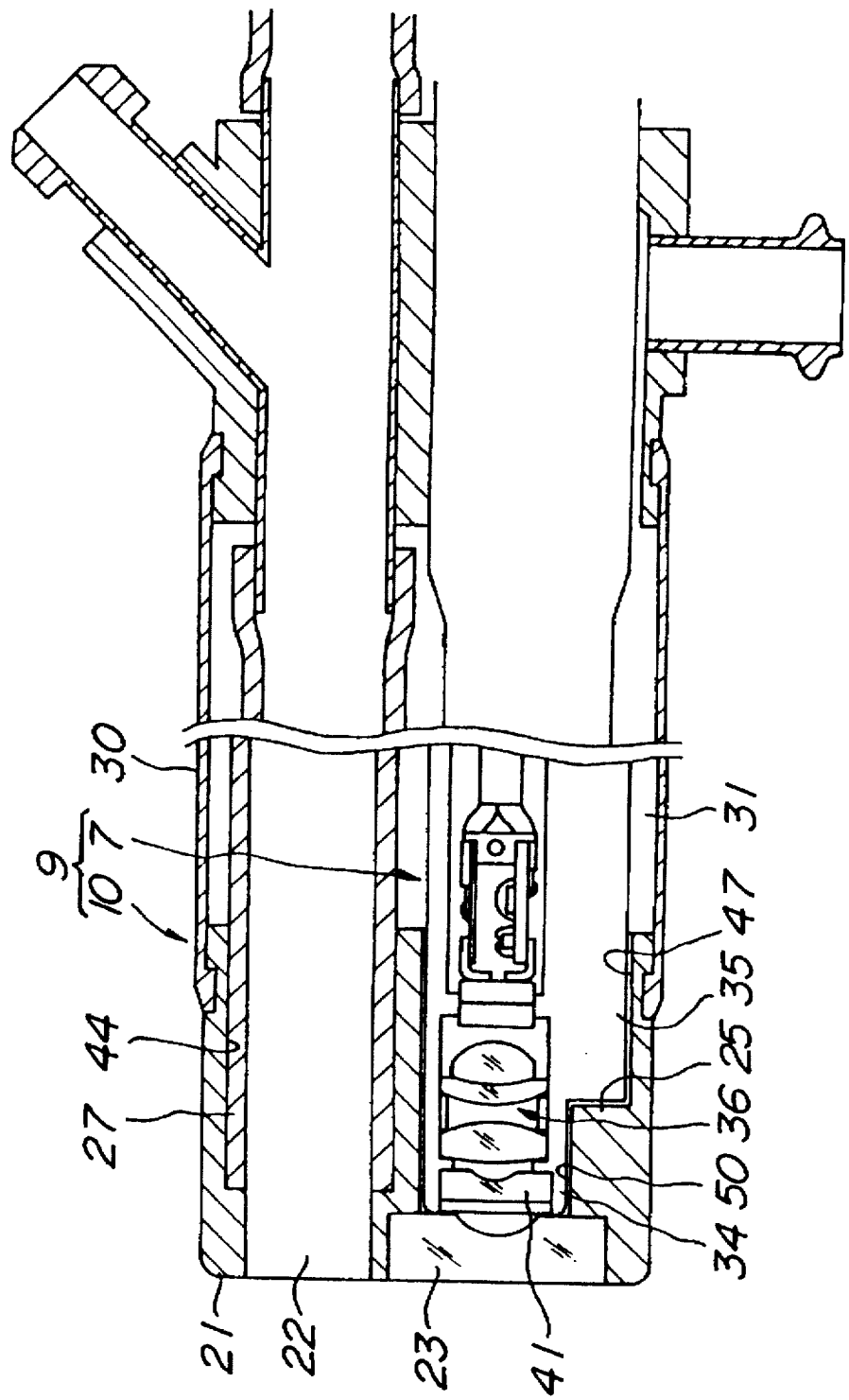

FIG_11
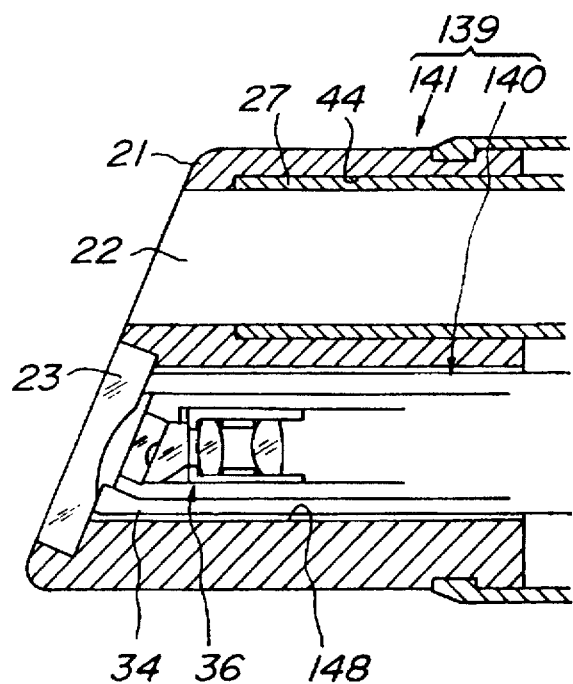
FIG_12
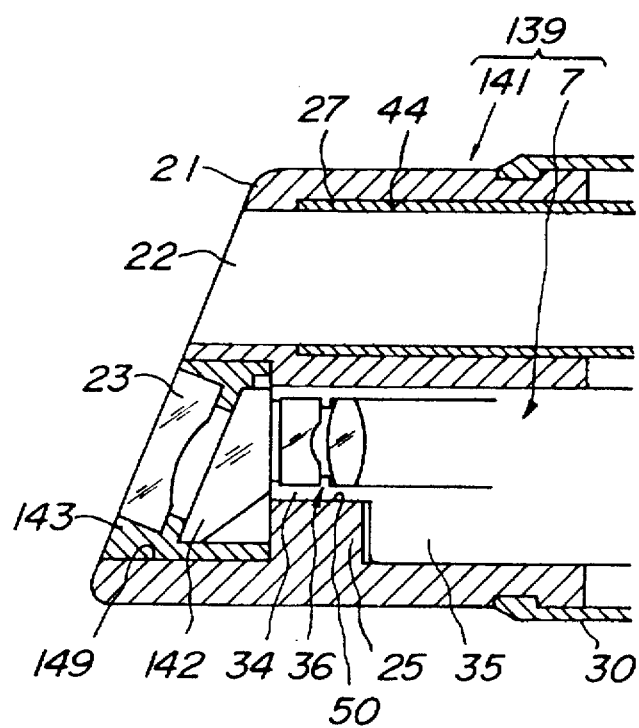

FIG_15
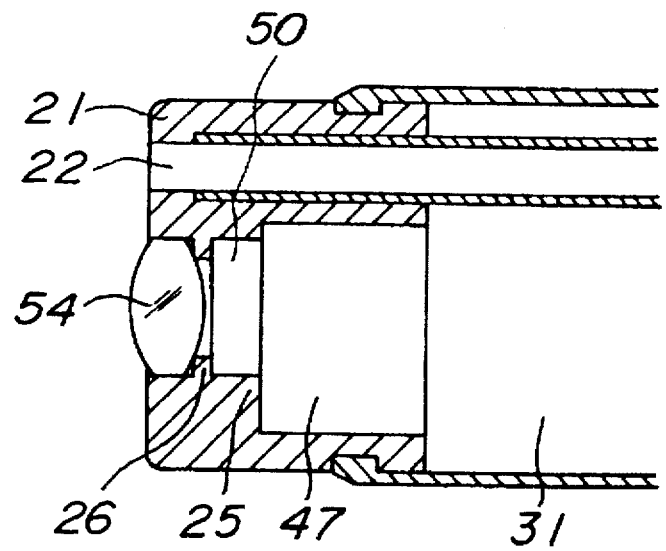
FIG_16
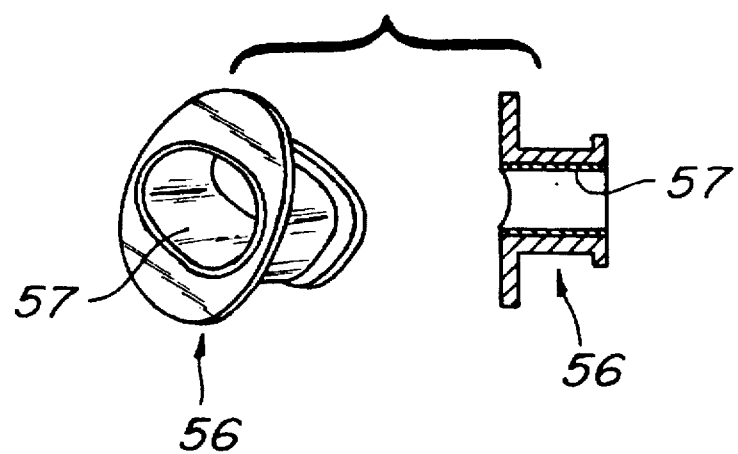

FIG_17
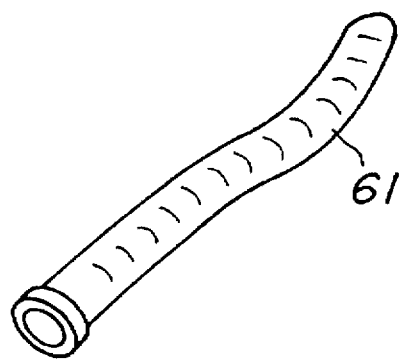
FIG_18
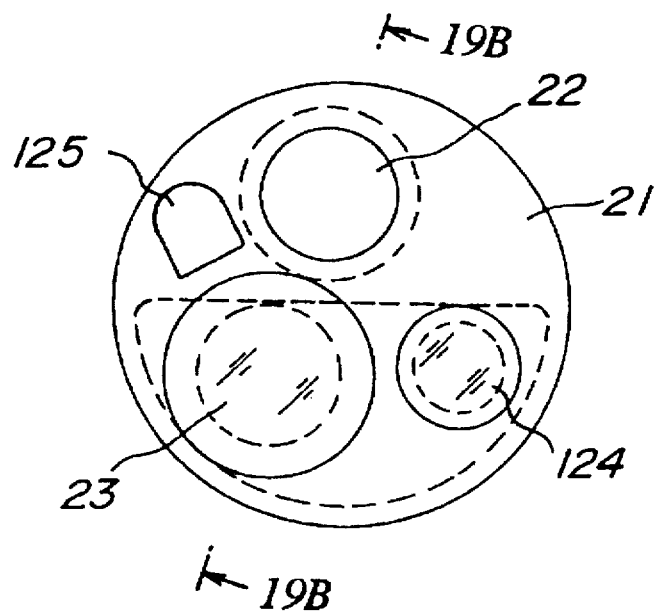

FIG_19A
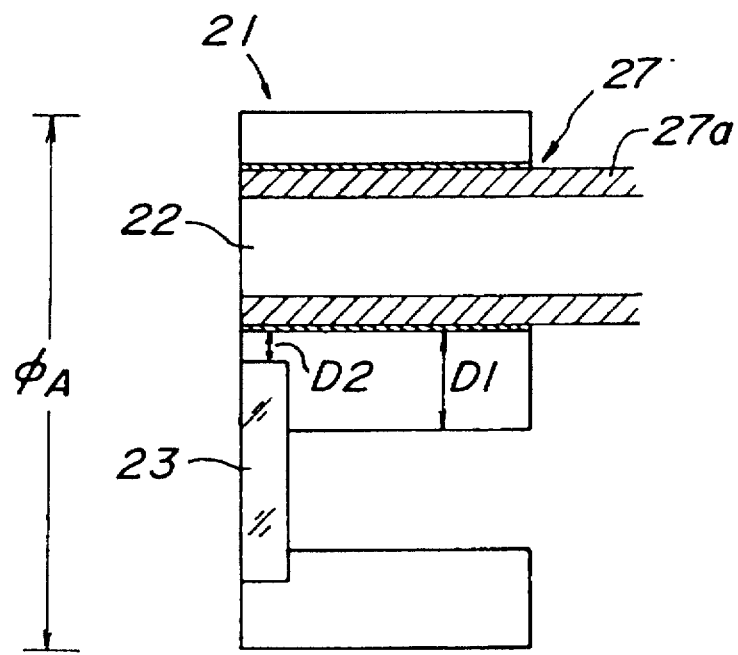
FIG_19B
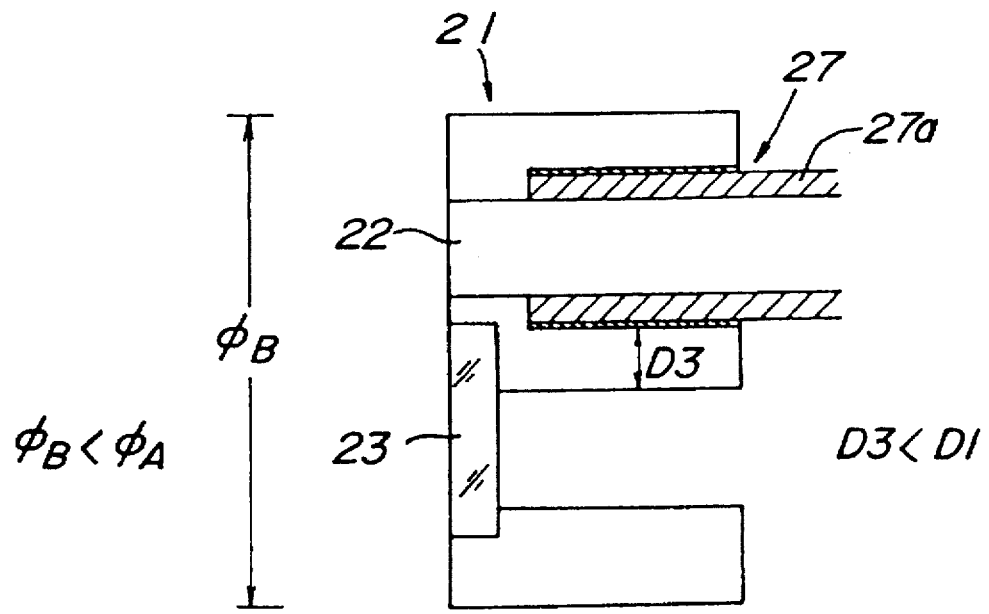
$\phi_B < \phi_A$
$D3 < D1$

FIG_20
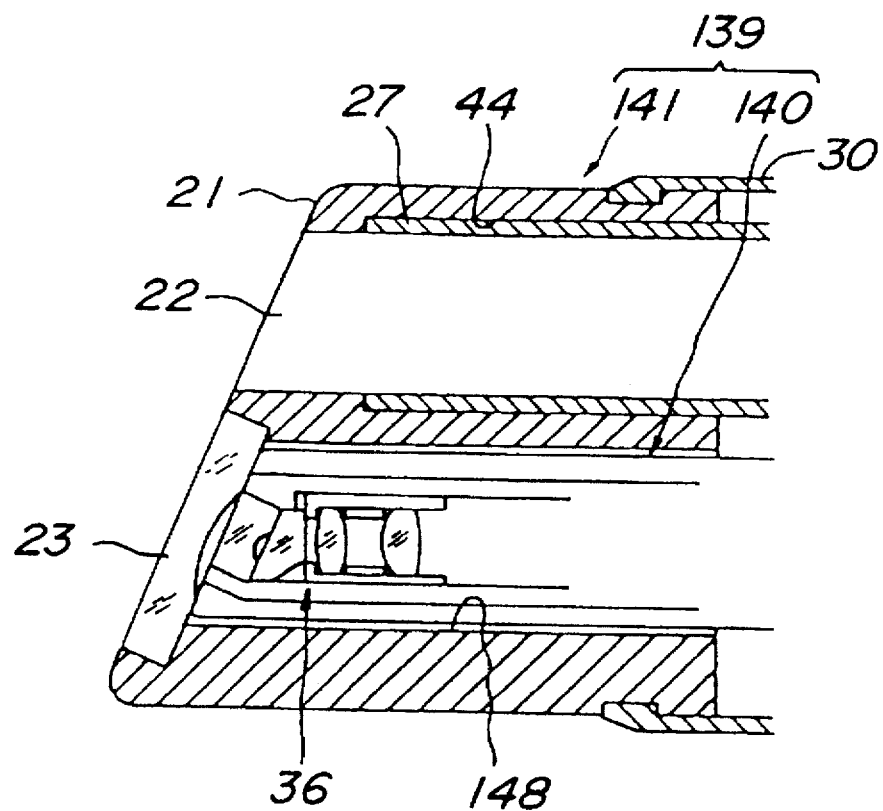
FIG_21
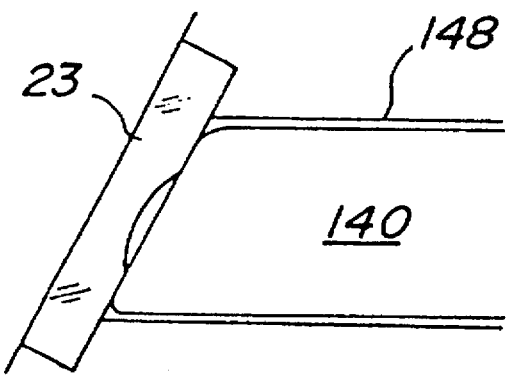

FIG_22
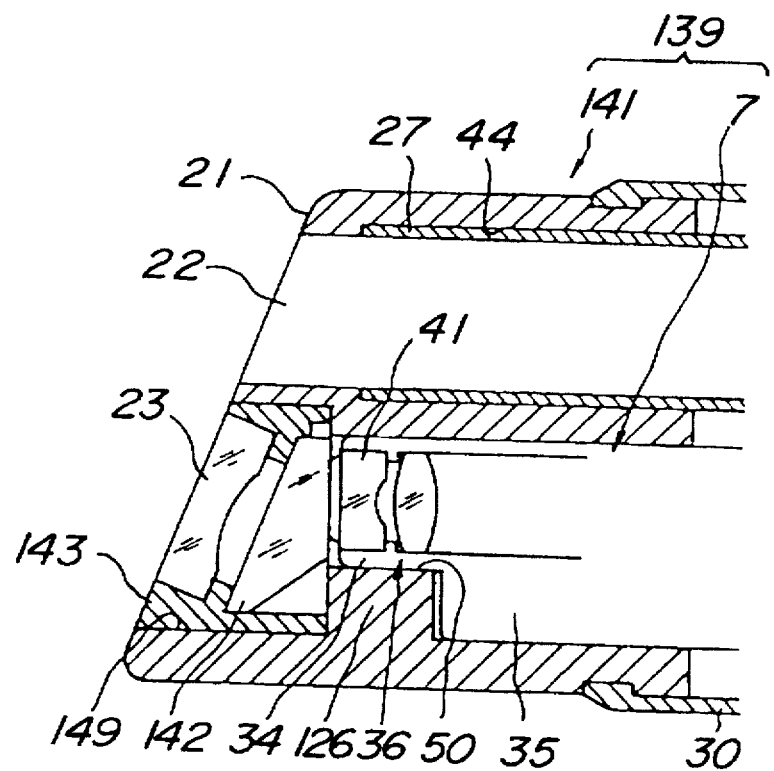
FIG_23
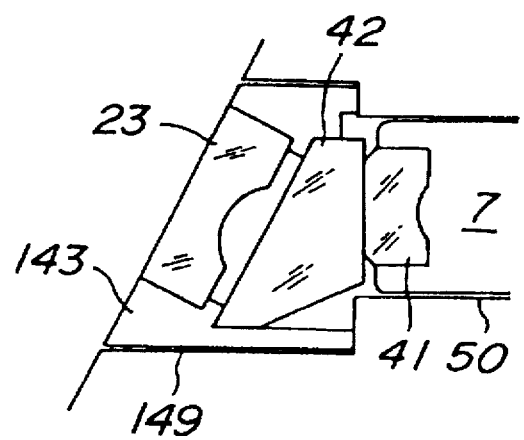

FIG_28

FIG_31
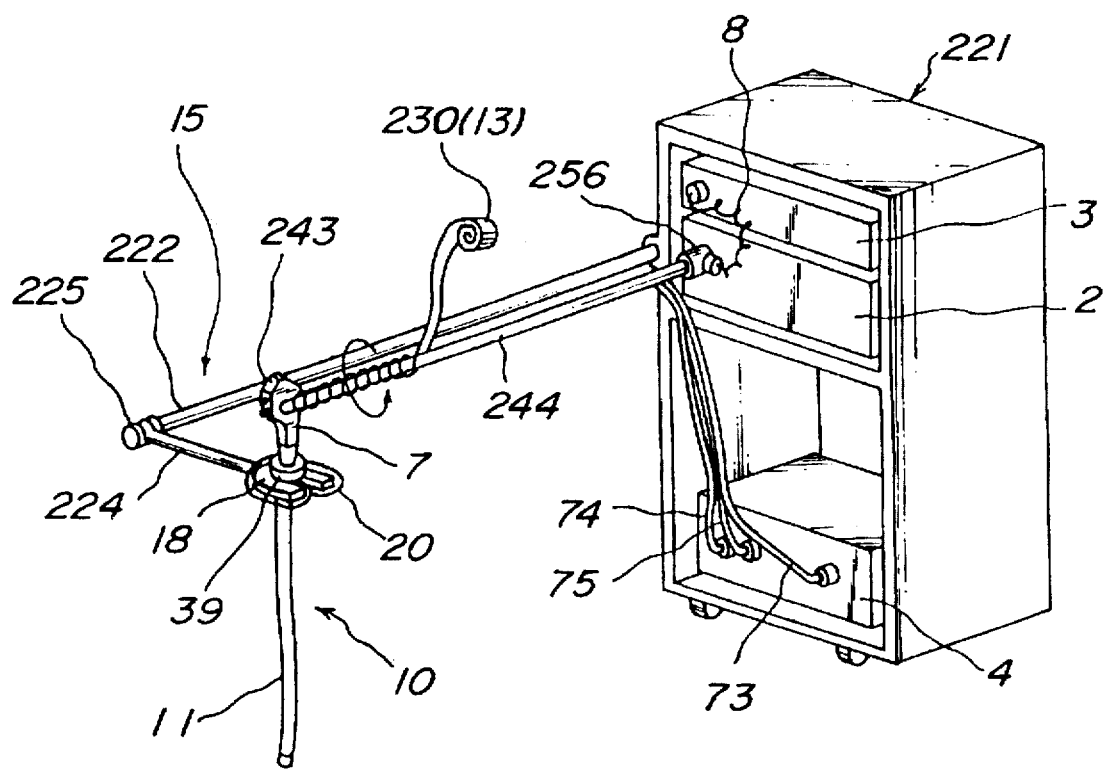

FIG_32
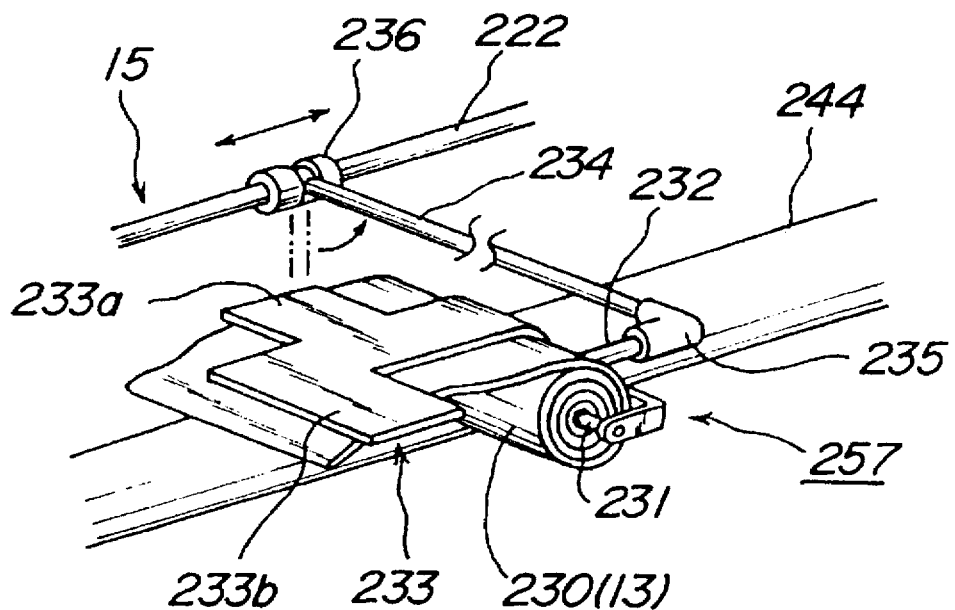
FIG_33
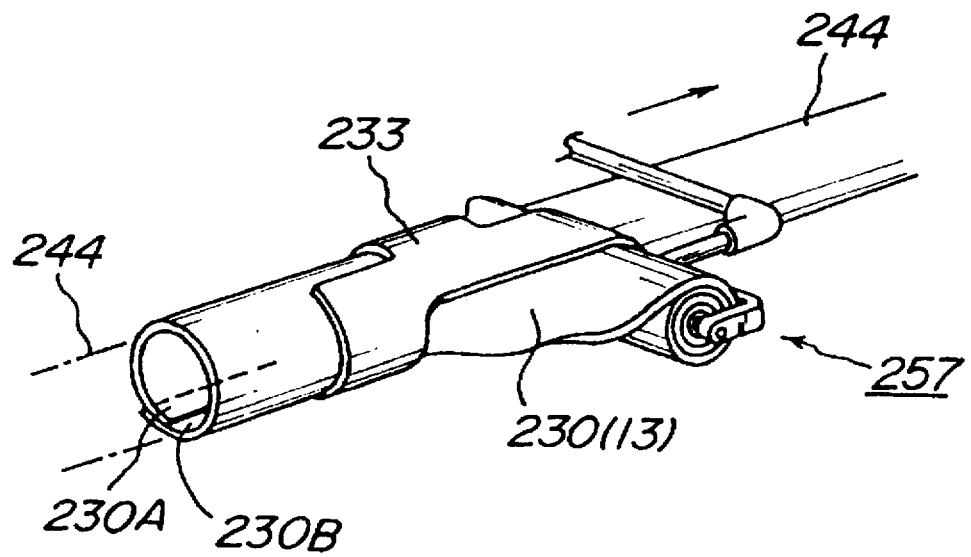

FIG_34
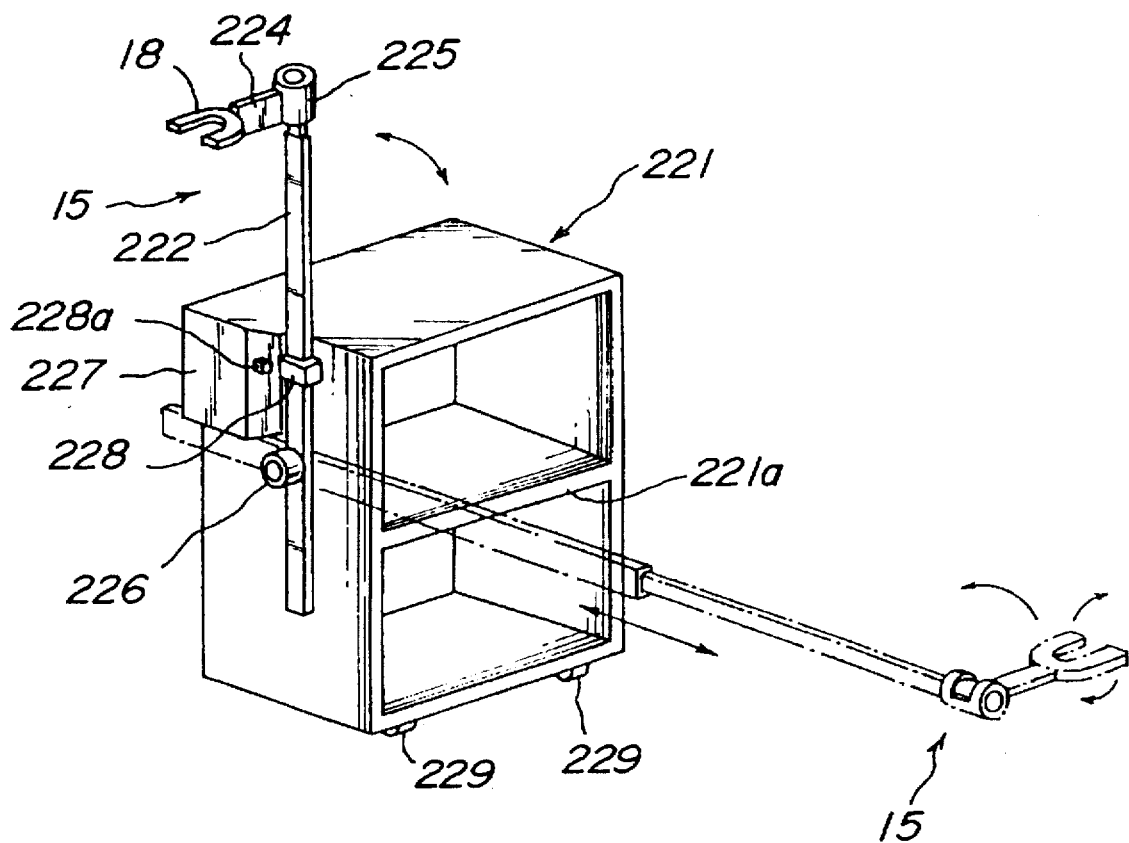
FIG_35
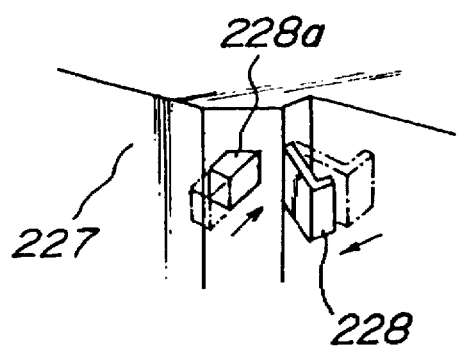

FIG_36
FIG_37
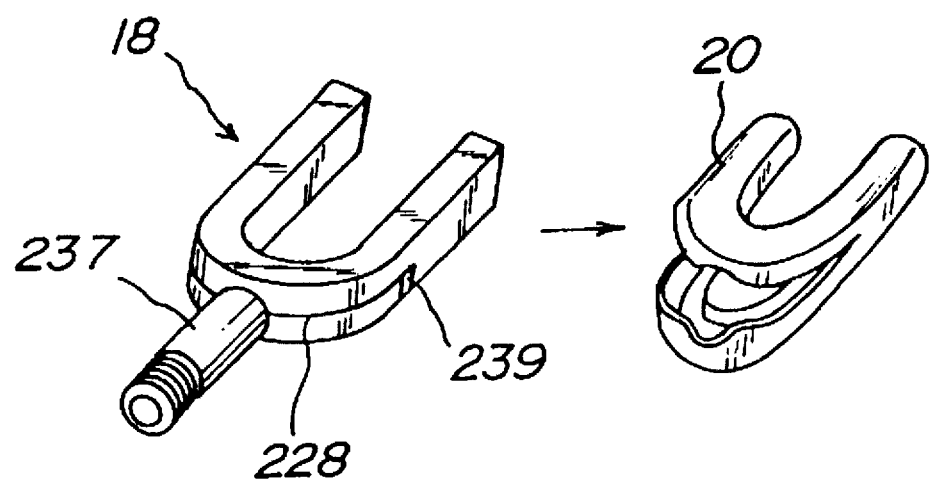

FIG_38
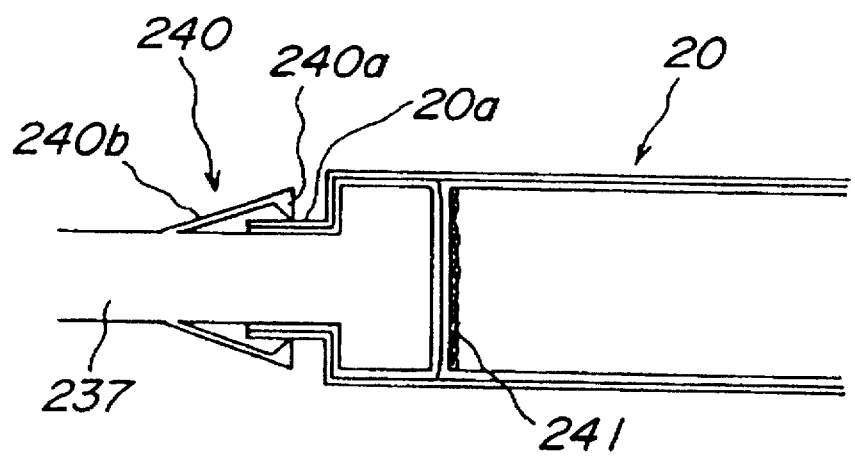
FIG_39
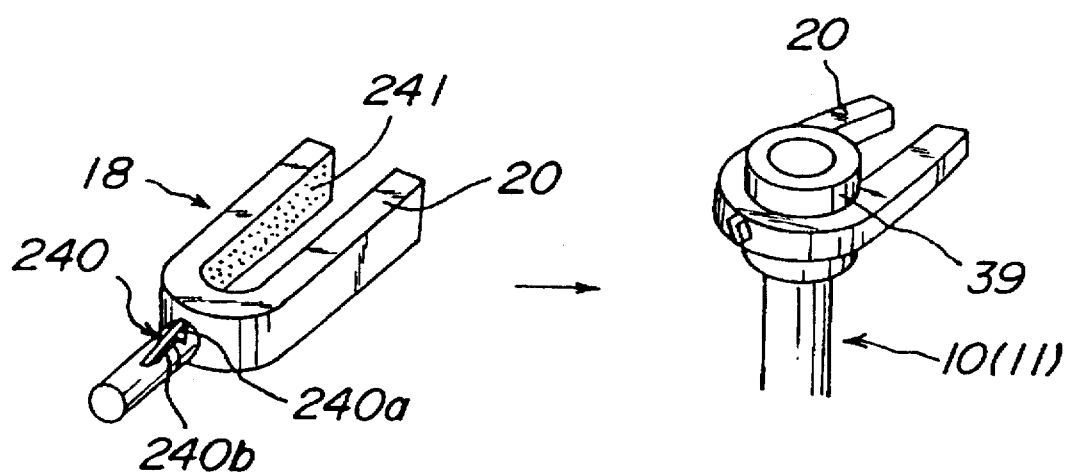

FIG_40
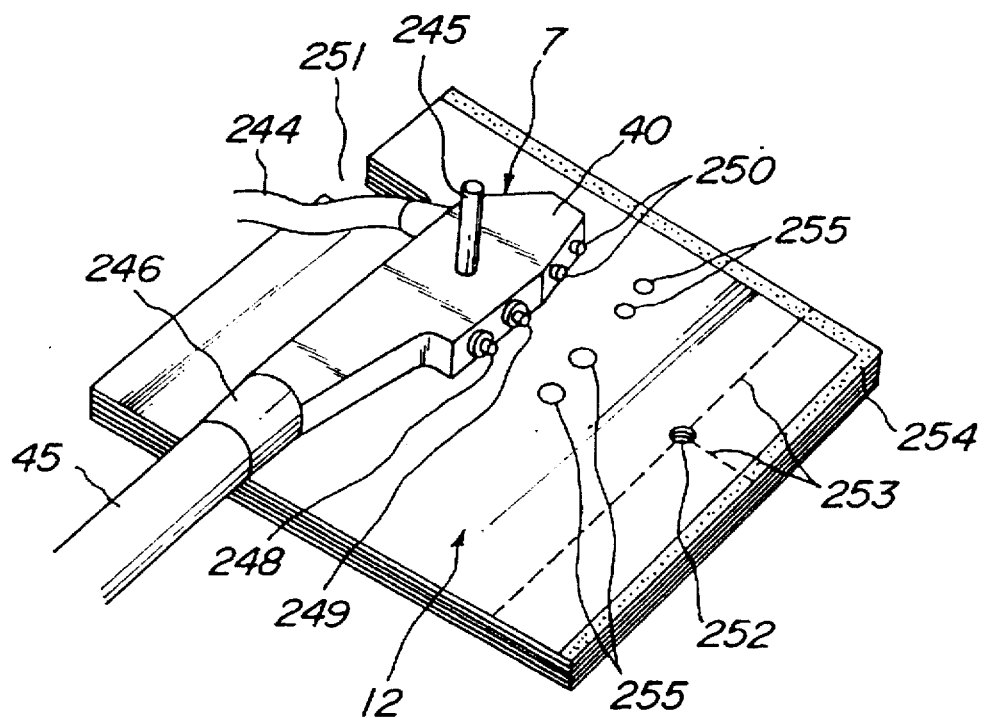
FIG_41
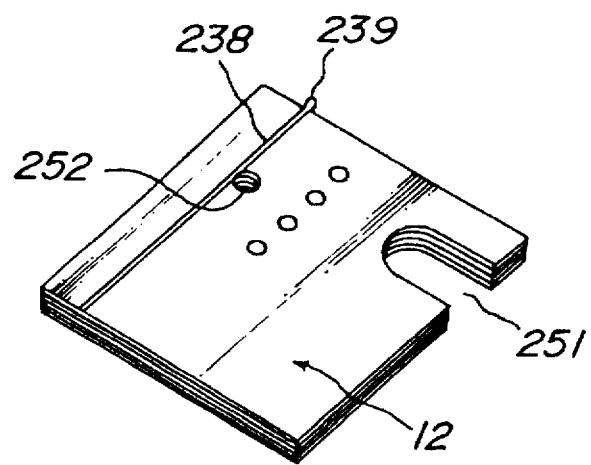

FIG_45A
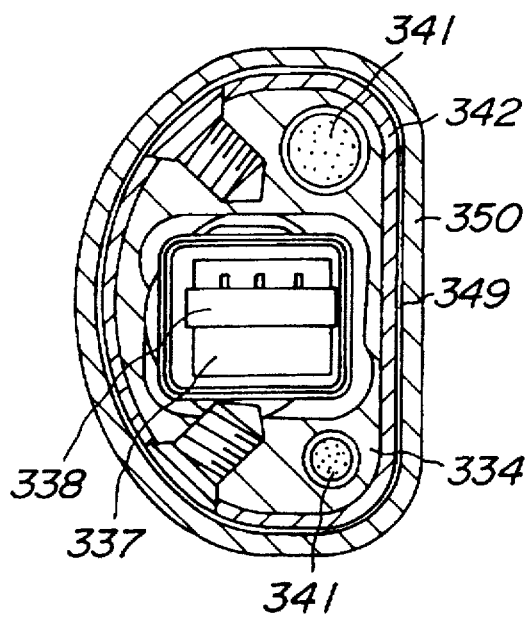
FIG_45B
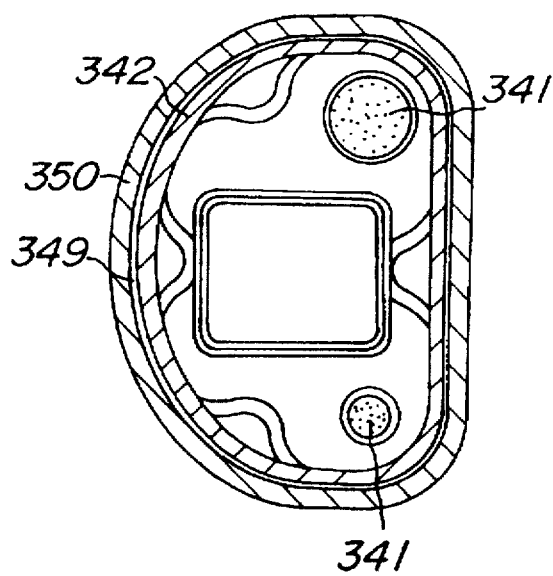
FIG_45C
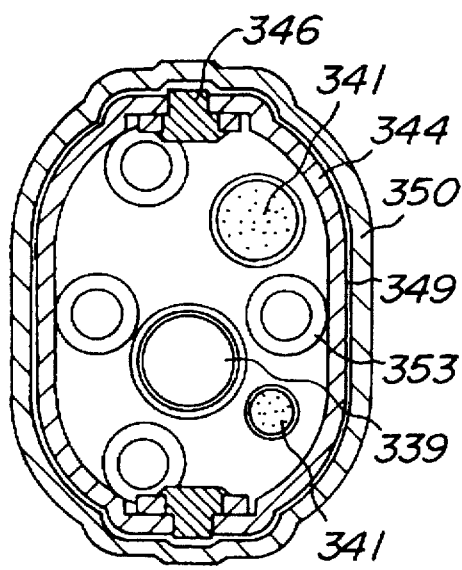
FIG_45D
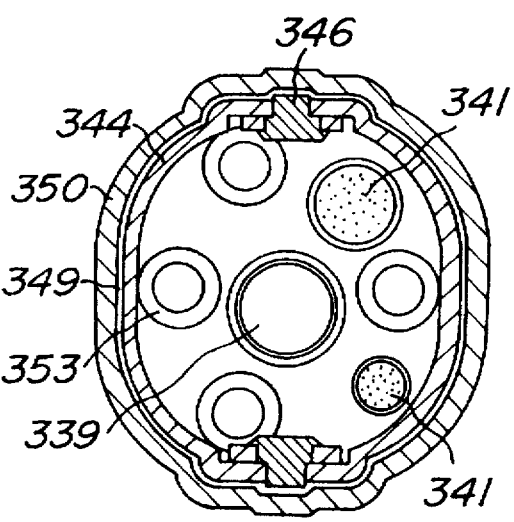

FIG_45E
FIG_45F
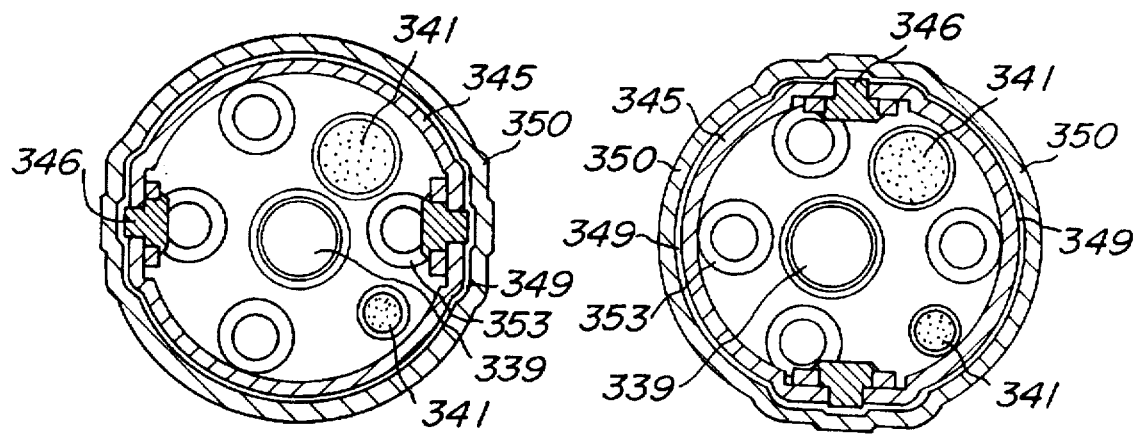
FIG_45G
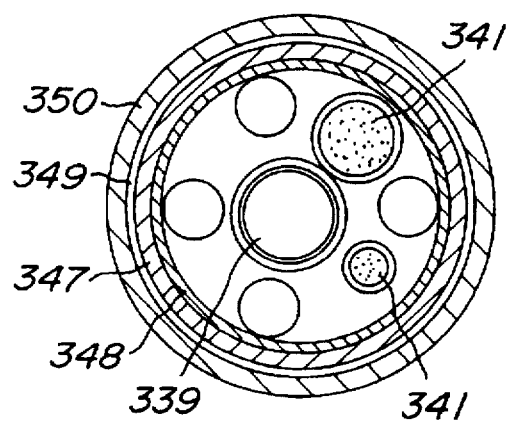

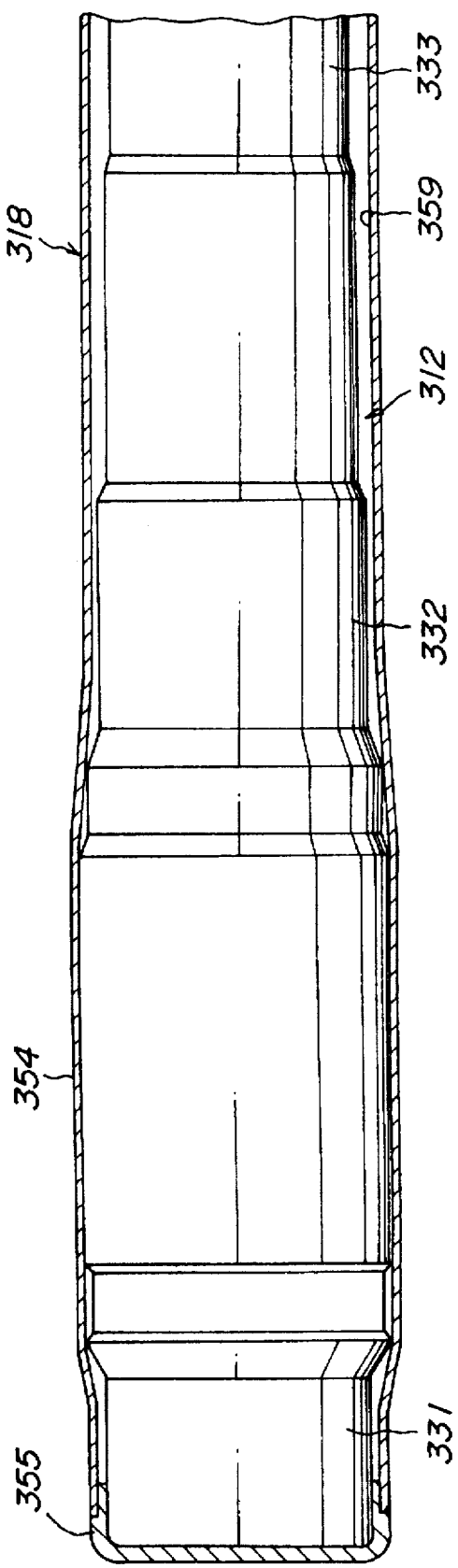
FIG_47

FIG_50A
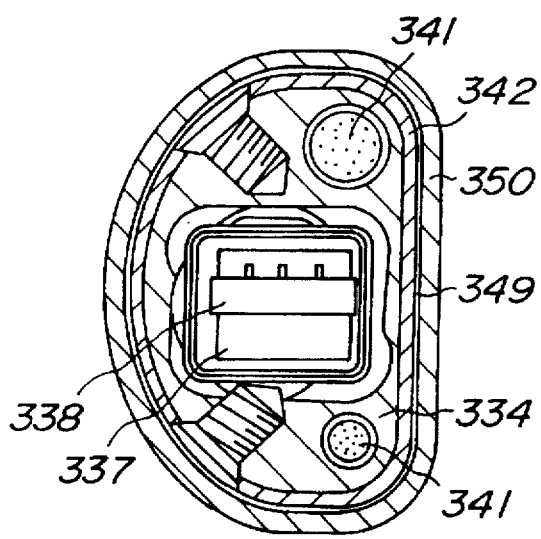
FIG_50B
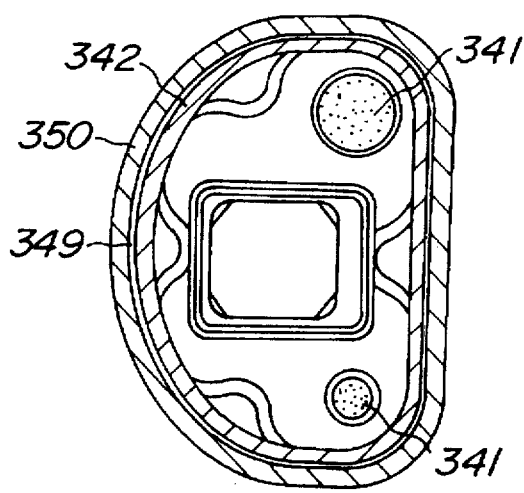
FIG_50C
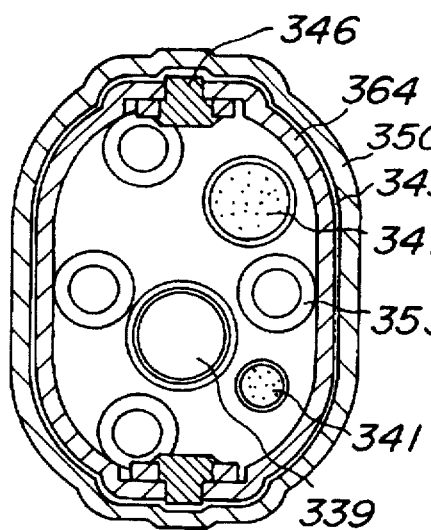
FIG_50D
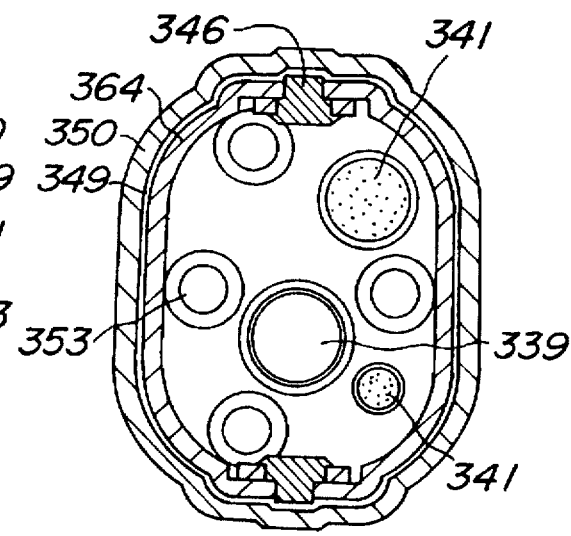

FIG_51
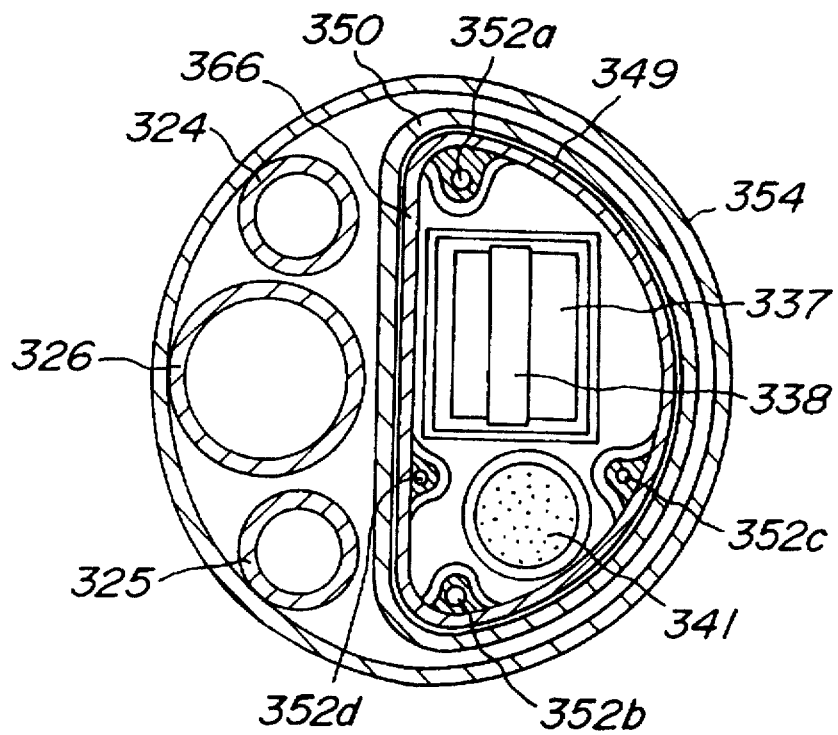
FIG_52
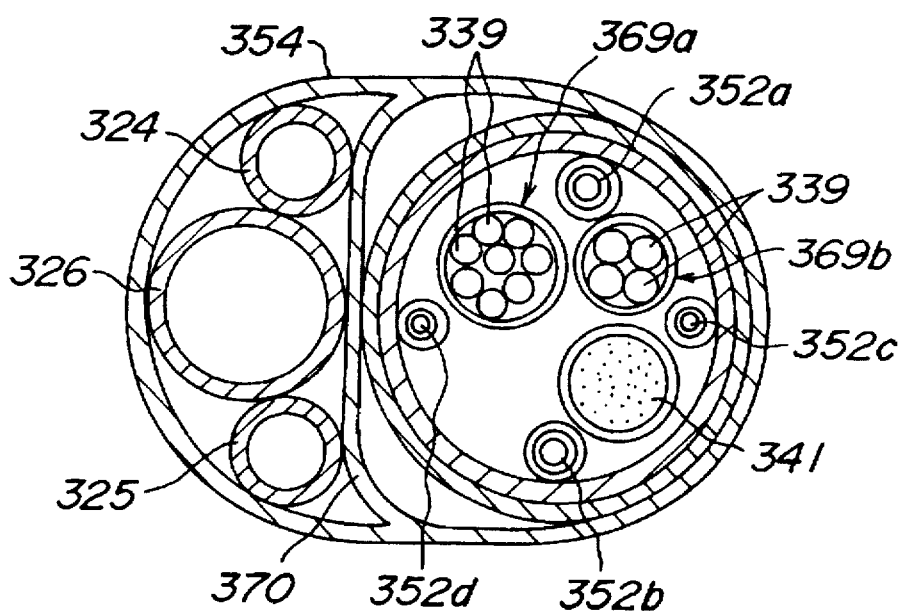

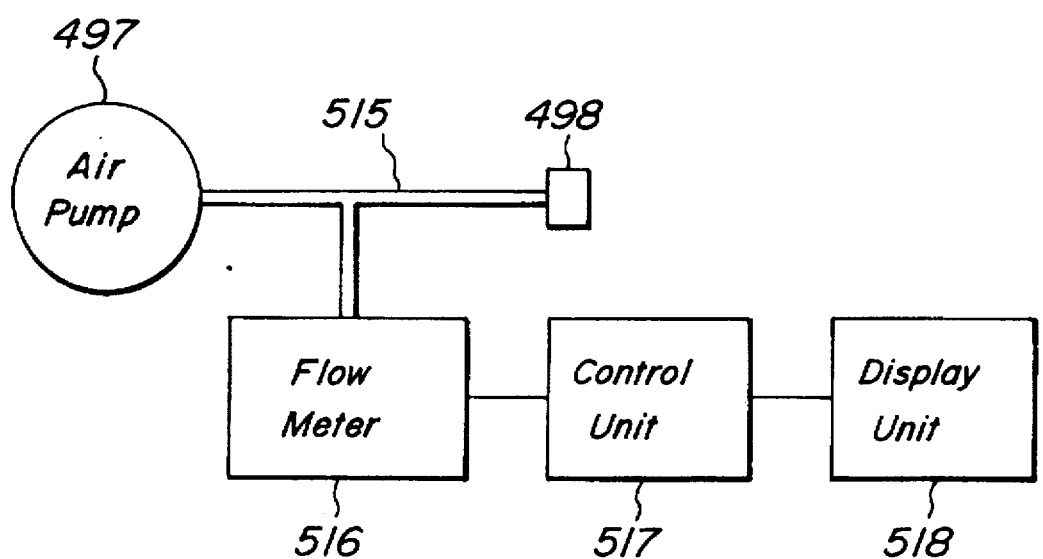
FIG_55

5,674,182

ENDOSCOPE SYSTEM INCLUDING ENDOSCOPE AND PROTECTION COVER

This is a continuation-in-part application of U.S. patent application Ser. No. 08/038,092 filed on Mar. 30, 1993, now abandoned.

BACKGROUND OF THE INVENTION

1. Field of the Invention

The present invention relates to an endoscope system including an endoscope and a protective cover; more particularly, the invention pertains to an endoscope system wherein the endoscope includes an insertion section insertable into a cavity to be inspected and having a proximal end to which an operation section is connected, and the protective cover comprises an insertion section cover for covering the insertion section of the endoscope.

2. Description of the Prior Art

An endoscope system has been widely utilized for providing diagnostic and therapeutic indications for coeliac cavities of patients and for internal inspecting of mechanical structures. To this end, various kinds of endoscopes have been developed. For instance, in order to inspect or treat the oesophagus, stomach or duodenum, upper endoscopes have been utilized. Further, colonoscopes have been developed to examine colons and sigmoidoscopies have been proposed to inspect rectums and sigmoid colons. When the endoscope is used, an insertion portion of the endoscope has to be inserted into a cavity of a patient, so that the outer surface of the insertion section of the endoscope is contaminated with living tissues and liquids. Such contaminated endoscopes cannot be successively used for other patients.

Therefore, once the endoscope has been used to diagnose and/or treat a patient, it is necessary to clean and sterilize the used endoscope. Of course, endoscopic procedures cannot be performed with the endoscope while it is being cleaned, which requires substantial time. In order to mitigate such an idle time, it is necessary to prepare a large number of endoscopes. However, endoscopes are rather expensive, so that it is practically difficult to prepare a large number of endoscopes, particularly in a small hospital or clinic. Therefore, in almost all hospitals and clinics, in practice, after an endoscope has been used for examining or treating a patient, the used endoscope is immediately cleaned. Typically, this cleaning requires several minutes to ten minutes. In order to effect complete washing and sterilization, the cleaning has be to performed for several tens of minutes.

Further, the endoscope has various channels such as an air supply channel, a water supply channel, a suction channel, and a forceps channel which extend along the insertion section from a proximal end to a distal end thereof, and these channels, except for the forceps channel are connected via tubes to respective devices such as an air supply pump, a water supply pump, a water suction pump and an air suction pump. These channels are subjected to contact with living tissues and liquids. However, in order to clean these channels of the endoscope completely, a relatively long period of time is required. Thus, the endoscope can not be utilized efficiently during the long cleaning time. In a large hospital or clinics, a large number of endoscopes may be prepared in order to mitigate the problem of cleaning time. However, this solution results in an increase in operating costs. Further, in small clinics, it is practically impossible to prepare a number of expensive endoscopes.

Moreover, the endoscope might be broken during cleaning and the usable life of the endoscope is liable to be shortened by the cleaning.

In order to avoid the above explained various problems, there has been proposed an endoscope system, in which the endoscope is covered with a sheath-like protection cover having channels formed therein. For instance, U.S. Pat. Nos. 4,721,097, 4,741,326, 4,825,850, 4,869,238, 4,991,564, 4,991,565 and 5,050,585 disclose various kinds of sheath-like protection covers having channels formed therein. In U.S. Pat. No. 4,646,722, there is shown an endoscope system in which the endoscope is covered with a protective sheath, while a tube having channels formed therein is inserted into a U-shaped cutout formed in an outer surface of the endoscope along a longitudinal axis thereof. Upon diagnosis, the insertion section of the endoscope is covered with the protective sheath, and after the inspection, the sheath is removed from the insertion section and is then discarded. Therefore, it is no longer necessary to clean the endoscope after every inspection.

In the above mentioned U.S. Patent Specifications, the sheath-like protection cover is constructed to cover only the insertion section of the endoscope, but does not cover an operation section of the endoscope. It should be noted that the operation section of the endoscope is handled by doctors and operators and is thus brought into contact with the living tissues and liquids of a patient. Therefore, in order to remove the contamination of the operation section of the endoscope due to such living tissues and liquids, it is advantageous to cover not only the insertion section, but also the operation section of the endoscope. In European Patent Publication No. 0 349 479 A1, there is disclosed an endoscope system, in which not only the insertion section, but also the operation section of the endoscope are covered with a protection cover. That is to say, the protection cover comprises a sheath-like portion for covering the insertion section of the endoscope and a bag-like portion for covering the operation section, and the sheath-like portion and bag-like portion are formed integrally. It has been also proposed to form the sheath-like portion and bag-like portion as separate covers. For instance, in European Patent Publication No. 0 341 719 A1, there is proposed another known endoscope system, in which an insertion section of an endoscope is covered with a sheath-like protection cover and an operation section of the endoscope is covered with a bag-like protection cover which is mated or joined with the sheath-like cover in order to prevent contamination through the junction of the sheath-like cover and the bag-like cover.

In any type of the above mentioned endoscope systems including an endoscope and a protection cover, it is highly desirable from a practical viewpoint to provide the endoscope with observation and illumination optical systems, and to provide the protection cover with various channels for passing fluids (e.g., air, water, liquid) and/or treating instruments (e.g., forceps) with optical window members for the optical systems. The optical window members are composed of transparent glass or plastics and are arranged at the distal end of the protective cover. Further, the protective cover should be provided with another channel or channels for inserting the endoscope therein and forming an integral assembly by fixedly securing the endoscope to the protection cover. In this instance, as for the cross-sectional shape of the endoscope insertion channel at the distal end of the protection cover, the cross-section should preferably be of a non-circular shape, such as a D-shape, so as to provide proper and facilitated angular positioning of the endoscope relative to the insertion channel of the protective cover, and further in view of providing a space-saving arrangement of the various constituent elements at the distal end of the cover, as mentioned above. However, when the endoscope is formed to have a complementary non-circular cross-section throughout the entire length, the machining of the endoscope cannot be effected with satisfactory manufacturing productivity and, hence, it becomes difficult to lower the cost of the entire endoscope system.

As mentioned above, the protection cover includes various constituent elements which are arranged at its distal end surface, e.g., optical window members, a forceps channel, nozzles, etc. During use, the distal end of the endoscope is situated behind an optical window member at the distal end of the protective cover. This optical window member has a radial dimension which is larger than that of the endoscope. One radial side of the protective cover affords a space for accommodating the endoscope while a channel tube element extends along another radial side of the protective cover from the proximal end to the distal end.

In this instance, when the distal end of the channel tube element is arranged in alignment with, and connected to, a distal end member of the protective cover at its end surface, the distal end member has to be provided with a through-opening extending longitudinally therethrough and having a cross-sectional area which corresponds to that of the channel tube element, inclusive of the area of the wall thickness thereof, so that it becomes difficult to reduce the diameter of the protective cover.

More particularly, a limited cross-sectional area of the distal end surface of the protective cover is partly occupied by the cross-sectional area of the wall of the channel tube element, thereby necessitating a relatively large diameter of the protective cover. For reducing the diameter of the protective cover, it may be conceivable to arrange the channel tube element as close to the optical window member as possible, although the channel tube element has to be spaced from the optical window member at least by a distance corresponding to the wall thickness of the channel tube element. Thus, there is a limit to the reduction of the diameter of the endoscope system, even when the channel tube element is arranged close to the optical window member. Of course, a large diameter endoscope system is quite undesirable and the system should have a diameter as small as possible so as to minimize or mitigate pain, or physical or mental uneasiness, experienced by patients during actual use of the system.

SUMMARY OF THE INVENTION

It is a primary object of the present invention to provide a novel and useful endoscope system including an endoscope and a disposable protective cover, in which an insertion section of the endoscope can be easily inserted into the protection cover.

It is another object of the invention to provide an endoscope system including an endoscope and a protection cover which is used repeatedly after cleaning, in which an undesired hole formed in the protection cover can be detected.

It is another object of the invention to provide an endoscope system including an endoscope and a protection cover, in which an optical window member provided at a distal end of the protection cover can be effectively prevented from being damaged or removed by an insertion of the endoscope.

It is another object of the invention to provide an endoscope system which can be readily manufactured with higher productivity and at a lower cost, and which yet permits a proper and facilitated angular positioning of the endoscope relative to an insertion channel of the protection cover.

It is another object of the present invention to provide a novel and useful endoscope system including an endoscope and a protective cover, and having a diameter which can be reduced without sacrificing any of the functional advantages of the entire system.

According to a first aspect of the invention, an endoscope system comprises:

an endoscope including;

an inserting section having a proximal end and a distal end and being insertable into a cavity to be inspected, the insertion section comprising a distal end construction member having an objective optical system installed therein, a bending portion coupled with the distal end construction member and a flexible portion connected to the bending portion and extending to the proximal end of the insertion section, an outer configuration of the distal end construction member having a non-circular cross section and an outer configuration of the flexible portion having a substantially circular cross section, and an operation section connected to the proximal end of the insertion section; and a protection cover having a proximal end and a distal end including;

an insertion section inserting channel into which the insertion section of the endoscope is insertable and which extends from the proximal end to the distal end, a distal end member provided at the distal end of the protection cover and including an accommodating portion having a non-circular shape corresponding to the non-circular cross section of the distal end construction member of the insertion section of the endoscope, and a conduit channel extending substantially in parallel with the insertion section inserting channel from a proximal end to a distal end, at least one tube being insertable into the conduit channel.

According to a preferable embodiment of the invention, the non-circular cross section of the distal end construction member is formed as a substantially semicircular or oval shape and the conduit channel is formed to have substantially semicircular or oval cross section. In such a case, the protection cover is advantageously formed by a doublelumen tube having a circular cross section.

According to a preferable embodiment of the invention, an outer configuration of a distal end portion of the bending portion has the non-circular cross section and an outer configuration of a proximal end of the bending portion has a circular cross section. That is to say, a cross section of the bending portion is changed from a non-circular shape into a circular shape within a length of the bending portion.

According to another embodiment of the endoscope system according to the invention, the distal end member of the protection cover includes a distal end plate member and a transparent optical window member through which light reflected by an object under inspection is made incident upon the objective optical system and an outer surface of the distal end construction member of the insertion section of the endoscope is brought into contact with an inner surface of the distal end member of the protection cover.

In a preferable embodiment of the endoscope system according the invention, a recess is form in an outer surface of the distal end plate member made of opaque material, the transparent optical window member is clamped into the recess, and at least one outwardly tapered opening is formed in the distal end plate member such that the opening is exposed in the recess.

In a preferable embodiment of the endoscope system according to the invention, in order to reuse a protection cover, a used protection cover is washed and sterilized and then, it is confirm whether or not a hole is formed in the protection cover, the insertion section inserting channel has an opening at the proximal end, with the opening being detachably coupled in an airtight manner an inflating tube of a protection cover cleaning apparatus which comprises means for detecting a leakage of an air from the inflated insertion section inserting channel.

According to another aspect of the invention, there is provided an endoscope system which comprises:

an endoscope including an insertion section having a proximal end and a distal end and being insertable into a cavity to be inspected, and an operation section connected to the proximal end of the insertion section; and a protection cover which covers the insertion section of the endoscope and has a proximal end and a distal end;

whereby the insertion section of the endoscope is of non-circular cross section at its proximal end and distal end, and is of a substantially circular cross section in a region between the proximal and distal ends of the endoscope; and the protection cover has a first channel and a second channel at the proximal end and distal end thereof, respectively, the first and second channels are of non-circular cross section for engaging therein the distal end and proximal end of the endoscope, respectively.

According to still another aspect of the present invention, there is provided an endoscope system which comprises:

an endoscope including an insertion section having a proximal end and a distal end and being insertable into a cavity under inspection, and an operation section connected to the proximal end of the insertion section; and a protection cover which covers the insertion section of the endoscope, the protection cover having a proximal end and a distal end, and including a channel tube which extends between the proximal end and the distal end of the protection cover, a distal end member provided at the distal end of the protection cover, and an optical window member arranged at an end surface of the distal end member;

whereby the distal end of the channel tube of the protection cover is connected to the distal end member of the protection cover at location which is situated on a rear side of the optical window member.

The above mentioned endoscope system according to the present invention typically includes, besides an endoscope and a protection cover, a universal cord which serves to connect the operation section of the endoscope to at least one peripheral device, such as light source device, video processor, fluid source, and which may be thus readily brought into contact with hands of doctors or operators and thereby contaminated. Thus, in addition to use of the protection cover as discussed above, it is highly desirable to also use a universal cord cover for tightly enclosing the universal cord. The protection cover may be formed by preparing a large sheet and cutting the sheet into desired length and width of the universal cord cover, each time the endoscope system is used. In this instance, when the universal cord cover has insufficient length and/or width, the intended function of the universal cord cover is not completely achieved, while when the universal cord cover has excessive length and/or width, it becomes difficult to lower the cost of the universal cord cover. Moreover, the large sheet is not easy for handling and has to be folded into a size appropriate for storage.

Therefore, the present invention also provides a novel endoscope system comprising:

an endoscope including an insertion section having a proximal end and a distal end and being insertable into a cavity under inspection, and an operation section connected to the proximal end of the insertion section;

a protection cover which covers the insertion section of the endoscope;

a universal cord which serves to connect the operation section of the endoscope to at least one peripheral device; and a universal cord cover comprising an elongated strip which is wound into a roll in its non-use or storage condition, and which is unwound from the roll and is wound around the universal cord in its use condition.

BRIEF DESCRIPTION OF THE DRAWINGS

The present invention will be explained in further detail hereinafter with reference to the accompanying drawings, wherein:

FIG. 1 is a perspective view showing the entire construction of a preferred embodiment of the endoscope system according to the present invention;

FIG. 2 is a longitudinal-sectional view showing the endoscope system of FIG. 1;

FIGS. 3A, 3B and 3C are cross-sectional views of the endoscope system taken along the lines 3A—3A, 3B—3B and 3C—3C in FIG. 2, respectively;

FIG. 4 is a fragmentary perspective view showing one embodiment of the endoscope which may be used in the present invention;

FIG. 5A is a front view of the endoscope of FIG. 4 at its distal end;

FIGS. 5B and 5C are cross-sectional views of the endoscope taken along the lines 5B—5B and 5C—5C in FIG. 4, respectively;

FIG. 6 is a fragmentary perspective view showing another embodiment of the endoscope which may be used in the present invention;

FIG. 7A is a front view of the endoscope of FIG. 6 at its distal end;

FIGS. 7B, 7C and 7D are cross-sectional views of the endoscope taken along the lines 7B—7B, 7C—7C and 7D—7D in FIG. 6, respectively;

FIGS. 8 to 12 show various embodiment of the endoscope system capable of positioning the distal end of the endoscope relative to the distal end member of the protection cover;

FIGS. 13 to 15 show various embodiment of the endoscope system including a protection cover suitable for magnified observation;

FIG. 16 show an example of a mouthpiece for the endoscope system;

FIG. 17 shows a sliding tube for the endoscope system;

FIG. 18 is a front view of the distal end member for the endoscope system according to another embodiment of the present invention;

FIGS. 19A and 19B are schematic sectional views explaining the principle of the present invention with which the outer diameter of the distal end member can be minimized;

FIG. 20 is a fragmentary longitudinal-sectional view of the distal end member for the endoscope system according to another embodiment of the present invention;

FIG. 21 is an explanatory view showing part of the optical system of FIG. 20;

FIG. 22 is a fragmentary longitudinal-sectional view of the distal end member for the endoscope system according to still another embodiment of the present invention;

FIG. 23 is an explanatory view showing part of the optical system of FIG. 22;

FIG. 31 is a schematic view illustrating a use state of the universal cord cover in the cover holding member of FIG. 30;

FIG. 32 is a partly schematic view of another embodiment of the cover holding member for use with the universal cord cover;

FIG. 33 is a schematic view illustrating a use state of the universal cord cover in the cover holding member of FIG. 32;

FIG. 34 is a perspective view of another embodiment of the cover holding member suitable for use with the universal cord cover;

FIG. 35 is a schematic view showing a rocking mechanism of the cover holding member;

FIG. 36 is a schematic view showing one embodiment of the cover for the cover holding member;

FIG. 37 is an explanatory view showing the manner of using the cover of FIG. 36;

FIG. 38 is a schematic view showing another embodiment of the cover for the cover holding member;

FIG. 39 is an explanatory view showing the manner of using the cover of FIG. 38;

FIG. 40 is a perspective view showing one embodiment of the operation section cover;

FIG. 41 is a perspective view showing another embodiment of the operation section cover;

FIGS. 45A, 45B, 45C, 45D, 45E, 45F and 45G are lateral cross sections cut along lines A—A, B–D, C—C, D—D, E—E, F—F and G—G, respectively shown in FIG. 44;

FIG.47 is a longitudinal cross sectional view of a distal end portion of the insertion section inserted into the protection tube according to the invention;

FIGS. 50A, 50B, 50C, 50D, 50E and 50F are lateral cross sections cut along lines A—A, B—B, C—C, D—D, E—E, F—F and G—G, respectively shown in FIG. 48;

FIG. 51 is a lateral cross sectional view depicting another embodiment of the distal end portion of the insertion section inserted into the protection cover according to the invention;

FIG. 52 is a lateral cross sectional view depicting still another embodiment of the distal end portion of the insertion section inserted into the protection cover according to the invention;

FIG. 55 is a block diagram showing an apparatus for detecting leakage of the protection cover;

FIG. 56 is a flow chart for explaining the cleaning and leak monitoring operation;

DESCRIPTION OF THE PREFERRED EMBODIMENTS

Figure 13:
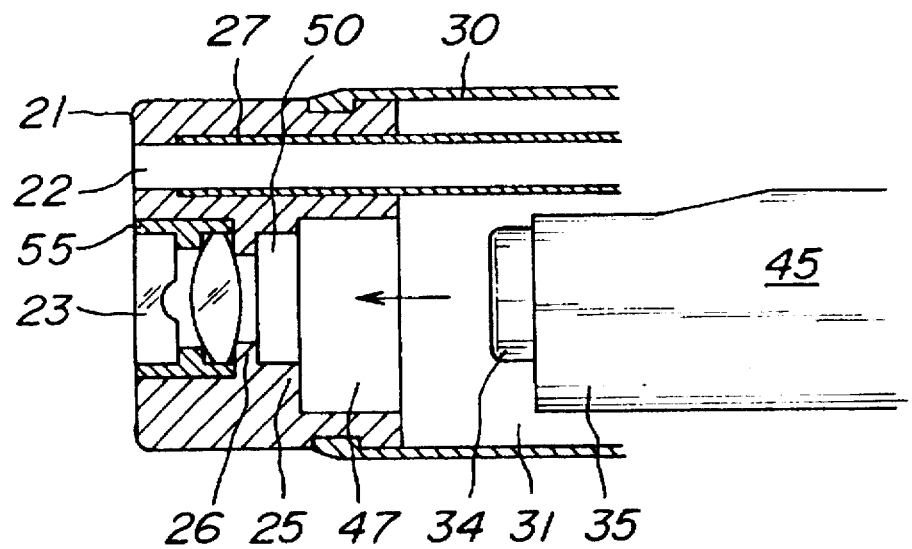

FIG. 1 is a schematic view showing a preferred embodiment of the present invention. The endoscope system according to the invention is designated as a whole by reference numeral 9, and includes an endoscope 7, a protection cover 10 and various peripheral devices. A majority of the peripheral devices are installed in a caster box 1, including a light source device 2, a video processor device 3, a fluid control device 4, an inflator device 5 and a visual image monitoring device 6. The operational functions of these peripheral devices will be more fully explained later. The endoscope 7 forming part of the endoscope system 9 is connected to the light source device 2 via a connector 256, and associated with a curl cord 8 which is to supply the video processor 3 with an electric signal from an image pickup element at the distal end of the endoscope 7, such as a CCD 37 shown in FIG. 2.

The protection cover 10 is to protect the endoscope 7 from contamination, and is formed of an insertion section cover 11, an operation section cover 12 and a universal cord cover 13, all of which are in sterilized prior to use and discarded after use. The insertion section cover 11 encloses an insertion section 45 of the endoscope 7, which can be inserted into a body cavity for medical diagnosis, examination or treatment, for example. The operation section cover 12 encloses an operation section 40 of the endoscope 7, which is connected to the proximal end of the insertion section 45. The operation section cover 12 is associated with an angle knob cover 17 which encloses an angle knob portion of the operation section 40. The universal cord cover 13 encloses a universal cord 244 of the endoscope 7, which connects the operation section 40 of the endoscope 7 with the peripheral devices mentioned above. Thus, the universal cord cover 13 encloses at least major parts of fluid conduit tubes 73, 74, 75 respectively extending between the fluid control device 4 and various channels formed along the endoscope 7, such as an air channel, a water channel and a forceps channel 27 for passing a forceps therethrough, which can also be used as a suction channel.

The inflator device 5 is to supply air into the insertion section cover 11 and inflate it in order to facilitate insertion and removal of the endoscope 7 relative to the insertion section cover 11. To this end, an inflator tube 14 is connected to the inflator device 5 and also to a port 33 formed through the wall of the insertion section cover 11. When the endoscope 7 is to be inserted into the insertion section cover 11 prior to use of the endoscope system, or to be removed therefrom after the endoscope system has been used, it is highly desirable to retain the insertion section cover 11 by a retainer 15. The retainer 15 may include a substantially U-shaped arm 18 with which the proximal end region of the insertion section cover 11 is engaged.

A laser device 51 is provided as a further peripheral device, and includes a laser probe 52 and a foot switch 53. Whenever necessary, the laser probe 52 can be inserted into the forceps channel 27 through a forceps inlet 29 formed in the insertion section cover 11. Then, the forceps can be projected from a distal end member 21 of the protection cover 10 into the body cavity of a patent.

The details of one embodiment of the endoscope system 9 including the endoscope 7 and the protection cover 10 will be explained below, with reference to FIG. 2, FIGS. 3A to 3C, FIG. 4 and FIGS. 5A to 5C.

As particularly shown in FIG. 2, the protection cover 10 is provided with a distal end member 21. The distal end member 21 has a distal end surface in which a forceps outlet 22 and an observation window member 23 are arranged. The window member 23 is formed of a transparent cover glass which is arranged at a location corresponding to an observation optical system of the endoscope 7. The observation optical system of the endoscope 7 includes an objective lens 36 retained within a lens holder 34 which projects from the distal end 35 of the endoscope 7, and an observation window member formed of a transparent cover glass arranged at the distal end of the lens holder 34. Similarly, though not shown in FIG. 2, the distal end surface of the distal end member 21 is further provided with an illumination window member of a transparent cover glass which is arranged at a location corresponding to an illumination optical system of the endoscope 7, as well as an air nozzle and a water nozzle. The observation window member 23 and the illumination window member are fitted into the distal end member 21 axially from the side of the distal end surface, and are then fixative secured to the distal end member 21 by an adhesive agent applied to their respective outer peripheries. A tube forming the forceps channel 27 is axially inserted into the protection cover 10 from the side of the operation section 40. The distal end of this tube is engaged with and fixedly secured to a surrounding inner periphery of a bore 44 which is formed in the distal end member 21 as the forceps outlet 22.

The distal end member 21 of the protection cover 10 is provided with a channel 31 in which the endoscope 7 is inserted, another channel 47 which is opened rearwardly in the longitudinal direction, i.e. toward the operation section 40, and in which the distal end of the endoscope 7 is engaged, and still another channel 50 in which the lens holder 34 is engaged. The last-mentioned channel 50 terminates at a shoulder 26 which serves as a positioning stopper 26 for the lens holder 34. These channels 31, 47, 50 are axially aligned with each other.

The insertion section cover 11 of the protection cover 10 includes an elongated sheath 30 formed of a soft material, which serves to shield the insertion section 45 of the endoscope 7 from an external environment. The sheath 30 has a distal end which is connected to the distal end member 21 of the protection cover 10 in a fluid-tight manner.

As shown in FIG. 2, a mouthpiece 32 is provided at the proximal end of the insertion section cover 11 and connected to the operation section 40. The mouthpiece 32 is provided with a branched channel 28 which serves as the forceps inlet 29, and also with the air inlet port 33 to which the inflator tube 14 is connected. The forceps inlet 29 and the air inlet port 33 are spaced from the sheath 30 in the longitudinal direction, and situated adjacent to the operation section 40. The mouthpiece 32 is further provided with a channel 49 for the proximal end portion 38 of the endoscope 7 to be engaged with the operation section 40. Various conduit tubes, including a suction tube 14 in communication with the forceps channel 27, are arranged so as to project from the end surface of the mouthpiece 32. The suction tube 14, water conduit tube 74 and air conduit tube 75 are passed inside of the universal cord cover 13, along the universal cord 244, and extend toward the respective peripheral devices as discussed above with reference to FIG. 1. As shown in FIG. 2, furthermore, the mouthpiece 32 is also provided with a retainer mount 39 on an outer peripheral surface, and a mount 60 for the operation section 40 on its end side.

One important aspect of the present invention is to provide an arrangement of the endoscope system including an endoscope and a disposable protection cover, which can be readily manufactured with higher productivity and at a lower cost, while permitting a proper and facilitated angular positioning of the endoscope relative to the insertion channel of the protection cover.

Thus, as shown in FIGS. 3A to 3C, the insertion section cover 11 has channels 47, 49 at a distal end and proximal end for engaging with the distal end 35 and the proximal end 38 of the endoscope 7, respectively, and these channels 47, 49 are of non-circular, substantially D-shaped cross-section. Corresponding to such arrangement of the insertion section cover 11, as shown in FIG. 4 and FIGS. 5A to 5C, the insertion section of the endoscope 7 is of non-circular, substantially D-shaped cross-section at its distal end 35 and proximal end 38, and of a circular cross-section in a region between the distal end 35 and the proximal end 38 of the endoscope 7.

As particularly shown in FIG. 4, the endoscope 7 includes the insertion section 45 and the operation section 40. The insertion section 45 includes the objective lens holder 34, a light guide holder 43, the distal end region 35, a bendable portion 62 and a flexible portion 63, which are arranged in the stated sequence as seen from the distal end side. The operation section 40 has a mount portion 38. The objective lens holder 34 and the light guide holder 43 are formed to have substantially the same length, and project from the distal end 35 of the endoscope 7 with a substantially cylindrical configuration, as shown in FIG. 4. The objective lens holder 34 and the light guide holder 43 are provided with an observation window cover glass 41 and a light guide cover glass 42 on their respective front ends, as shown in FIG. 5A.

As shown in FIGS. 4 and 5A, the D-shaped cross-section of the distal end 35 of the endoscope 7 may be formed of a basic cylindrical body with an outer diameter which is substantially the same as that of the insertion section 45 of the endoscope 7, by effecting a horizontal cut in its upper region. As shown in FIGS. 4 and 5B, the bendable portion 62 and flexible portion 63 of the insertion section 45 of the endoscope 7 are of circular cross-section substantially throughout the entire length of the insertion section 45. This circular cross-section of the insertion section 45 is smoothly adjoined with the D-shaped cross-section of the distal end 35.

The mount portion 38 of the operation section 40 arranged adjacent to the insertion section 45 may also have a non-circular, substantially D-shaped cross-section, which is formed of a basic cylindrical body with a somewhat larger diameter. Alternatively, the non-circular cross-section of the mount 38 may for example be oval, etc., provided that a proper angular positioning can be assured.

The operation section 40 of the endoscope 7 is provided with a conduit tube channel 46 for passing the conduit tubes of the protection cover 10, etc., and a mount 60 (FIG. 7) to be engaged with the insertion section cover 11.

Referring also to FIG. 2 and FIGS. 3A to 3C, the structural features and the manner of assembly of the endoscope 7 and the protection cover 10 will be explained in greater detail hereinafter.

As shown in FIGS. 2 and 3A, the distal end member 21 of the protection cover 10 is provided with a channel 50 corresponding to the objective lens holder 34 of the endoscope 7, and an air/water conduit channel 48 in addition to the forceps channel 27 and the channel 47 for the distal end 35 of the endoscope 7. As shown in FIG. 3B, furthermore, the mouthpiece 32 to be connected to the operation section 40 has the water conduit channel 74 and the air conduit channel 75 which are branched from the air/water conduit channel 48, and the channel 49 of the D-shaped cross-section corresponding to the mount 38 of the endoscope 7 for connecting the operation section 40.

The assembly of the endoscope 7 and the protection cover 10 can be performed in the following manner. That is, when the endoscope 7 is inserted into the insertion section cover 11, the endoscope 7 in the first place is gradually advanced until the distal end 35 of the endoscope 7 comes into abutment with the distal end member 21 of the protection cover 10 such that the objective lens holder 34 and the distal end 35 are aligned and engaged with the channels 50 and 47, respectively. Then, while passing the conduit tube 73 and the like into the conduit tube channel 46, the mount 38 of the endoscope 7 for the operation section 40 is inserted into the channel 49.

With the above-mentioned arrangement of the present invention, due to the non-circular, substantially D-shaped cross-section of the distal end 35 of the endoscope 7 and of the corresponding channel 47 in the protection cover 10, twisting of the insertion section 45 of the endoscope 7 results in a corresponding twisting of the insertion section cover 11. Similarly, due to the non-circular, substantially D-shaped cross-section of the mount 38 at the proximal end of the endoscope 7 and of the corresponding channel 49 in the mouthpiece 32 of the protection cover 10, twisting of the operation section 45 results in a corresponding twisting of the endoscope 7 and the insertion section cover 11. Thus, it is possible to positively prevent undesirable rotation of the endoscope 7 and the protection cover 10 relative to each other and to effectively preserve a definite angular relationship between the two elements. Of course, after the mount 60 for the operation section 40 has been secured to the mouthpiece 32, it is possible to prevent undesirable axial relative displacement between the endoscope 7 and the protection cover 10.

It will be readily appreciated from the foregoing detailed description that the above-mentioned embodiment of the present invention provides various functional advantages as follows:

That is, the improved endoscope system can be manufactured with a high manufacturing productivity and at a low cost. This is due to the local formation of the non-circular, substantially D-shaped cross-section as required only for the proximal and distal ends of the endoscope 7 and the insertion section cover 11. The assembly of the endoscope 7 and the protection cover 10 is significantly facilitated, because the angular positioning of the endoscope relative to the protection cover is achieved simultaneously. The endoscope 7 and the protection cover 10 can be maintained at a definite angular relationship with each other. The required non-circular cross-section can be formed without particular difficulties in the production technology. The local formation of the non-circular cross-section serves to lower the manufacturing cost, as compared to formation of the non-circular cross-section throughout the entire length.

In the embodiment described above, the insertion section 45 of the endoscope has a circular cross-section throughout the entire region between the proximal and distal ends. However, the insertion section 45 may have a partially non-circular cross-section at some location other than the proximal and distal ends. For example, the insertion section 45 of the endoscope 7 may have a bendable portion 62 of a circular cross-section and a flexible portion 63 of a non-circular cross-section. Alternatively, the insertion section 45 of the endoscope 7 may have a bendable portion 62 of a non-circular cross-section and a flexible portion 63 of a circular cross-section.

Another embodiment of the present invention is shown in FIG. 6 and FIGS. 7A to 7D, wherein the insertion section 45 of the endoscope 7 has a bendable portion 62 of a non-circular cross-section and a flexible portion 63 of a circular cross-section.

Thus, the mount 38 at the proximal end, and the distal end 35 and the bendable portion 62 of the endoscope 7 is of the same D-shaped cross-section having the same basic diameter, while the flexible portion 63 of the endoscope is of circular cross-section having a diameter which is the same as the length of the minor axis of the D-shape, i.e. the dimension of the D-shape as measured in the vertical direction in FIG. 7B. Therefore, the flexible portion 63 of the endoscope 7 has a relatively small diameter as compared to the other regions, and the bendable portion 62 has an inner space which is larger than that of the flexible portion 63, as appreciated from FIGS. 7B and 7C.

There are shown in FIGS. 7B, 7C and 7D further structural elements of the endoscope, which are signal cables 64, light guide bundle 65, angle wire 66, sheath 67 for the flexible portion 63, bending pieces 68, so called A-rubber 69, angle wire support 70 and angle coils 71. These elements by themselves are widely known in the art so that a detailed explanation is omitted herein.

With the above-mentioned arrangement of the embodiment shown in FIG. 6 and FIGS. 7A to 7D, due to a relatively small diameter of the flexible portion 63 of the endoscope 7, the insertion section 45 of the endoscope 7 can be passed through the insertion section cover 11 in a facilitated manner. That is, after the distal end 35 and the bendable portion 62 of the endoscope 7 have been introduced into the insertion section cover 11, the flexible portion 63 of the endoscope can be readily passed through the channel 49 at the proximal end of the cover 11. Furthermore, it is highly advantageous for the bendable portion 62 to have an inner space which is larger than that of the flexible portion 63, since the bendable portion is bent during a practical use with an angle which is larger than the flexural deformation angle of the flexible portion, and a larger bending angle of the bendable portion 62 can be readily achieved by its large inner space, as appreciated from FIGS. 7B and 7C.

In the case of an endoscope system including an endoscope and a disposable protection cover, it is highly desirable to perform a proper positioning of the distal end 35 of the endoscope 7 relative to the distal end member 21 of the protection cover 10. More particularly, there may be a possibility that dust or other foreign matter will enter into a space between the cover glasses of the protection cover and the respective cover glasses of the endoscope, thereby to deteriorate the observation image. There may be another possibility that the cover glasses of the protection cover and the respective cover glasses of the endoscope are brought into abutment with each other to form scratches in the lens surfaces, which also result in deterioration of the observation image.

Taking these possibilities into consideration, the present invention provides an arrangement wherein the endoscope is prevented from contacting with the inner surface of the cover glasses of the protection cover, and/or the protection cover is prevented from contacting with the distal end surface of the endoscope, i.e., a first objective lens surface.

With reference to FIG. 8 showing the region corresponding to the distal end member 21 of the protection cover 10, the manner of inserting the endoscope 7 of FIG. 2 into the distal end member 21 will be explained. The protection cover 10 is provided with an annular ridge 26 as a shoulder for limiting the axial insertion of the objective lens holder 34. The ridge 26 has an inner diameter which is smaller than the outer diameter of the observation window cover glass 23 and the outer diameter of the objective lens holder 34, such that the axial position of the observation window cover glass 23 and the objective lens holder 34 can be determined in a definite manner. The channel 50 to be engaged with the objective lens holder 34 is made smaller than the axial projection length of the objective lens holder 34 with which it projects from the distal end 35 of the endoscope 7.

The arrangement of the endoscope system explained with reference to FIG. 8 provides various functional advantages. That is, during the insertion of the distal end 35 of the endoscope 7 into the distal end member 21 of the protection cover 10, the distal end surface at the objective lens holder 34 of the endoscope 7 in the first place is brought into abutment with the positioning shoulder 26 to prevent an undesirable direct contact of the lens holder 34 and the objective lens with the observation window cover glass 23 of the protection cover 10. A space is thus left between the objective lens of the endoscope and the observation window cover glass 23 of the protection cover 10. Due to avoidance of direct contact of the lens holder 34 and the objective lens with the observation window cover glass 23 of the protection cover 10, the objective lens and the cover glass 23 are effectively prevented from getting scratches. Without the proper positioning as achieved by the shoulder 26, the endoscope may be inserted too deeply into the distal end member 21 of the protection cover 10, thereby inducing an undesirable dislocation of the cover glass 23.

There is shown in FIG. 9 another embodiment of the endoscope system wherein the channel 50 for the objective lens holder 34 has an axial length which is larger than the axial length of the lens holder 34, so that the lens holder 34 is always spaced from the observation window cover glass 23. Thus, when the objective lens holder 34 of the endoscope 7 is inserted into the channel 50 in the distal end member 21 of the protection cover 10, in the first place the distal end 35 of the endoscope 7 is brought into abutment with a shoulder 25 provided for the distal end member 21 of the protection cover 10 in front of the channel 50. This makes it possible to avoid direct contact of the lens holder 34 and the objective lens with the observation window cover glass 23 of the protection cover 10. The embodiment of FIG. 9 provides functional advantages which are essentially the same as those of the embodiment of FIG. 8. Furthermore, as the case may be, the positioning of shoulder 25 of the distal end member 21 in front of the channel 50 can be formed in a facilitated manner and at a low cost, as compared with the positioning shoulder 26 in the form of an annular ridge on the inner surface of the channel 50.

Still further embodiments suitable for achieving similar functions will be explained below with reference to FIGS. 10 to 12.

FIG. 10 shows an embodiment wherein the observation window cover glass 41 of the endoscope 7 is arranged spaced axially inwardly from the end surface of the objective lens holder 34 so that the end surface of the lens holder 34 is in contact with the observation window cover glass 23 of the distal end member 21 of the protection cover 10. In this instance, the axial length of the channel 50 in the distal end member 21 for the lens holder 34 is made smaller than the axial length of the lens holder 34.

FIG. 11 shows another embodiment wherein the present invention is applied to an oblique observation type endoscope system 139 including an oblique observation type endoscope 140 and a protection cover 141 therefor. As in the embodiment of FIG. 10, when the objective lens holder 34 of the endoscope 140 is inserted into the channel 148, the end surface of the lens holder 34 is brought into contact with the observation window cover glass 23 at the distal end member 21 of the protection cover 141.

FIG. 12 shows still another embodiment wherein the straight observation type endoscope 7 is combined with the protection cover 141 for the oblique observation type endoscope 140. Thus, the protection cover 141 includes an oblique observation type lens 142 retained in a lens holder 143 which is fixedly secured to a channel for the lens holder 143. As in the embodiments of FIGS. 10 and 11, when the objective lens holder 34 of the endoscope 140 is inserted into the channel 148, the end surface of the lens holder 34 is brought into contact with the oblique observation type lens 142 of the protection cover 141. The axial length of the channel 50 in the distal end member 21 for the lens holder 34 is made smaller than the axial length of the lens holder 34, as in the embodiment of FIG. 10.

The present invention may be applied to an endoscope system wherein the same endoscope can be used for magnified observation and for ordinary, unmagnified observation.

When it is desired to perform magnified observation with an endoscope system including an endoscope and a protection cover therefor, the endoscope to be combined with protection cover may be exchanged with an endoscope which is suitable for magnified observation and to be combined with a non-disposable type protection cover. In this case, however, there arises a requirement to stock both types of endoscopes.

Figure 14:
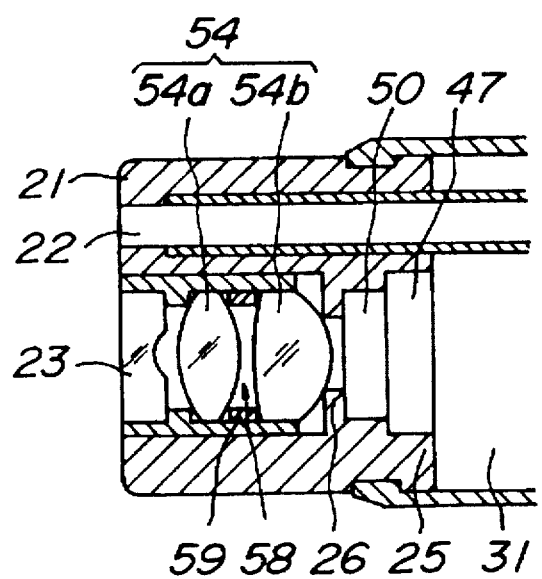

Thus, as shown in FIGS. 13 to 15, the present invention is to provide an arrangement wherein the same endoscope can be used for magnified observation and for unmagnified observation. In this instance, the magnification lens assembly consists preferably of a single lens alone, or one or more lenses combined with a cover glass.

In the embodiment of FIG. 13, the distal end member 21 of the protection cover 10 includes a magnification lens holder 55, an observation window glass 23 and a magnification lens 54 both fitted into the lens frame 55 from both sides. The lens holder 55 is inserted into the distal end member 21 from the distal end side of the protection cover 10 such that the magnification lens 54 is brought into contact with the positioning shoulder 26. The magnification lens has a desired magnification scale which may be 2, for example. Thus, the same arrangement at the insertion section 45 of the endoscope 7 can be readily combined with various magnification lenses of different magnification scale, and it is not necessary to prepare and use a different type of endoscope which is exclusively for the magnified observation.

In the embodiment of FIG. 14, the observation window glass 23 is fitted into the magnification lens holder 55 from the distal end side, while a magnification lens 54a, a spacer ring 59 and another magnification lens 54b are sequentially fitted into the lens holder 55 to form a magnification lens group 58. The lens holder 55 is inserted into the distal end member 21 of the protection cover 10 from the distal end side such that the magnification lens 54b is brought into contact with the positioning shoulder 26. The magnification lens group 58 may consist of more than two lenses. The embodiment provides the functional advantages of the embodiment shown in FIG. 13, and is also advantageous in that the magnification lens group 58 serves to achieve a higher magnification scale while providing a clear image with minimized aberration.

In the embodiment of FIG. 15, the magnification lens 54 is arranged at the front end of the distal end member 21 of the protection cover 10, which is fitted in abutment with the positioning shoulder 26. This arrangement permits a desired magnified observation with a simple structure which can be achieved by minimized cost.

A further embodiment of the endoscope protection cover having channels adopted for preventing distortion caused by laser treatment will be now described.

In such a protection cover, at least the outer surface of the insertion section cover and/or distal end member of the cover is colored, preferably with white, so as to reflect the laser beam.

The distal end member 21 of the endoscope protection cover 10 shown in FIGS. 1 and 2 is made of for example plastics, but the outer surface of the distal end member is colored by applying for example usual white pigment such as $TiO_2$, ZnO and the like. Alternatively, metallic powder pigment such as aluminum powder, gold powder or the like having a high reflectance of laser beam may be used.

Furthermore, the insertion section cover sheath 30 of the cover 10 is made of flexible resin material for example rubber, polyethylene or the like and is also white colored by using white resin material or white pigment which is mixed with the resin material. It should be noted that the color of the outer surface is not limited to white color and another color may be used as long as the color of the outer surface of the cover is able to reflect the laser beam.

With the aforementioned arrangement, the laser beam is reflected on the outer surfaces of the distal end member 21 and the insertion section cover sheath 30 so that the laser beam is not absorbed by the outer surfaces to prevent from burning even if a laser probe 52 of a laser device 5 is extended out of a forceps outlet 22 of the cover 10 when the endoscope system 9 is used as shown in FIG. 1.

Therefore, the endoscope protection cover 10 is not damaged by the laser beam during laser process wherein the laser probe 52 of the laser device 5 is used and consequently, the endoscope and the other parts are not contaminated.

Referring to FIGS. 16 and 17, embodiments of a mouthpiece and a sliding tube for the endoscope according to the invention adapted for improving durability of the cover will be described.

The mouthpiece 56 shown in FIG. 16 includes a body made of polysulfone and can be used in examination of an upper digestive tract, that is, the mouthpiece 56 is fitted in the mouth of a patient and the endoscope 9 is inserted into the upper digestive tract through the mouth piece 56.

To the inner surface of the mouthpiece 56 is releasably bonded a lubricating seal 57 which is made of material such as polyether, imide resin, PTFE, PFA having a superior slip characteristics higher than that of the mouthpiece.

With the aforementioned arrangement of the mouthpiece 56, the sheath 30 of the insertion section cover 11 of the endoscope protection cover 10 is not damaged due to the superior slip characteristics of the lubricating seal 57. Therefore, the mouthpiece 56 is preferably used in combination with the endoscope in order to improve durability of the cover 10. The lubricating seal 57 is detachable and repeatedly usable after sterilization treatment in an autoclave.

Alternatively, the mouthpiece body per se may be made of the same material as that of the lubricating seal 57. Such a mouthpiece may be used for endoscopic examination without the lubricating seal 57.

FIG. 17 illustrates a sliding tube 61 which is used in endoscopic examination of the coil of a patient and is made of the lubricating material similar to the aforementioned lubricating seal 57. Such sliding tube 61 has a superior slip characteristics so that the insertion section cover sheath 30 is not damaged with use of the sliding tube 61 in endoscopic examination.

Another important aspect of the present invention is to provide an endoscope system including an endoscope and a protective cover, and having a diameter which can be reduced without any sacrifice of functional advantages of the entire system.

According to the embodiment of the present invention as shown in FIGS. 18 and 19A and 19B, the protection cover 10 has an observation window member 23 and an illumination window member 124 both arranged in the end surface at the distal end member 21 of the protective cover 10. These window members 23, 124 are respectively situated in front of the observation optical system and illumination optical system at the distal end 35 of the endoscope 7. FIG. 18 further shows a nozzle 125 for discharging air or water into the cavity to be inspected. The distal end of the channel tube for the forceps channel 27 is connected to the distal end member 21 of the protection cover 10 at a location which is situated at an offset location on the rear side of the optical window members 23, 124. The offset amount corresponds at least to the thickness of the glass for the optical window members 23, 124. In this instance, the forceps outlet 22 can be readily arranged close to the optical window member 23 in the end surface of the distal end member 21, independently of the wall thickness of the channel tube of the forceps channel 27. It is thus possible to minimize the outer diameter of the distal end member 21 of the protection cover 10.

FIG. 19A shows a comparative example of the endoscope system wherein the distal end of the channel tube for the forceps channel 27 is connected to the distal end member 21 of the protection cover 10 at a location which is aligned with the optical window member 23 in the end surface of the distal end member 21, i.e. without offset. FIG. 19B shows the arrangement of the endoscope system wherein the distal end of the channel tube for the forceps channel 27 is connected to the distal end member 21 of the protection cover 10 at a location which is situated at an offset location, as mentioned above. It will be appreciated that the arrangement of the present invention shown in FIG. 19D makes it possible to achieve a reduced material thickness D3 as measured between the outer periphery of the channel tube for the forceps channel 27 and the inner peripheral surface of the channel 50 behind the optical window member 23, as compared to a corresponding unreduced thickness D1 shown in FIG. 19A. Corresponding to the difference between the reduced thickness D3 and the unreduced thickness D1, the distance between the forceps outlet 22 and the optical window member 23 in the end surface of the distal end member 21 can be reduced by D2 (FIG. 19A). Thus, the distal end member 21 of the endoscope system according to the embodiment shown in FIG. 19B can be made to have an outer diameter OA which is smaller than the outer diameter OB of the distal end member 21 in the comparative example shown in FIG. 19A.

There are shown various modified embodiments of the present invention in FIGS. 20 to 23, which are similar to those of FIGS. 11 and 12 in that the endoscope system can be used for an oblique observation.

The endoscope system 139 according to the embodiment shown in FIG. 20 includes an endoscope 140 and a protection cover 141. The protection cover 140 includes a distal end member 21 having an end surface which forms 75* with reference to the center axis of the protection cover 141. The distal end member 21 of the protection cover 141 is formed with a channel 148 into which the endoscope 140 is inserted so that the distal end of the endoscope 140 is brought into contact with the inner surface of the window member 23 (FIG. 21). The distal end region of the endoscope 140 to be inserted into the channel 148 can be made to have a circular cross-section.

The embodiment shown in FIG. 22 includes a distal end member of the -protection cover 141 which is substantially same as that shown in FIG. 20, but is different therefrom in that a channel 149 is provided for a lens holder 143 which serves to retain an oblique observation lens 142. The oblique observation type protection cover 141 can be combined with an ordinary straight observation type endoscope 7 to form an oblique observation type endoscope system 139. The axial positioning of the endoscope 7 and lens holder 143 relative to the distal end member 21 of the protection cover 10 can be readily achieved by opposite end walls on both sides of the channel 149 which function as respective positioning shoulders 126.

Figure 24:
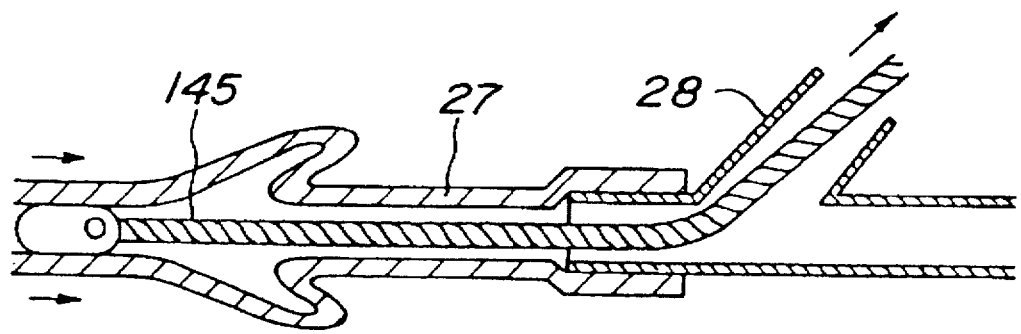
FIG. 24 is an explanatory view showing the mode of axial contraction of the forceps channel tube.

There may be instances during actual use of an endoscope system including an endoscope and a protection cover, wherein a biopsy forceps 145 tends to induce axial contraction of the forceps channel 27 near the branched channel 28 as shown in FIG. 24. This is particularly the case when the biopsy forceps 145 is to be removed from the endoscope through the forceps channel 145 and when the inner surface of the forceps channel 145 has a relatively high frictional resistance. Such a problem can be effectively overcome by the further embodiments of the present invention as shown in FIGS. 25 to 27.

Figure 25:
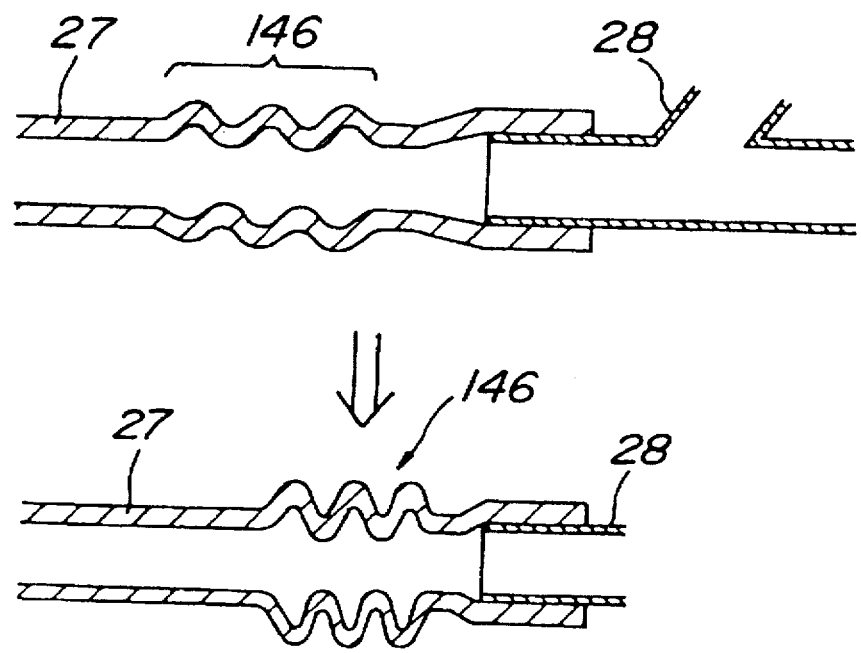
FIGS. 25 to 27 are fragmentary views showing various embodiments of the present invention for minimizing the adverse effects of the axial contraction of the forceps channel tube.

Thus, as shown in FIG. 25, the forceps channel or channel tube 27 is locally provided with a resilient region 146 which is formed preferably of a bellows comprising an appropriate rubbery elastomeric material. The axial contraction of the forceps channel tube 27 can also be mitigated by partly enclosing the forceps channel tube 27 by means of an annular protective sheath, at a location near the branched channel 28. The resilient region 146 has an axial length which is at least 5 cm in order to ensure that the inner diameter of the resilient region 146 in its axially contracted state is maintained at a value which is no smaller than the inner diameter of the forceps channel tube 27 at its remaining region. The forceps channel tube 27 may consist of a material which is the same as that for the resilient region 146, or of a material which is different from that for the resilient region 146. The forceps channel tube 27 may be connected to the branched channel 28 at the region provided with the resilient region 146, or at its proximal end which is free from the resilient region 146.

Figure 26:
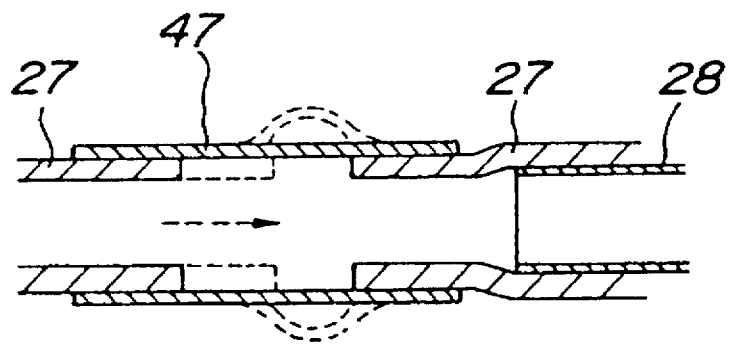

In the embodiment shown in FIG. 26, the forceps channel tube 27 near its proximal end is cut at right angle to the center axis of the tube into two pieces which are bridged by an annular resilient member 147 consisting preferably of an appropriate rubbery elastomeric material.

Figure 27:
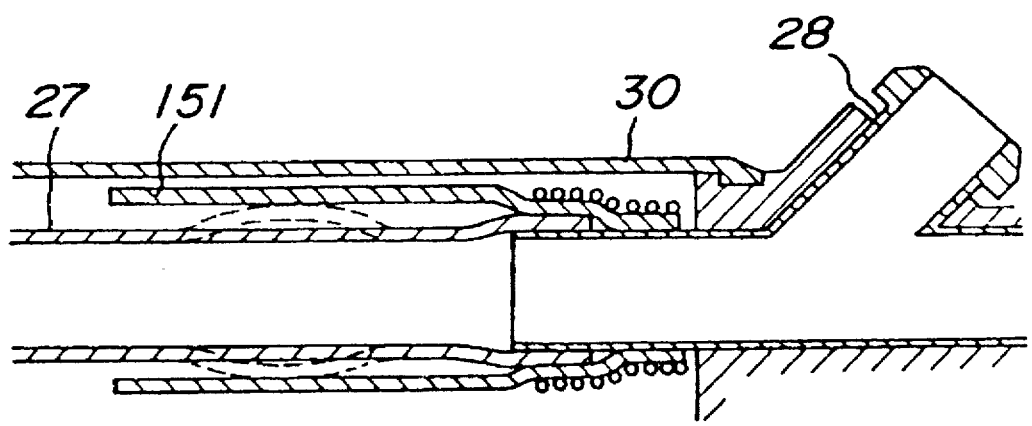

In the embodiment shown in FIG. 27, the forceps channel tube 27 has a proximal end which is connected to the branched channel 28. The forceps channel tube 27 is enclosed by an annular protective sheath 151. The sheath 151 may be formed of plastic or PTFE, and has an axial length which is at least 5 cm. The radial expansion of the forceps channel tube 27 as a result of its axial contraction can be maintained within an acceptable range, as shown by broken line in FIG. 27.

In another embodiment, an elongated strip wound into a roll is used as a cover for covering the universal cord 244 of the endoscope 7 in the aforementioned endoscope system.

Figure 28:
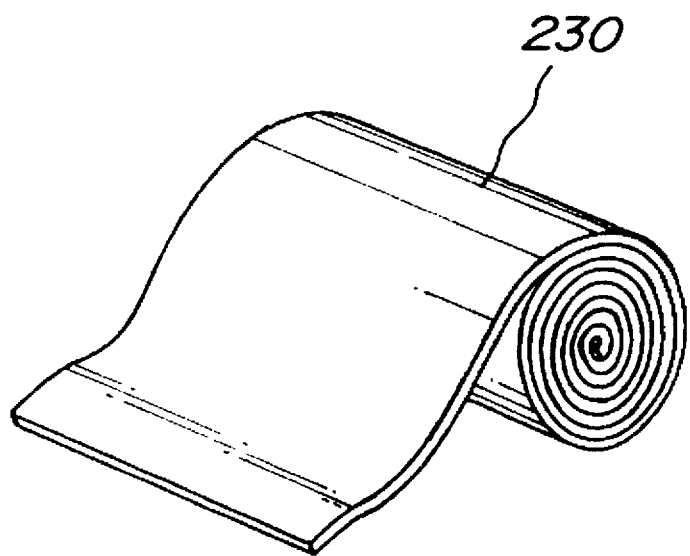
FIG. 28 is a perspective view of an embodiment of the roll-shaped universal cord cover.

FIG. 28 perspectively shows an embodiment of a universal cord cover 230 formed by winding the elongated strip into a roll.

The universal cord cover 230 comprises a strip of a synthetic resin such as polyethylene or the like and a layer of a pressure-sensitive adhesive fixed to a rear surface of the strip. Moreover, the universal cord cover 230 is previously sterilized.

Figure 29:
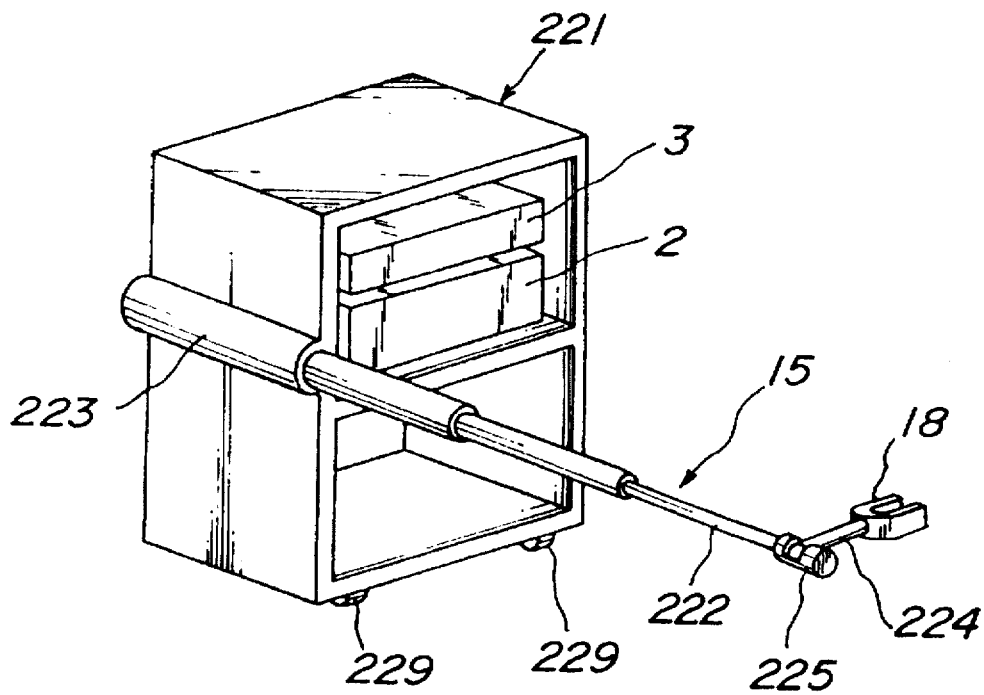
FIG. 29 is a perspective view of an embodiment of a cover holding member suitable for use with the universal cord cover.

There are some preferable means for using such as universal cord cover 230 as shown in FIG. 29 and on. As a fundamental use, the universal cord cover 230 is helically wound around the universal cord by hand.

According to the present invention, the storage, handling and the like of the universal cord cover 230 are easy and folds in the sheet are not formed in the universal cord cover 230, so that the winding operation becomes easy.

Since the elongated strip is wound into a roll in the universal cord cover, the universal cord for the endoscope can properly be covered by helically winding the universal cord cover around the universal cord during use.

Since the wound state of the cover is a roll, it is not required to cut a sheet into a given size and the waste of the cover during use can be eliminated because when the cover is wound around the universal cord at once, it is enough to cut the cover only at the final winding position.

FIG. 1 shows the state of helically winding the universal cord cover 230 around the universal cord 244.

A cover holding member suitable for use with the universal cord cover 230 and a winding method for the universal cord cover will be described with reference to FIGS. 29 to 31.

Figure 30:
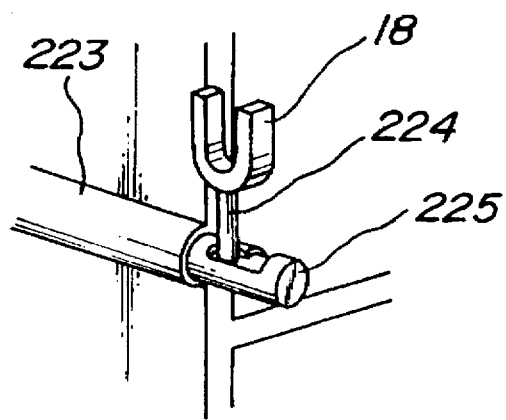
FIG. 30 is a partly schematic view illustrating a non-use state of the cover holding member.

In the embodiment of FIGS. 29 to 31, numeral 221 is a box integrally united with a supporting device. The cart 221 comprises a rod housing member 223. The rod housing member 223 is a cylindrical member disposed on a side surface of the box 221 at a position, for example, corresponding to a level of housing a light source device 2 and is integrally united with the box 221.

A telescopic rod 222 capable of being housed in the rod housing member 223 is a cylindrical rod expandably sliding in the longitudinal direction thereof. The length of the telescopic rod 222 can be changed from a depth of the box 221 (or length of the rod 222) to 4 times of the depth thereof (maximum length) when the rod is pulled out to maximum as shown in FIG. 29.

A supporting arm 224 is disposed on a top side of the telescopic rod 222. This supporting arm 224 connects a U-shaped holder 18 to an arm rotating member 225. In this embodiment, the supporting arm 224 is fixed to the holder 18 and it is possible to pivotally rotate to the arm rotating member 224 within a range of 90° from a horizontal state (FIG. 29) to an upright state (FIG. 30). The arm rotating member 225 is attached to a top end portion of the telescopic rod 222.

In this embodiment, the supporting device 15 is constituted with the above members. Moreover, numeral 229 is a caster.

When the supporting device 15 is not used in the above structure, as shown in FIG. 30, the telescopic rod 222 is contracted in the longitudinal direction and housed in the rod housing member 223, while the arm rotating member 225 protrudes out from the rod housing member 223. In this case, the supporting member 224 is turned in the upright direction and pulled toward the box 221 so as not to rotate in the arm rotating member.

When using the supporting device 15, the telescopic rod 222 is extended to a proper length in the longitudinal direction and the supporting member 224 is turned down in the n horizontal direction.

When the length of the telescopic rod is adjusted to correspond to the length of the universal cord to be covered, it becomes easier to wind the universal cord cover around the universal cord. Particularly, such an effect is conspicuous in the case of using the roll-shaped universal cord cover 230. When the universal cord and channel conduit tubes are surrounded together with the cover, if the universal cord is slacked, it is difficult to surround the cord and tubes together with the cover, but according to the present invention, it is possible to properly cover the universal cord without causing the above problem. That is, the universal cord cover can be helically wound around the universal cord extending from the operation section of the endoscope to the light source device along the expandable telescopic rod 222.

In this case, it is not required to take trouble to preliminarily cut a sheet to a given size. That is, it is sufficient to cut the cover only at the finally wound position and the waste of the cover can be prevented. Also, fold lines or the like are not formed in the cover, so that lowering of winding operation of the cover is not caused as a result of the presence of the fold lines.

FIG. 31 shows the embodiment of using the universal cord cover as mentioned above.

At first, the holder 18 is covered with a cover 20 for the holder and the retainer mount 39 for the protection cover 10 is attached to the holder 18 as shown in FIG. 31 (This operation is carried out at a clean state in order to sufficiently ensure a sterilized state).

Subsequently, the endoscope 7 is inserted into the insertion section cover 11 of the protection cover 10 and the universal cord 244 is extended together with the air supply conduit tube 75, the water supply conduit tube 74 and the suction conduit tube 73 toward the box 221, while the air supply conduit tube 75, the water supply conduit tube 74 and the suction conduit tube 73 are connected to the fluid control device 4 and the universal cord 244 is connected to the light source device 2. Thereafter, the telescopic rod 222 is extended to a level of substantially expanding the universal cord 244, air supply conduit tube 75, water supply conduit tube 74 and suction conduit tube 73 to a maximum (a clean state thereof is not necessarily required). It is understood from FIG. 31 that the universal cord 244 is extended without slacking.

The roll-shaped universal cord cover 230 as shown in FIG. 28 is wound around the universal cord 244, the air supply conduit tube 75, the water supply conduit tube 74 and the suction conduit tube 73, for example, from the operation section side 243 (40) of the universal cord 244 to the connector side 256 as shown in FIG. 31. In this case, the cover is helically wound and the winding operation is easy.

Even if the length of the universal cord from the operation section is different in accordance with the endoscope used, the slacking of the universal cord can be absorbed by adjusting the length of the telescopic rod 222, so that the responsibility is excellent.

Since the pressure-sensitive adhesive layer exists on the rear surface of the universal cord cover 230, the winding can be more simply and surely conducted.

When the operation section cover 12 is mounted onto the operation section 40, the resulting endoscope system 9 can be used at any time (at a clean state).

In the above embodiment, the mounting of the universal cord cover 230 is very easy, while the telescopic rod 222 is expandable and is integrally united with the box 221, which serves to save space.

The universal cord cover 230 of FIG. 28 can be use as it is, and also the box shown in FIGS. 29 to 31b is preferably used thereto.

FIGS. 32 and 33 show another embodiment of using the universal cord cover.

In this embodiment, an arm rotating member 236 for the universal cord cover is movable along the telescopic rod 222 in the longitudinal direction thereof as shown in FIG. 32. Further, an arm 234 for the universal cord cover is rotatably (360° around the rod) attached to the arm rotating member 236, while the other end of the arm 234 is provided with a mounting member 235 for the universal cord cover. A roll core 231 is provided in the center of the wide roll-shaped universal cord cover 230 and is supported by a roll core support 232. The roll core support 232 is provided with a universal cord cover pressure member 233 made from a thin metal plate and having a shape as shown in FIG. 32 and is detachably attached to the universal cord cover mounting member 235.

In this case, a universal cord cover set 257 is comprised of the roll-shaped universal cord cover 230, the roll core 231, roll core support 232 and the universal cord cover pressure member 233.

The method of use of this universal cord cover set is as follows.

When the supporting device 15 is not used, the universal cord cover set 257 inclusive of the roll core support 232 is not attached to the telescopic rod, so that the arm 234 for the universal cord cover and the universal cord cover mounting member 235 are at a state of hanging downward on the rod (see dot-dash lines in FIG. 31).

When the supporting device 15 is used, the procedures before the mounting of the universal cord cover 230 (for example, connection to the fluid control device 4 and light source device 2, adjustment of expansion of the telescopic rod 222 and the like) are the same as in the preceding embodiment, but subsequent procedures are as follows.

In this embodiment, the roll core support 232 of the universal cord cover set 257 is attached to the universal cord cover mounting member 235. The arm 234 for the universal cord cover is rotated to place the universal cord cover 230 on the universal cord 244.

Then, the universal cord cover 230 is drawn out from the cover set to the position of the universal cord cover pressure member 233. Further, portions 223a and 233b located at both sides of the pressure member are pushed downward from the state of FIG. 32 to surround the air supply conduit tube 75, water supply conduit tube 74, suction conduit tube 73 and universal cord 244 with the universal cord cover 230 as shown in FIG. 33. By pulling the universal cord cover pressure member 233 in a direction of the arrow shown in FIG. 33, an end portion 230A of the universal cord cover 230 is first pushed toward the universal cord and then the other end portion 230B is pushed thereon.

This procedure is continued from the operation section side of the endoscope toward the side of the connector 256 (at the clean state).

Even in this embodiment, the same effects as in the aforementioned embodiment are obtained and the winding of the universal cord cover around the universal cord becomes more easy. Furthermore, the storage and handling are convenient and the waste of the universal cord cover can be obviated and also the handling operation becomes easy.

The universal cord cover 230 shown in FIG. 28 is advantageously used not only in the helical winding but also in the efficient winding in the longitudinal direction of the cover as shown in FIGS. 32 and 33. The latter case is preferable for the supporting device integrally united with the box in the embodiment of FIGS. 32 and 33.

Moreover, when the universal cord of the endoscope to be mounted to the supporting device 15 is extended to approximately the maximum extent by the expandable telescopic rod and then surrounded with the universal cord cover 230, if the universal cord cover set 257 is used for the winding of the universal cord cover, the cover set 257 is attached onto the top end side of the rod and pulled toward the connector side to wind the cover around the cord.

FIGS. 34 and 35 show another embodiment of using the universal cord cover.

As shown in FIG. 34, the telescopic rod 222 can slidably be extended in the longitudinal direction and is rotatably attached to the box 221 through an arm rotating member 226. The arm rotating member 226 is disposed on the side face of the box 221 at a position slightly higher than a position of a rack 221a of the box and a protrusion, as a stand stopper 227, is arranged on the side face of the box 221 upward from the arm rotating member 226 and therebehind.

A stand rock 228 is arranged on the front side face of the stand stopper 227 for fixing the telescopic rod 222. As shown in FIG. 35, the stand rock 228 is opened outward as shown by an arrow by pushing a pressure portion 228a of the stand rock in a direction of an arrow (solid line state) and turned inward by releasing the opened state (dot-dash line state).

In this embodiment, the holder 18 is rotatably attached to the holder arm 224, while the holder arm 224 is rotatably attached to the arm rotating member 225. When the holder 18 is rotated by 90° to the holder arm 224, or when the holder arm 224 is rotated by 180° to the arm rotating member 225, the holder and the arm are rocked.

According to the above structure, when the supporting device 15 is not used, the arm rotating member 225 is stood upright (at a shortest sliding state) to rock the telescopic rod 222 through the stand rock 228 (solid line state in FIG. 34). In this case, it is preferable that the holder arm 224 is turned inward to the box 221 without obstruction (opposite direction to the state shown in FIG. 34).

Moreover, as shown in FIG. 34, when the holder arm 224 is placed outward in the direction of the side face of the stand stopper 227 and the holder is rendered into the lateral direction, the holder 18 can be used as a scope hanger.

On the other hand, when the supporting device 15 is used, the telescopic rod 222 is taken out from the stand rock 228 and falls down in a horizontal direction while supporting the rod 222 (dot-dash line state in FIG. 34). In this case, a lower portion of the rod 222 located below the arm rotating member 226 contacts with the lower face of the stand stopper 227, whereby the rod 222 is fixed at a horizontal state.

The horizontally fixed telescopic rod 222 is adjusted to the same preferred length as in the aforementioned embodiments as shown by an arrow at the dot-dash line state of the rod 222 in FIG. 34 and the holder arm 224 is rotated forward to the box 221 and the holder 18 is rotated laterally.

According to the embodiment of FIG. 34, the same effects as in the above embodiments are obtained, and further the supporting device 15 can be used as a scope hanger, so that the utility thereof becomes greater.

Furthermore, the telescopic rod 222 is a falling type, so that when the rod is stood upright as shown in FIG. 34, space is not taken during storage and hence the slidable telescopic rod 222 may be made from a material having a fairly long length and consequently it has a sufficient strength and the cost is low. That is, the length of each segment constituting the slidable rod 222 can be set to a longer length and hence the sliding number of the rod 222 required for obtaining the given maximum length as an expandable rod may be reduced.

The universal cord cover 230 shown in FIG. 28 can advantageously be applied to the case shown in FIGS. 34 and 35.

A preferable embodiment as a cover 20 for the holder will be described with reference to FIGS. 36 to 39.

In an endoscope, it is preferable to prevent contamination by attaching the holder cover to the holder before use. However, when the attachment of the holder cover is conducted every medical experiment and/or treatment, the preparation and the like are troublesome.

The structure for solving this problem is a lamination cover system as mentioned below.

FIG. 36 diagrammatically shows the lamination state of the covers, in which the holder cover 20 is a laminated cover body covering the holder 18. Plural covers, for example, 10 covers are laminated on the holder 18. That is, the holder covers 20 are previously attached on the holder 18 at a laminated state (which is supplied to a user as it is), in which each cover material is, for example, made from vinyl or polyethylene sheet.

As shown in a left-hand portion of FIG. 36, the U-shaped holder 18 is provided at its end portion with a holder mounting member 237 integrally united therewith. As shown in FIG. 36, a peeling away thread 238 is arranged outside the holder 18 through a connecting portion between the holder 18 and the holder mounting member 237 and the end portion of the thread 238 is arranged as a gripping portion 238 at a position corresponding to the side face of the holder 18. They form a cover tearing portion.

Also, the laminated holder covers 20 are previously sterilized. In this embodiment, the holder 18 itself can be disposable.

For example, the holder 18 provided with the holder covers 20 can be used as follows.

In the case of the aforementioned box, the holder cover 20 is attached to the holder 18 (see FIGS. 29, 31 and 34), laminated covers can be used instead of a single holder cover, in which the disposable holder 18 provided with the holder covers 20 may be attached to the holder arm 224 through the holder mounting member 237. The subsequent procedures are the same as in the aforementioned embodiments.

After every use of the endoscope system 9 for a medical experiment and/or treatment, the gripping portion 239 is pulled to tear the holder cover 20 in the vicinity of the holder mounting member 237 through the peeling away thread 238 and then the top end portion of the holder cover 20 is removed out with hand. Thus, only the outermost holder cover 20 is removed out as shown in a right-hand portion of FIG. 36.

In this way, a new sterilized holder cover 20 is successively appears, so that the cover 20 can be used a clean holder 18 until all of the laminated holder covers 20 are removed so as to expose the surface of the holder 18 itself. When the surface of the holder 18 itself is previously sterilized, such a holder itself can finally be used.

According to this embodiment, once the laminated holder covers 20 are attached onto the holder 18, it is not required to exchange the holder cover with a new one after every medical experiment and/or treatment. Therefore, the exchanging operation is avoided, which takes a long time, and the operability is efficiently improved. If the holder covers 20 are used at a laminated state corresponding to the cover number required for daily planned medical experiments and/or treatments, the operation becomes more convenient and the holder can be used during the day without exchange and hence the labor between the medical experiments and/or treatments can be omitted to save time.

Further, the structure of the holder 18 is simple, so that even if the holder 18 is disposable, the cost becomes less.

The above structure can be applied to the case shown in FIG. 1.

FIGS. 38 and 39 another embodiment corresponding to the case of FIGS. 36 and 37. In this case, a laminated cover body is used as the holder cover 20 covering the holder 18, in which the attaching surface (U-shaped inner surface) of the holder cover 20 to the holder mounting member 39 is treated with a pressure-sensitive adhesive 241 so as not to stick to the holder cover 20.

As shown in FIGS. 38 and 39, the root portion 20a of the holder cover 20 is provided with a cover tearing member 240 consisting of a tearing top portion 240a and a base body 240b. The base body 240b of the cover tearing member 240 is connected to the holder mounting member 237 and acts as a spring to push the tearing top portion 240a toward the holder mounting member 237.

On the other hand, a top end of the tearing top portion 240a is sharply formed so as to break only a sheet in the holder cover 20.

In this embodiment, when the retainer mount 39 located on the side of the insertion section cover of the protection cover 10 is mounted onto the holder 18, the holder cover 20 is stuck to the retainer mount 39 through the pressure-sensitive adhesive 241. When the protection cover 10 is removed from the holder 18, the uppermost holder cover 20 moves together with the retainer mount 39, so that the root portion 20a of the holder cover is broken by the tearing top portion 240a to open in the vicinity of the holder mounting member 237. Therefore, when the protection cover 10 is successively separated away from the holder 18, only the uppermost sheet of the holder cover 20 is removed out together as shown in a right-hand portion of FIG. 39.

Thus, the removed one sheet of the holder cover 20 as shown in the right-hand portion of FIG. 39 is disposed by removing it from the protection cover 10 or together with the used disposable cover protection 10.

According to this embodiment, the same effects as in the aforementioned embodiments are obtained and also the operation becomes more easy because it is not required to remove the holder cover 20 from the holder 18.

A preferable embodiment of an operation section cover 12 will be described with reference to FIGS. 40 and 41.

A sheet-like cover for covering the operation section of the endoscope system is used to cover the circumference of the operation section. When the operation section is covered with one cover sheet, if such a cover sheet is removed according to the same procedure as in the attaching procedure, the end portion of the cover sheet is first found out and then the cover sheet is removed out starting from this end portion. If the end portion is hardly found out, the removing operation of the operation section cover is troublesome and hence the removal takes a long time and becomes trouble.

For this end, each embodiments of FIGS. 40 and 41 provides an operation section cover 12 of a sheet capable of easily conducting the removal.

In addition, these embodiments realize the provision of a operation section cover 12 which mitigates the labor for detaching it after every medical experiment and/or treatment and facilitates the attachment and detachment operation.

In the embodiment of FIG. 40, a hole for an angle knob shaft is formed in a sheet-like operation section cover and perforation for the separation of the cover is formed so as to pass through the hole.

The operation section cover 12 is made, for example, from a vinyl sheet. FIG. 40 is a developed view of the cover viewed from a surface covering the operation section 40 of the endoscope 7 (which is a rear surface the attached state). A pressure-sensitive adhesive layer 254 is formed on an upper and right-side end portion of the surface covering the operation section 40 along these end portions as shown in FIG. 40.

Furthermore, a notch portion 251 for the universal cord 244 and a hole 252 for the angle knob shaft are formed in the operation section cover, respectively, as shown in FIG. 40. In this embodiment, simply broken perforation 253 is formed in the cover so as to pass through a center of the hole 252 in parallel with the right-side end or to arrive to the right-side end in a direction perpendicular to the perforation. Moreover, holes 255 for air supply switch 248, water supply switch 248 and electric switches 250 are formed in the vicinity of the center of the cover 12 for the operation section.

In the embodiment of FIG. 40, the operation section cover 12 of the above structure is provided by laminating plural sheets, for example, 10 sheets one upon the other. That is, the operation section cover 12 is a laminated sheet body, which can be supplied to a user in a previously sterilized state. Moreover, numeral 246 is a cover mounting member.

In the attachment of the operation section cover 20 to the operation section 40, the universal cord 244 of the operation sec.-ion 40 and the holes 252 and 255 are mutually positioned to the notch portion 251 for the universal cord, the angle knob shaft 245, the air supply switch 248, the water supply switch 249 and the electric switches 250 and then the surface provided with the pressure-sensitive adhesive layer 254 is folded toward the operation section 40 to cover the operation section 40.

On the other hand, when the cover is detached after use, the cover is broken along the simply broken perforation 253 to remove out only the upper sheet of the operation section cover 12.

Once the operation section cover 12 is attached to the operation section, the medical experiment and/or treatment may be conducted in accordance with the number of the sheets constituting the cover.

According to this embodiment, it is possible to simply remove the cover sheet without carefully handling it during the attachment, so that time can be saved.

Further, it is not required to detach the operation section cover after every medical experiment and/or treatment because this cover is a laminated cover body and the attach and detach operation of the operation section cover becomes more easy.

In the embodiment of FIG. 41, a peeling away thread 238 is arranged instead of the perforation 235. Moreover, FIG. 41 is a developed view of the operation section cover viewed from a surface corresponding to the front surface at the attached state, opposite to the case of FIG. 40.

That is, the peeling away thread 238 is used for the separation of the cover, so that the gripping portion 239 is arranged in the top of the thread 238. As shown in FIG. 41, the thread 238 is preferably arranged so as to contact with the periphery of the hole 252 for the angle knob shaft.

Even in this embodiment, the same effects as in the aforementioned embodiments are obtained. After use, the gripping portion 239 is pulled to break the cover sheet through the peeling away thread 238, whereby only the uppermost cover sheet can be removed and a newly sterilized sheet of the operation section cover 12 successively appears.

The operation section cover 12 of the above structure can be applied alone or together with the aforementioned universal cord cover 230 to the operation section of the endoscope shown in FIG. 1.

Figure 42A:
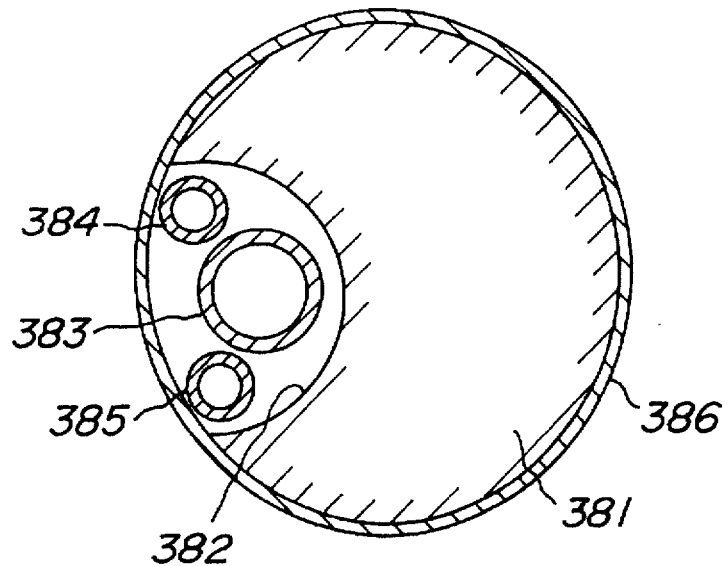
FIGS. 42A and 42B are cross sectional views showing a known endoscope system including an endoscope and a protection cover.

FIG. 42A shows a known combination of an endoscope and a protection cover. Along an outer surface of an insertion section 381 of the endoscope there is formed a recess 382, and suction tube 383, air supply tube 384 and water supply tube 385 are provided in the recess, so that when the insertion section 381 is inserted into a protection cover 386, a cross section of an assembly become circular as illustrated in FIG. 42. Therefore, an outer appearance becomes compact and the endoscopic inspection may be applied widely.

Figure 43A:
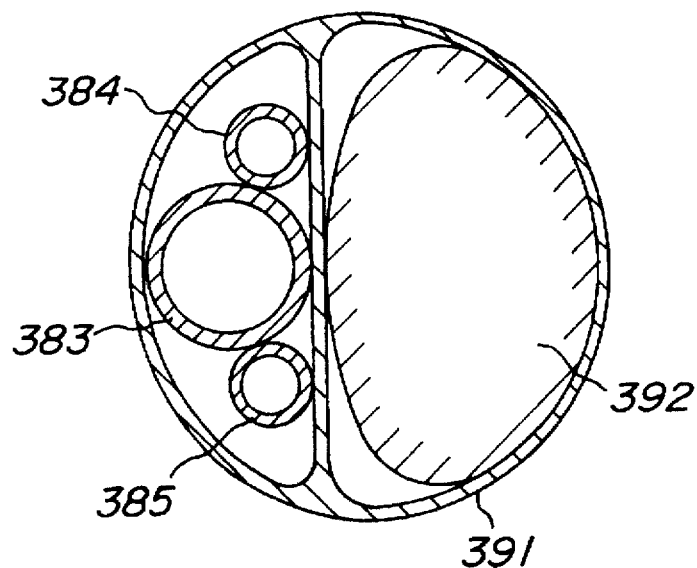
FIGS. 43A and 43B are cross sectional views showing another known endoscope system including an endoscope and a protection cover.

FIG. 43A illustrates another known combination of endoscope and protection cover. In this case, a protection cover 391 is composed of a double lumen tube having a first lumen into which an insertion section of an endoscope is inserted and a second lumen into which suction tube 383, air supply tube 384 and water supply tube 385 are inserted. Also in this known assembly, a cross section is substantially circular.

However, the insertion sections 381 and 391 do not have a circular cross section, so that they have an anisotropy for a bending motion. That is to say, the insertion section is easily bent in one direction, but is not easily bent in another direction. Particularly, when the insertion section inserted into the protection cover is twisted about its longitudinal axis, the distal end of the assembly could not be turned in a smooth manner upon turning the proximal end thereof and there might be produced repelling force at the distal end portion.

Therefore, the distal end of the assembly could not be moved in accordance with the operation of an operator, and particularly it is impossible to move the distal end precisely or finely. This results in that a time required for inspection would be prolonged and a patient might be subjected to pain, and moreover a load for the operator might be increased.

Figure 42B:
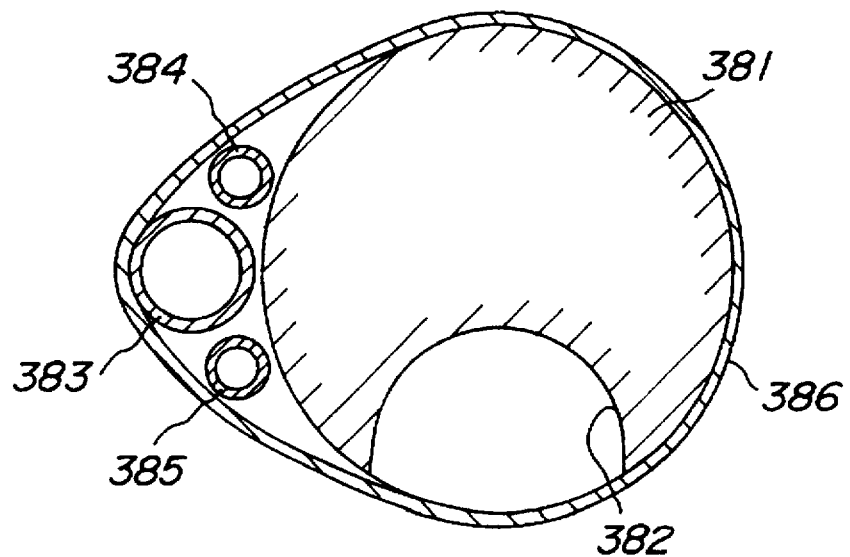
Figure 43B:
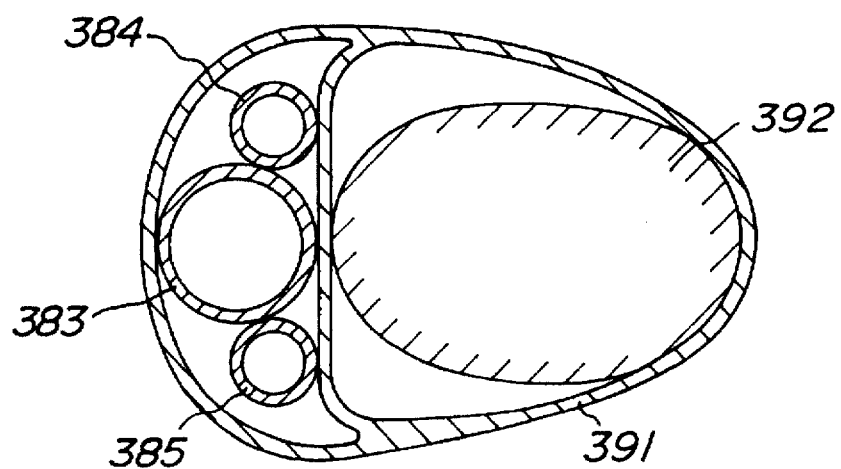

Further, there is not provided any stopping member for a relative rotation between the insertion section 381 or 391 and the cover 381 or 391, and thus when the insertion section is twisted, the insertion section is rotated within the cover as shown in FIGS. 42B and 43B. Then, a maximum diameter of the assembly is increased and the insertion of the assembly is very deteriorated.

The present invention provides a novel endoscope which can mitigate the above mentioned drawbacks of the known endoscopes shown in FIGS. 42 and 43.

Figure 44:
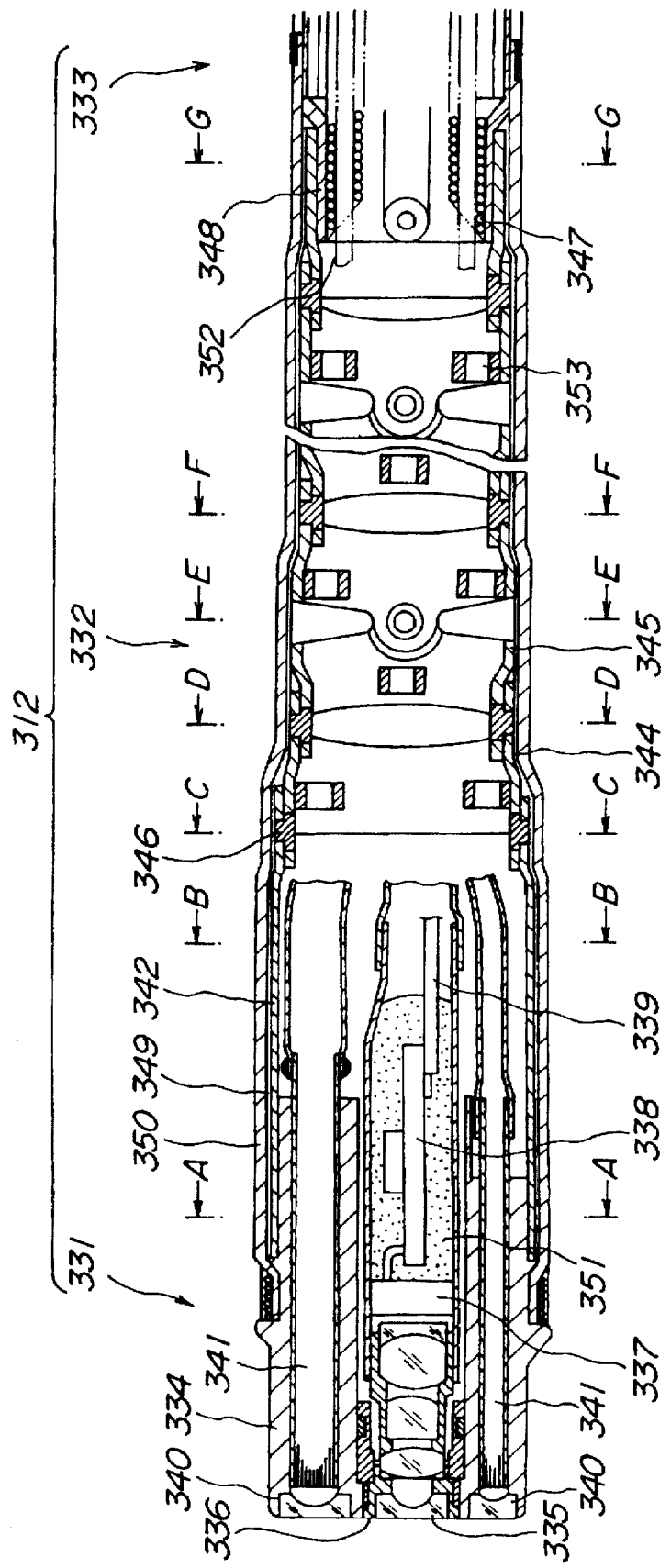
FIG. 44 is a longitudinal cross sectional view illustrating a distal end portion of another embodiment of the endoscope according to the invention.

FIG. 44 is a longitudinal cross sectional view of an insertion section of an endoscope according to the invention and FIGS. 45A to 45G are lateral cross sectional views cut along lines A—A to G—G in FIG. 44.

As shown in FIG. 44, the endoscope comprises an insertion section 312 including distal end portion 331, bendable portion 332 and flexible portion 333. As illustrated in FIG. 45A, a distal end construction member 334 of the insertion section 312 has a substantially semi-circular outer configuration. Within an observation window formed in the distal end construction member 334 along its longitudinal axis, an objective lens 335 is arranged by means of a lens holder 336, and a CCD 337 is provided at a focal plane of the objective lens. To a rear surface of CCD 337 there is connected one terminal of a print circuit member 338 whose other terminal is connected to a signal wire 339.

There are further provided illumination windows above and below the observation window and illumination lenses 340 are secured to respective illumination windows, and light guide optical fibers 341 are provided. To a rear end of the distal end construction member 344 is fixed a first bending frame 342 by means of screws as shown in FIG. 45A.

A shape of a proximal end portion of the first bending frame 342 may be changed, because the flexible signal wire 339 having a small cross section is existent within said proximal end portion. To the proximal end of the first bending frame 342 is rotatably secured by rivets 346 a series of second bending frame 344, third bending frame 345 and so on, and a final bending frame 347 is couple with a distal end mouthpiece body 348 of the flexible portion 333.

As depicted in FIG. 45C, a cross section of a distal end portion of the second bending frame 344 is flat and is similar to that of the first bending frame shown in FIGS. 45A and 45B. However, a cross section of a proximal end portion of the second bending frame 344 has a substantially circular as illustrated in FIG. 45D. A distal end portion of the third bending frame 345 has a cross section shown in FIG. 45D and a proximal end portion of this frame has a circular cross section as depicted in FIG. 45E. Therefore, an outer configuration of the bendable portion 332 and flexible portion 333 becomes also circular. This means that an outer configuration of a substantial part of the bendable portion 332 and an outer configuration of the flexible portion 333 are circular. The second to final bending frames 344 to 347 are covered with a mesh tube 349 made by metal wire or yarn and an outer sheath 350 made of resilient material such as elastomer. The print circuit member 338 is embedded in a fitting member 351 and is arranged such that a direction of a thickness extends in a major axis of the distal end construction member 334 as best shown in FIG. 45A. Then, a dimension of the print circuit member 338 viewed in the major axis of the distal end construction member 334 is small, and thus the light guide fiber bundles 341 can be arranged above and below the print circuit member 334 without increasing a diameter of the member 334 in the direction of the major axis. In this manner, an oblateness or ellipticity of the outer configuration of the distal end construction member 334 can be small and a substantially semicircular cross section can be smoothly converted into a circular cross section. This is manifest when the light guide is composed of a plurality of optical fiber bundles.

Bending operation wires 352 are passed through wire guides 353 fixed to an inner wall of the bendable portion 332 and distal ends of the wires are fixed to the first bending frame 342 or distal end construction member 334.

Figure 46A:
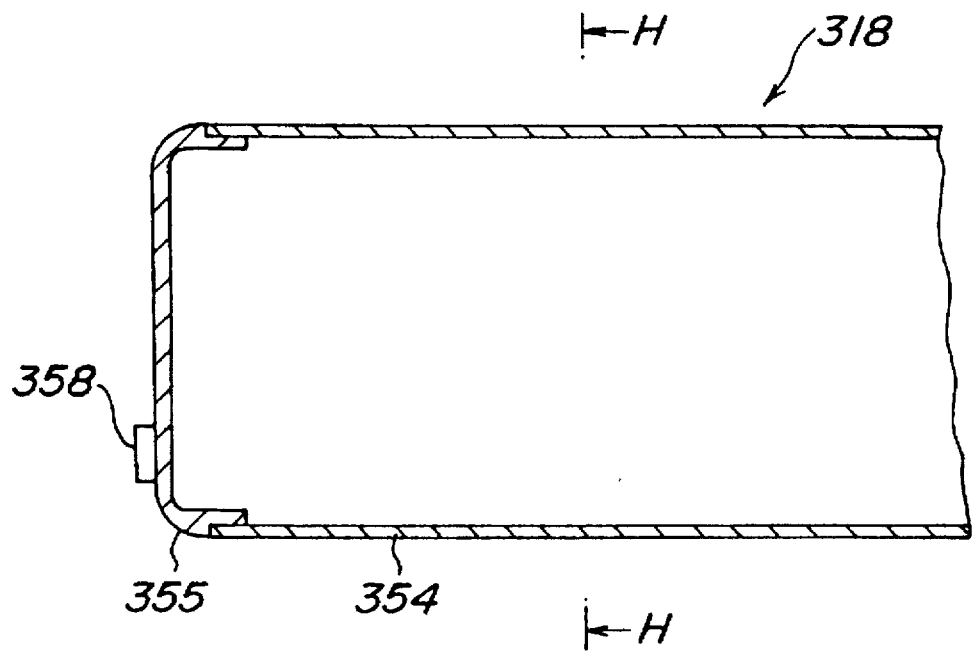
FIG. 46A is a longitudinal cross sectional view depicting a distal end portion of the protection cover according to the invention.
Figure 46B:
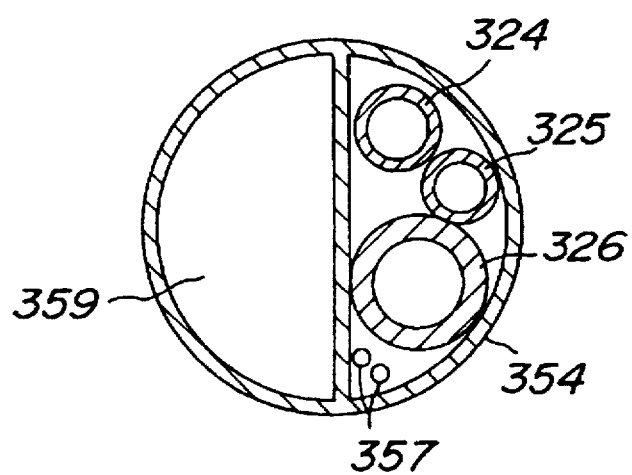
FIG. 46B is a lateral cross sectional view cut along a line H—H in FIG. 46A.

FIGS. 46A is a longitudinal cross sectional view showing a distal end portion of a protection cover 318 into which the insertion section 312 of endoscope is to be inserted and FIG. 46B is a lateral cross sectional view cut along a line H—H in FIG. 46A. The protection cover 318 comprises a double lumen tube 354 having two semicircular lumens, and a front end cover 355 secured to a distal end of the double lumen tube 354. The front cover 355 has formed therein transparent windows at positions corresponding to the objective lens 335 and illumination lenses 340.

The double lumen tube 354 is made of resilient material such as urethane resin and vinyl chloride resin and has a thickness of about 0.1 to 0.4 mm. Within one of the semicircular double lumens there are accommodated al-r supply tube 234, water supply tube 325, suction tube 326 and signal wires 357. The signal wires 357 are connected to a pressure sensor 358 provided on an outer surface of the front cover 355.

These air supply tube 234, water supply tube 325 and suction tube 326 are exposed out of the front cover 355 and openings of the air supply tube 324 and water supply tube 325 are directed in parallel with the surface of the front cover 355 so that the surface can be effectively cleaned or washed.

It should be noted that the pressure sensor 358 may be replaced by PH sensor, concentration sensor, temperature sensor, reaction sensor which reacts to a special substance or magnetic sensor. Any one of them may be selected in accordance with an object of inspection. The pressure sensor 358 may be detachably fixed to the protection cover 318.

The other semicircular lumen of the double lumen tube 354 serves as a insertion section inserting channel 359 into which the insertion section 312 of the endoscope is inserted.

FIG. 47 shows a condition in which the insertion section 312 of the endoscope including the distal end portion 331, bendable portion 332 and flexible portion 333 has been inserted into the insertion section inserting channel 359 of the protection cover 318. As shown in FIG. 46B, the insertion section inserting channel 359 is formed by the substantially semicircular lumen of the double lumen tube 354.

The double lumen tube 356 is made by a thick resilient membrane, so that when the distal end portion 331, bendable portion 332 and flexible portion 333 are inserted into the tube, an outer configuration of these portions is gradually changed from a substantially semicircular cross section into a circular cross section. Therefore, an outer configuration of a combination of the insertion section of endoscope and the protection cover changes also gradually, and thus they can be smoothly and easily inserted into a cavity under observation. It should be noted that a cross section of an outer configuration of the distal end portion 331 is also substantially circular. Moreover, an outer configuration of the bendable portion 332 is changed into a circle from a middle thereof, and therefore the anisotropy of the bending can be mitigated as compared with the known endoscope in which an outer configuration of the bendable portion is non-circular.

As explained above, the insertion section has a circular cross section, and thus the insertion section can be equally bent in any direction, and a twisting force applied to the proximal end of the insertion section can be smoothly transferred to the distal end, so that the inserting operation of the insertion section into a cavity can be improved.

The distal end of the insertion section is formed as a non-circular cross section, but when the insertion section is inserted into the protection cover, the distal end of the assembly has a substantially circular cross section. Therefore, a diameter of the distal end can be minimized, and this also contributes to the improvement in the faculty of inserting operation. Furthermore, an outer configuration of the assembly which is inserted into the cavity is changed smoothly, and therefore the smooth insertion can be performed.

The second and third bending frames 344 and 346 may be formed by pressing a circular pipe or may be formed by metal injection or metal molding. In the present embodiment, an inner configuration of the insertion section inserting channel 359 has the same shape along its whole length, but according to the invention, it may be deformed in accordance with an outer configuration of the bendable portion 332 and flexible portion 333.

It should be noted that there may be formed depressions and protrusions or parallel recesses in the inner wall of the insertion section inserting channel 359 so that a friction between the insertion section and the channel is increased. Then, the protection cover is twisted together with the insertion section when a twisting force is applied to the proximal end of the insertion section. Then, the inconvenience shown in FIGS. 42B and 43D can be avoided.

Figure 48:
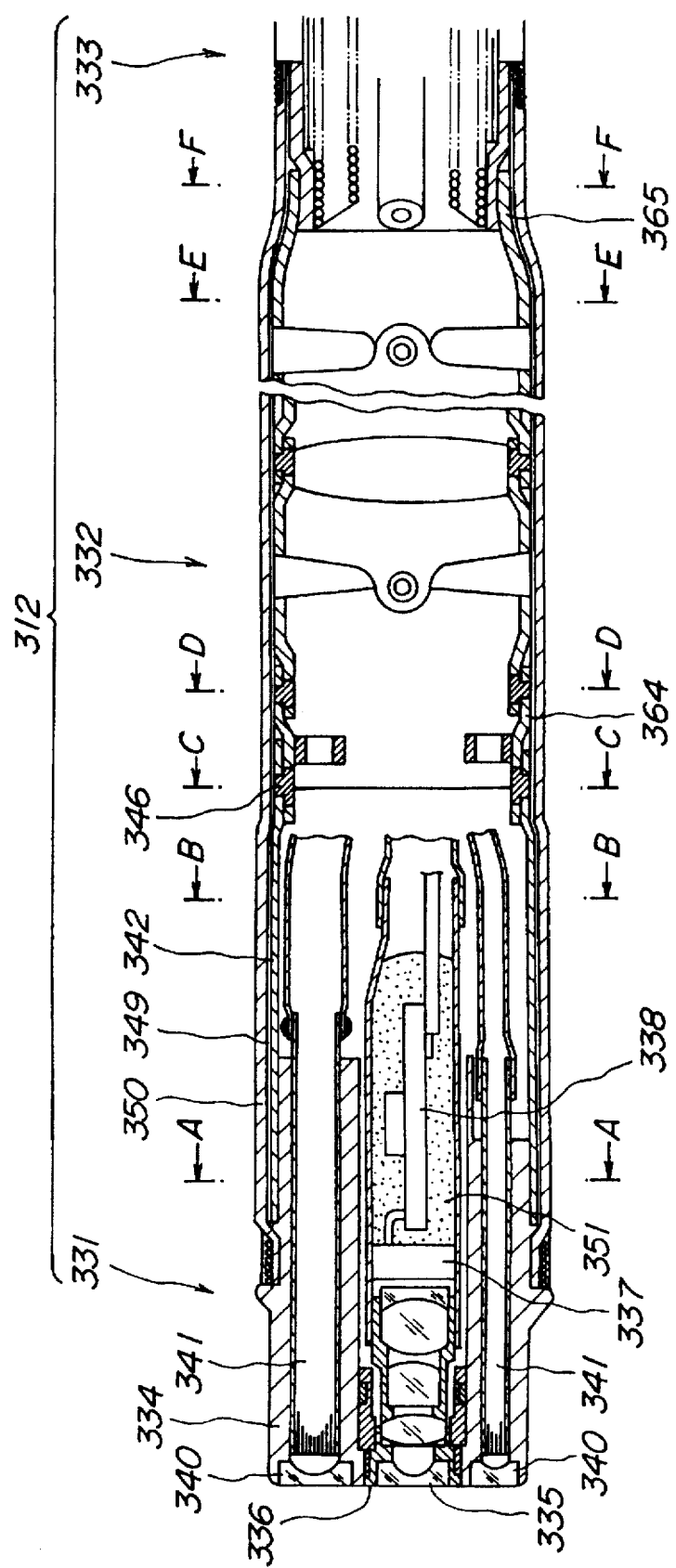
FIG. 48 is a longitudinal cross sectional view illustrating a distal end portion of another embodiment of the endoscope according to the invention.
Figure 49:
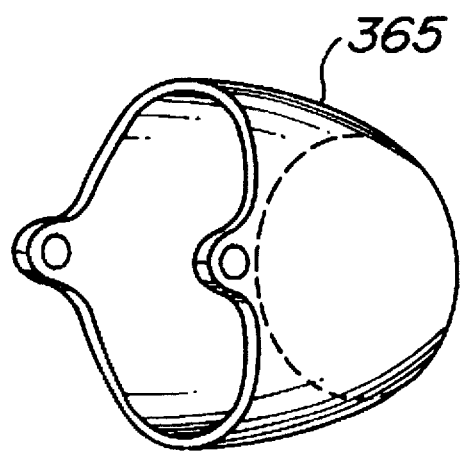
FIG. 49 is perspective view illustrating a last bending frame.
Figure 50E:
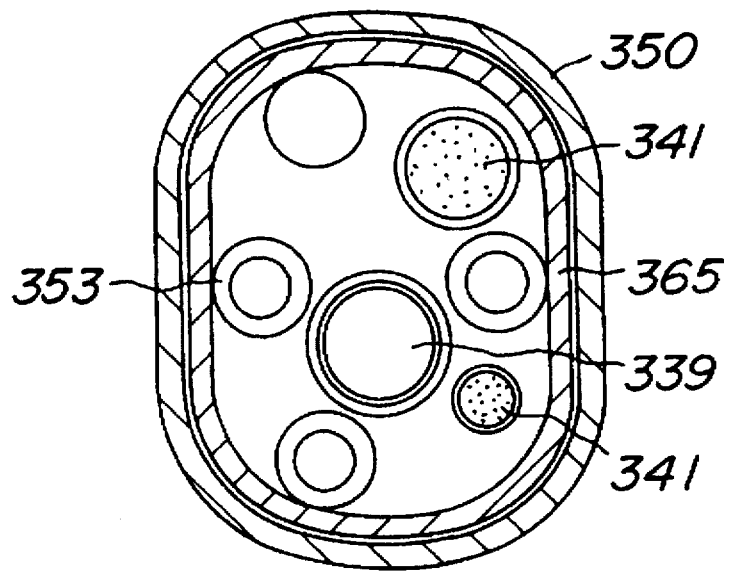
Figure 50F:
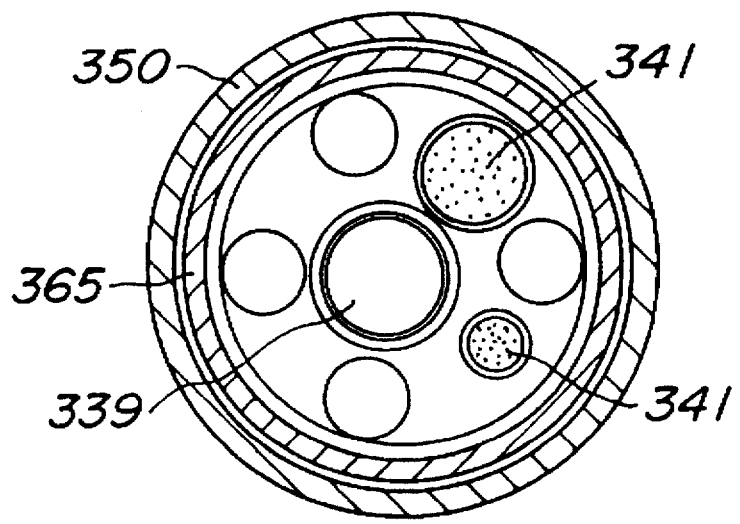

FIG. 48 is a longitudinal cross sectional view showing the insertion section 312 of another embodiment of the endoscope according to the invention and FIGS. 50A to 50F are lateral cross sectional views cut along lines A—A to F—F in FIG. 48. In the embodiment shown in FIGS. 44 to 47, a substantially semicircular cross section of the insertion section 312 is changed into a substantially circular cross section at a region near the distal end of the bendable portion 332, but in the present embodiment, this change in a cross section is performed at a region near the proximal end of the bendable portion 332. As illustrated in FIGS. 50C and 50D, a second bending frame 364 coupled with a first bending frame 342 by means of rivets 346 has a flat cross section similar to that of the first bending frame. This flat cross section continues up to a last bending frame 365. FIG. 49 is a perspective view showing the last bending frame 365. A proximal end of this bending frame 365 has a circular cross section and a distal end has an oblong or oval cross section. That is, a cross section of the final bending frame 365 is changed from an oval shape into a circular shape as best shown in FIGS. 50E and 50F. The remaining construction of the present embodiment is similar to the previous embodiment illustrated in FIGS. 44 to 47.

In the present embodiment, the bendable portion 332 has a substantially oval cross section and when the insertion section is inserted into the insertion section inserting channel 359 of the protection cover 318, a cross section of the assembly at a region near the bendable portion 332 becomes substantially circular. Therefore, a diameter near the bendable portion 332 can be made small. The outer sheath 350 of the bendable portion 332 should have an extremely high expansive capability and is preferably made of elastomer which has a poor slipping capability. Therefore, if the bendable portion 332 having a poor slipping capability has a circular cross section and a large diameter, the insertion section 312 of the endoscope could not be easily or smoothly inserted into the insertion section inserting channel 359 of the protection cover 318. In the present embodiment, the bendable portion 332 has a small diameter and has a cross section which is similar to that of the insertion section inserting channel 359 in a free condition, so that the inserting operation can be performed easily.

It should be noted that an oval cross section may be changed into a circular cross section in a region of the first bending frame 342 instead of the final bending frame 365. In this case, an outer configuration of connecting portions of the first and last bending frames 342 and 365 becomes large, so that an outer configuration of the first bending frame 342 near its connecting portion is oval to reduce a diameter and an outer configuration of a proximal end thereof is circular.

FIGS. 51 and 52 are lateral cross sectional views illustrating another embodiment of the insertion section of the endoscope according to the invention. In the present embodiment, a cross section of the insertion section is gradually changed from an oval shape into a circular shape over a whole length of the bendable portion, i.e. from a distal end to a proximal end thereof.

FIG. 51 is a cross section at the distal end of the bendable portion. An outer configuration of a first bending frame 366 has a substantially semicircular cross section. The mesh tube 349 and outer sheath 350 have also a semicircular cross section similar to that of the first bending frame 366. To the first bending frame 366 are soldered distal ends of wires 352a to 352d for bending the bendable portion 332 up and down as well as right and left. It should be noted that the wires 352a and 352b serve to bend the bendable portion at a large angle so that a large pulling force is applied, and thus a diameter of these wires is larger than that of the wires 352c and 352d. The wires 352a and 352b may be made of material having a higher strength such as tungsten.

The printed circuit board 338 arranged within the first bending frame 366 is oriented such that a direction of a thickness of the printed board extends in a minor axis of the first bending frame. Therefore, a length of the minor axis can be reduced as compared with the case in which the printed circuit board is arranged such that the direction of its thickness extends in a major axis. Then, a diameter of the assembly of the insertion section and protection cover can be minimized and the inserting operation can be carried out easily and smoothly without causing pain for patients. This advantage is manifest when the optical fiber light guide is formed by a single fiber bundle.

FIG. 52 is a cross section at the proximal end of the bendable portion. The last bending frame 368 has a circular cross section. In the present embodiment, bending frames between the first and last frames 366 and 368 have cross sections which are gradually changed from a substantially semicircular cross section to a substantially circular cross section. Signal wires 339 connected to CCD 337 are divided into first and second groups 369a and 369b. Signal wires of respective groups are provided in soft tubes made of silicon or expanded PTFE.

In a region of the double lumen tube 354 which extends from the bendable portion to the proximal end of the insertion section has a partition 370 which separates the flexible portion 333 of the insertion section and the air supply tube 324, water supply tube 325 and suction tube 326. The partition 370 may be thermally fused to an inner wall of the double lumen tube 354 or they may be integrally formed as a single unit.

It should be noted that the partition 370 is provided in a region from the bendable portion to the distal end of the insertion section. The partition 370 is provided for forming a sufficient space within the insertion section inserting channel 359 so that the insertion section can be easily inserted into the channel. If the partition 370 is not provided, the air supply tube 324, water supply tube 325 and suction tube 326 might protrude into the insertion section inserting channel 359.

The distal ends of the air supply tube 324, water supply tube 325 and suction tube 326 are fixed to the distal end construction member 334 at the distal end of the bendable portion and are separated by the partition 370 at the proximal end of the bendable portion. The bendable portion 332 has a length of about 50 to 150 mm, so that the arrangement of the tubes 324, 325 and 326 is not disturbed in a region of the bendable portion although the partition is not existent in said region, and the operation for inserting the insertion section into the protection cover is not disturbed. Since the partition 370 is not existent is said region of the bendable portion, a diameter of an outer configuration of the bendable portion can be reduced. It should be noted that a cross section of an outer configuration of the distal end of the insertion section is not limited to a semicircular shape, but may be shaped in different configurations such as oval shape, elliptical shape, barrel shape and pin cushion shape or recess may be formed therein.

As explained above, in the embodiments shown in FIGS. 44 to 52, a cross section of the assembly of the insertion section and the protection cover is circular, and thus the insertion section can be bent in any direction under a substantially same flexibility and a twisting force applied to the proximal end of the insertion section can be smoothly transferred to the distal end. In this manner, the insertion section can be easily and smoothly inserted into a cavity under inspection. A cross section of the insertion section is non-circular and when the insertion section is inserted into the protection cover, a cross section of the assembly becomes substantially circular. Therefore, a diameter of the distal end can be made small. This also contributes to the easy and smooth insertion. Moreover, an outer configuration of a portion which is to be inserted into the cavity is gradually changed, and therefore the insertion is not disturbed.

As explained above, the protector cover according to the invention may be used as a disposable cover, and once the endoscopic observation is completed for a patient, the endoscope is removed from the protection cover and the used cover may be discarded. Then a running cost is increased and a large number of used protection covers have to be treated as medical discharges. In order to save a running cost and a treatment of a large amount of medical discharges, the protection cover may be reused. That is, after an endoscopic observation using an endoscope and a protection cover has been completed, the used protection cover is sterilized and washed. In this manner, the protection cover can be reused several times. However, the protection cover is made by a soft and thin film like member, and thus during the inserting and removing operation of the endoscope into and from the protection cover, a hole might be formed in the protection cover. It is apparent that when the protection cover has a hole, the endoscope could not be effectively protected. The present invention provides an apparatus for checking an airtight of a protection cover.

Figure 53:
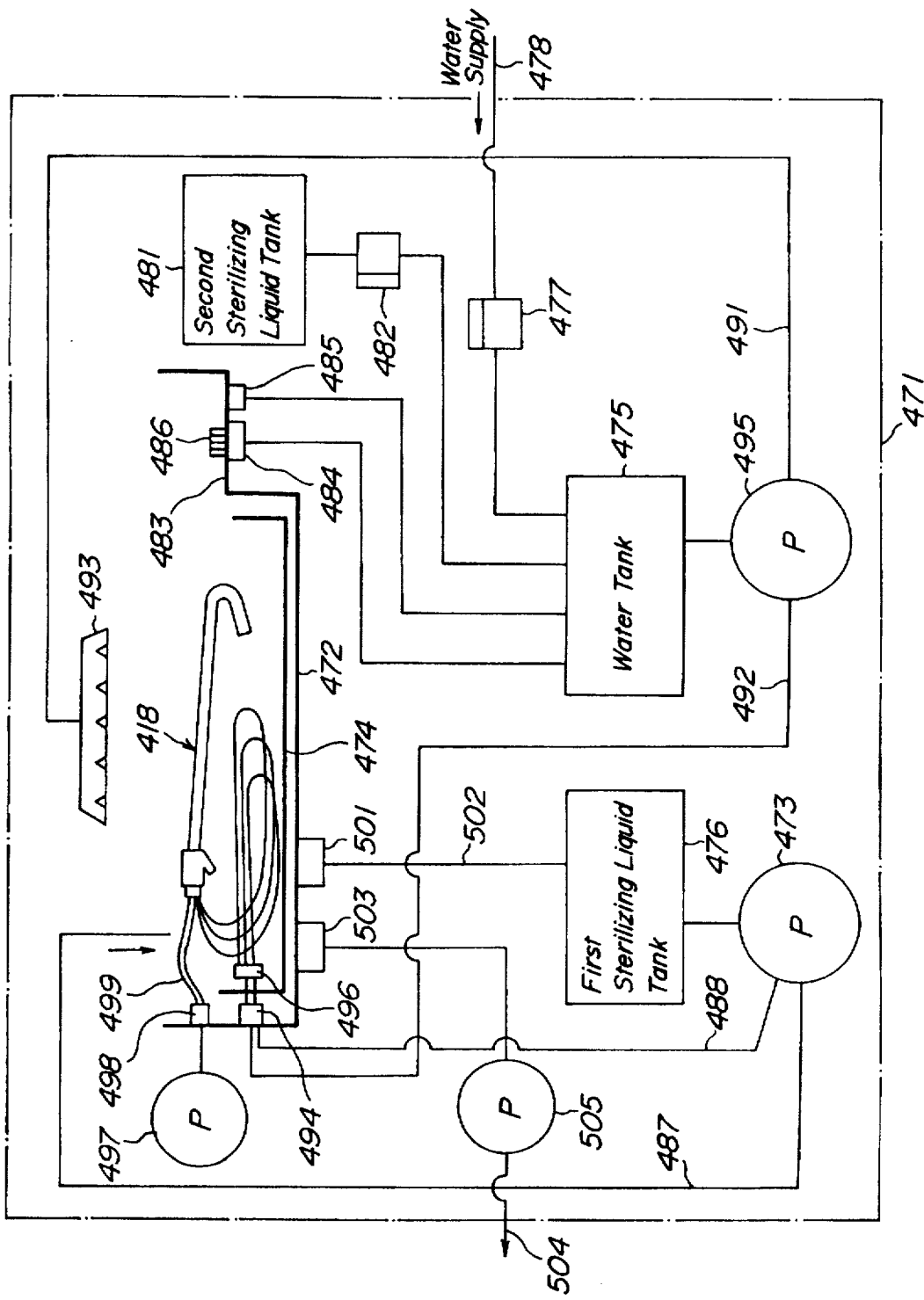
FIG. 53 is a schematic view showing an embodiment of the protection cover cleaning apparatus according to the invention.

FIG. 53 is a schematic view showing a washing and sterilizing apparatus including an embodiment of the airtight checking apparatus according to the invention. The washing and sterilizing apparatus 471 comprises a washing vessel 472 in which a rack 474 is detachably provided, an endoscope cover 418 being placed on said rack. The rack 474 provided in the washing vessel 472 is formed as a metal or plastic mesh or grid. The apparatus 471 further comprises a water tank 475 and a first sterilizing liquid tank 476. To the water tank 475 is coupled a water supply conduit 478 having a valve 477 included therein. This conduit 478 is connected to a tap of a water service not shown. The water tank 475 is further coupled with a second sterilizing liquid tank 481 via an electromagnetic valve 482. A condensed sterilizing liquid is contained in this second sterilizing tank 481.

Within the washing vessel 472 there is provided a platform 483 at a higher level than the rack 474 on which the protection cover 318 is placed. On the platform 483 there are arranged a sterilizing liquid supply inlet 484 and an exhaust outlet 485. Through the inlet 484 a sterilizing liquid is supplied into the water tank 475. Usually the inlet 484 is closed by a first cap 486. Through the exhaust outlet 485 an air is exhausted out of the water tank 475. This outlet 485 may be closed by a second cap not shown. The second cap has a leak opening formed therein and an air is exhausted from the water tank 475. In order to flow a contaminated liquid through the leak opening, a diameter of this opening is as small as possible. It should be noted such an air exhaust system may be provided at respective conduit portions so that liquids can flow smoothly.

To a bottom of the water tank 475 there are coupled washing liquid supply conduits 491 and 492 via a washing pump 495. The conduit 491 is connected to a washing nozzle 493 arranged within the washing vessel 472, and the conduit 492 is connected to a mouthpiece 494 for supplying the washing liquid to channels, said mouthpiece being provided on a side wall of the washing vessel 472. To the mouthpiece 494 is detachably connected a water supply tube 496 whose other end is divided into three conduits which are coupled with the suction tube, air supply tube and water supply tube, respectively. In FIG. 53 only the suction tube 426 is illustrated. It should be noted that the water supply tube 496 may be connected to a forceps inlet 427 or a washing water may be supplied from both the suction tube 426 and forceps inlet 427. In these case, a forceps plug 469 made of resilient material is removed from the forceps inlet 427.

To a bottom of the first sterilizing liquid tank 476 are coupled two sterilizing liquid supply conduits 487 and 488 via a pump 473. The conduit 487 is communicated with the washing vessel 472 and the conduit 488 is coupled with the mouthpiece 494 in parallel with the washing liquid supply conduit 492. On the side wall of the washing vessel 472 there is luther provided a compressed air supply methodic 498 which is communicated with an air pump 497. To the mouthpiece 498 is detachably connected a inflating tube 499.

Figure 54:
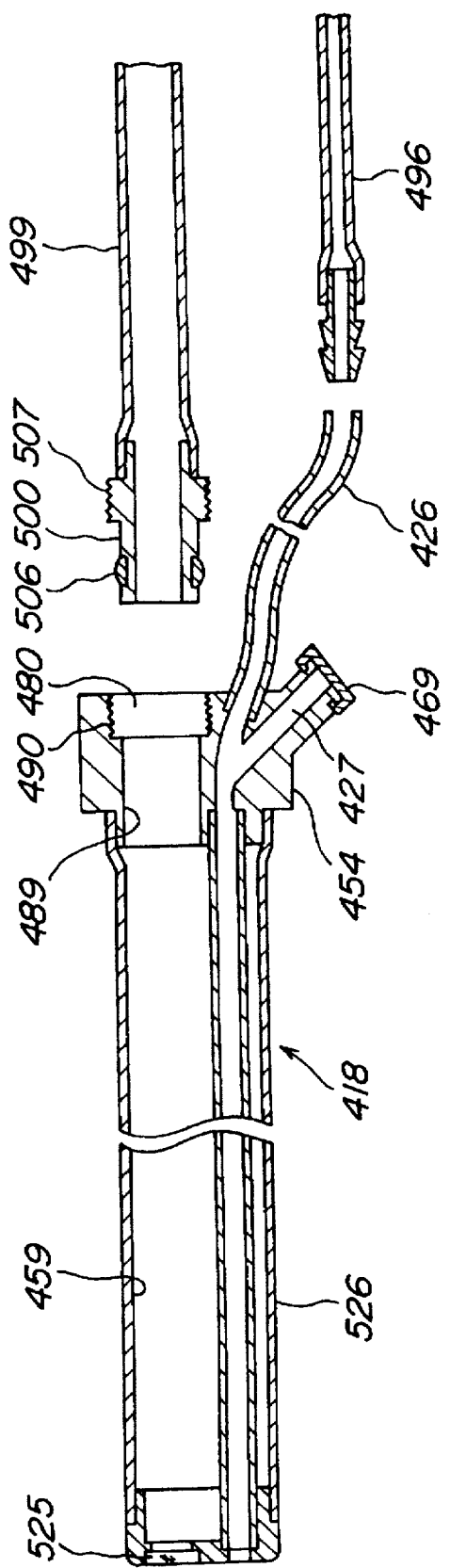
FIG. 54 is a longitudinal cross sectional view illustrating the connection of an inflating tube to an insertion section inserting channel of the protection cover.

As illustrated in FIG. 54, the inflating tube 499 has a mouthpiece 500 at its one end and this mouthpiece is detachably secured to an opening 480 of an insertion section inserting channel 459 into which an insertion section of an endoscope. At the opening 480 of a proximal end member or connecting member 454 of the protection cover 418 there are formed a cylindrical sealing surface 489 and a female screw surface 490. The mouthpiece 500 of the inflating tube 499 there are provided an O-ring 506 which engages with the sealing surface 489 in an airtight manner and a male screw 507 which engages with the female screw surface.

As depicted in FIG. 53, on the bottom of the washing vessel 472, sterilizing liquid recovering mouthpiece and discharging mouthpiece. To the recovering mouthpiece is coupled a sterilizing liquid recovering conduit 502 via an electromagnetic valve 101 and the other end of the recovering conduit is connected to an upper portion of the first sterilizing liquid tank 476. The sterilizing liquid discharging mouthpiece is coupled with a discharge conduit 504 via an electromagnetic valve 501, and a discharge Dump 505 is provided in the discharge conduit.

As shown in FIG. 55, the air pump 497 for inflating the insertion section inserting channel is coupled with the mouthpiece 498 by means of a conduit 515 which is communicated with a flow meter 516. An output signal of the flow meter 516 is supplied to a control unit 517 and is processed therein to detect a condition of the protection tube 418, and a result of judgment is displayed by a display unit 518.

FIG. 56 is a flow chart showing successive steps for checking the airtight capability of a washed protection tube and for washing and sterilizing a used protection tube. In a step S1, the mouthpiece portion 500 of the inflating tube 499 is inserted into the opening 480 of the insertion section inserting channel 459 of a used protection tube 418 and the male screw 507 of the mouthpiece portion 507 is engaged with the female screw 490 of the opening 480. In this manner, the inflating tube 499 is communicated with the insertion section inserting channel 459 in an airtight manner. Then, in a step S2, a leak detection switch (not shown) provided on the washing apparatus 471 is made ON to energize the air pump 497 to inflate the insertion section inserting channel 459 of the protection tube 418 (step S3). This condition is maintained for a predetermined time period as shown by a step S4. After this period, the output signal of the flow meter 516 is monitored in a step S5. When no hole is formed in the protection cover 418, there is no air flow so that flow data supplied from the flow meter 516 is zero, but if a hole is formed in the insertion section inserting channel 459, an air flow is detected and the flow data is not zero. Therefore, in a step S6, the flow data is checked to be zero or not. When it is judged that the flow data is not zero in the step S6, the control unit 517 supplies an alarm signal to the display unit 518 and an alarm is displayed in a step S7b, and the checking operation is stopped in a step S8.

When the flow data is judged to be not larger than zero in the step S6, then a washing and sterilizing operation is performed continuously. At first, in a step S11, the pump 495 is eneraized to supply the washing water to the washing nozzle 493 as well as the insertion section inserting channel 459 and an outer surface of the protection tube 418 and an inner wall of the inserting channel 459 are washed. During this operation, the electromagnetic valve 503 is opened and a wasted washing water is discharged by means of the pump 505 (step S12). It should be noted that the water supply valve 477 is opened and a water is supplied to the water tank 475. After washing the protection cover 418, a sterilizing is performed. In the sterilizing process, at first the pump 473 is energized (step S13) so that the sterilizing liquid contained in the first sterilizing liquid tank 476 is supplied to the washing vessel 472 as well as to the suction tube 426, air supply tube and water supply tube. The electromagnetic valves 501 and 503 are closed, so that the sterilizing liquid is contained in the washing vessel 472 to such a level that the protection cover 418 is immersed therein. Then, the supply of the sterilizing liquid is stopped and the protection tube 418 is maintained to be erased in the sterilizing liquid for a predetermined time period (step S14). After that, the electromagnet valve 501 is opened so that the sterilizing liquid in the washing vessel 472 is recovered into the first sterilizing liquid tank 476 under the gravitational force.

Then, a rinsing process (steps 15 and 16) is carried out. This process is similar to the above explained washing process and the sterilizing liquid applied on the protection cover 418 is washed away. After that, the washing water is removed and the protection cover is dried.

Next, the leak checking process is conducted again in steps S5 to SB to confirm that the washed protection cover does not have a hole or aperture. When no leak is detected, a normal LED lamp is lit on.

In the present embodiment, at a beginning of every day routine work, the washing apparatus itself may be washed and sterilized in order to remove various bacteria increased within the apparatus. When a start button not shown is pushed, a water remained within the apparatus is discharged. That is, the valve 477 and electromagnetic valve 503 are opened and the pumps 495 and 505 are energized for predetermined time. Then, a fresh water is supplied to the water tank 475 by means of the conduit 478 and then is further supplied from the water tank 475 to the washing vessel 472 via the conduits 491 and 492. A wasted water is discharged from the apparatus via the conduit 504. In this manner, an old water remained within the apparatus can be replaced by a fresh water. After that, the pumps are driven while the valve 477 is closed to empty the water tank 475.

Next, there is provided a time period D for checking whether or not a fresh sterilizing liquid is supplied from the inlet 484 to the water tank 475. That is to say, in a usual routine work, a user removes the cap 486 and supplies a fresh sterilizing liquid. When supply of a fresh sterilizing liquid is detected during the time period D, a sterilizing process is performed. However, if the supply of a fresh sterilizing liquid is not detected during the time period D, the electromagnetic valve 482 is opened and a condensed sterilizing liquid is supplied from the second sterilizing liquid 1-tank 481 to the water tank 475. At the same time, the valve 477 is opened and a fresh water is supplied into the water tank 475, so that the condensed sterilizing liquid is diluted to a desired concentration.

Then, the pump 495 is energized again to supply the sterilizing liquid in the water tank 475 to the washing vessel 472 and various conduits, while the valve 477 is closed. In this case, the sterilizing liquid is supplied for ten seconds and then a rest time of sixty seconds is provided in order to keep the sterilizing liquid and walls to be contacted with each other for a long time period. This process is repeated until the water tank 475 becomes empty. Then, the valve 477 is opened to rinse the water tank 475 and water supply conduits.

Within the second sterilizing tank 481, there may be contained a cheap sterilizing liquid such as amphoteric soap, reversed soap and chlorine type sterilizing liquid. As long as infecting bacteria which could be hardly killed by a sterilizing agent is not existent in a water, the apparatus can be kept clean when the apparatus is washed and sterilized every morning. If the apparatus is contaminated with infecting bacteria, it is necessary to use a strong glutaldehyde sterilizing agent. Such a sterilizing agent may be supplied from the inlet 484, in order to attain a smooth liquid flow, there is provided an air exit in each of the conduits. By supplying a sterilizing liquid into the conduits via such air exits, they may be easily and effectively sterilized. The air exhaust outlet 485 for the water tank 475 is formed as a very small opening in order to prevent contaminated substances from being discharged therefrom. However, when the cap is removed, there is existent a large opening, so that the sterilizing liquid can be easily supplied.

A leakage of the protection tube may be detected by immersing the cover in the water and detecting bubbles. In this case, the insertion section inserting channel 359 is inflated and the valves 501 and 503 are closed. The pump 495 is driven until the protection cover is immersed in the water. At the same time, an air is supplied to the suction tube 426, water supply tube and air supply tube and air bubbles adhered to walls of these tubes are washed away. Therefore, a leakage of the protection cover can be performed accurately without being affected by air bubbles adhered to these tubes.

After the water is supplied into the washing vessel 475 up to a desired level, the pump 495 is stopped. Then a user can visually watch a generation of bubbles due to a leakage of the protection cover. That is to say, since the air pump 497 is still driven, air bubbles are generated from a hole formed in the protection cover.

It should be noted that the inflating tube 499 and the insertion section inserting channel 459 may be coupled in an airtight manner by means of an one-touch connector such as snap fit.

In the cleaning apparatus according to the invention, the protection cover is washed while it is inflated, so that the protection cover can be cleaned fully. Since the opening 480 of the insertion section inserting channel 459 is closed during the washing operation, the inner wall of the channel can be effectively prevented from being wetted. When the inside of the channel 459 is wet, the objective lens of the endoscope and/or the inner wall of the observation window of the protection cover might be clouded. Moreover, a leak of a used protection cover is first checked prior to the washing, and thus a waste washing can be saved. Further, when a protection cover is judged to have a hole, an endoscope which has been used together with this protection cover can be immediately cleaned. In this case, when no hole is detected by the first checking but a hole is detected by the second checking, it is not necessary to clean the endoscope.

In a distal end face of the protection cover, there is provided an observation window and the objective lens and optical fibers of the illuminating light guide are brought into contact with an inner surface of the observation window. In this construction, a part of illuminating light emitted from the optical fiber bundles is reflected by the inner surface of the observation window and then the thus reflected light is further reflected by an outer surface of the distal end of the insertion section of the endoscope. In this manner, the illumination light is repeatedly reflected between the inner wall of the observation window of the protection cover and the outer wall of the distal end of the insertion section of the endoscope. The thus reflected light is made incident upon the objective lens, and this results in a flare ghost in a displayed endoscopic image.

In Japanese Patent Application Laid-open Publication Kokai Hei 3-264037, a light shielding member is provided on the outer surface of the distal end of the insertion section between the objective system and the illuminating system. However, in this construction, the light shielding member is urged against the inner wall of the observation window provided at the distal end of the protection cover when the insertion section is inserted into the protection cover. Then, the observation is liable to be damaged and in an extreme case, the observation window might be removed from the protection cover. If there is formed a space between the observation window and the protection cover, a water might be introduced into the protection cover through the space.

The present invention provides an endoscope which can mitigate the above mentioned drawback.

Figure 57A:
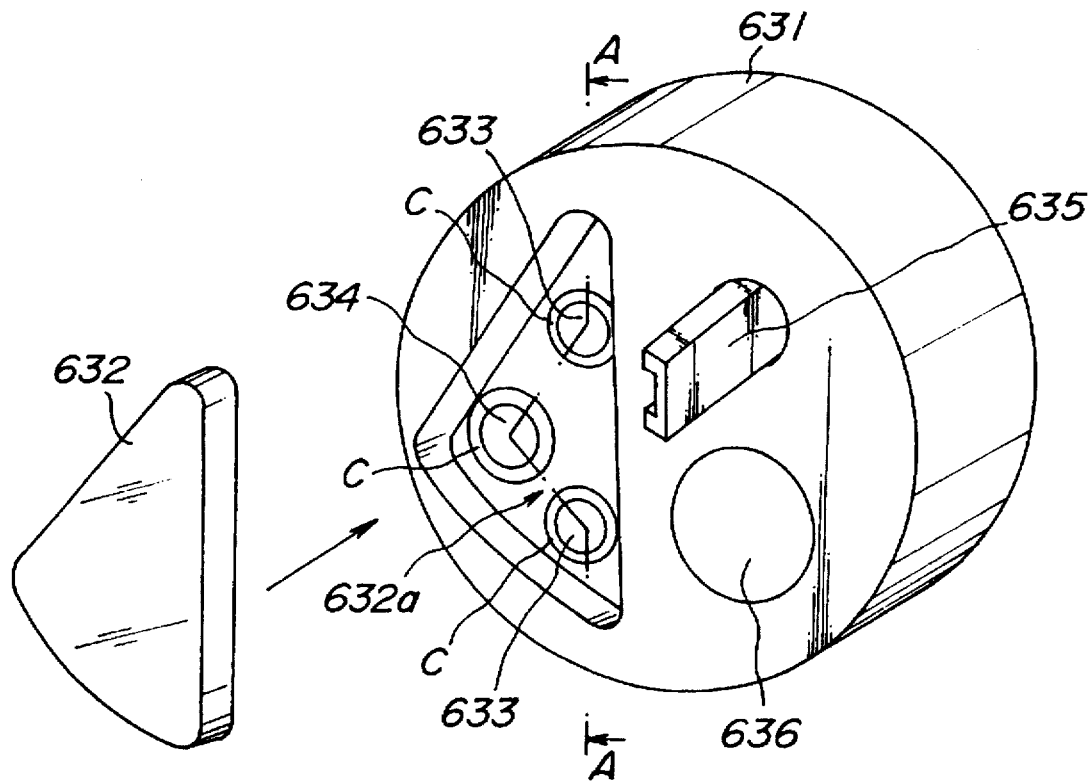
FIG. 57A and 57B are perspective and cross sectional views, respectively showing a distal end portion of another embodiment of the protection tube according to the invention.
Figure 57B:
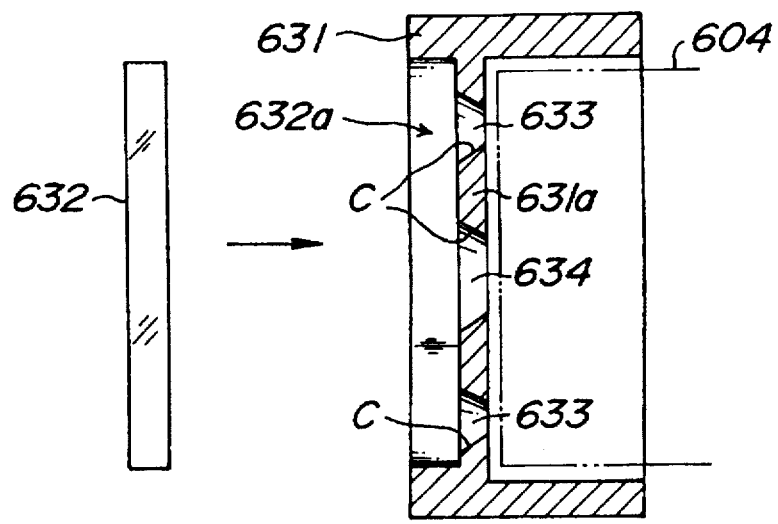

FIG. 57A is a partially exploded perspective view showing the endoscope according to the invention, and FIG. 57B is a cross section cut along a line A—A in FIG. 57A. A distal end member 631 of the protection cover is made of a hard and opaque plastics such as altered PPT and hard vinyl chloride resin. In the distal end member 631 there are formed through holes 633 for illuminating optical system and through hole 634 for observation optical system. These holes 633 and 634 are tapered such that a diameter increased outwardly. A tapered surface of a hole is denoted by c. In an outer surface of the distal end member 631 there is formed a substantially triangular recess 632a, and a lens cover 632 having a triangular shape identical with the recess 632a. The lens cover 632 is formed by a plane parallel plate, which is made of transparent plastics such as acrylic resin and polycarbonate resin and has a thickness of 0.2 to 0.7 Tnm. A smaller diameter of each of the holes 633 is determined to be slightly larger than a diameter of the optical fiber bundle of the light guide and similarly a smaller diameter of the hole 634 is slightly larger than a diameter of the objective lens. A reference numeral 635 denotes an air and water supply nozzle and a reference numeral 636 represents an opening of a forceps channel.

When the insertion section of the endoscope is inserted into the protection tube, a distal end construction member 604 of the insertion section is inserted into the distal end member 631 of the protection cover such that an outer surface of the distal end construction member 604 is brought into contact with an inner surface 631a of the distal end member 631 of the protection cover. Therefore, the distal end construction member 604 is not brought into contact with the lens cover 632.

Illumination light emitted from the light guide optical fiber bundles is transmitted through the holes 633 and lens cover 632 and is projected onto an object under inspection and light reflected by the object is made incident upon the objective lens through the lens cover 632 and hole 634. In the present embodiment, since the outer surface of the distal end construction member 604 of the insertion section of the endoscope is not brought into contact with the inner wall of the lens cover 632, and therefore the lens cover can be effectively prevented from being damaged and removed from the protection cover. Further, tapered holes 633 and 634 are formed in the distal end member 631, so that illumination light reflected by the inner wall of the lens cover 632 could not be made incident upon the objective lens and undesired flare ghost.

Figure 58:
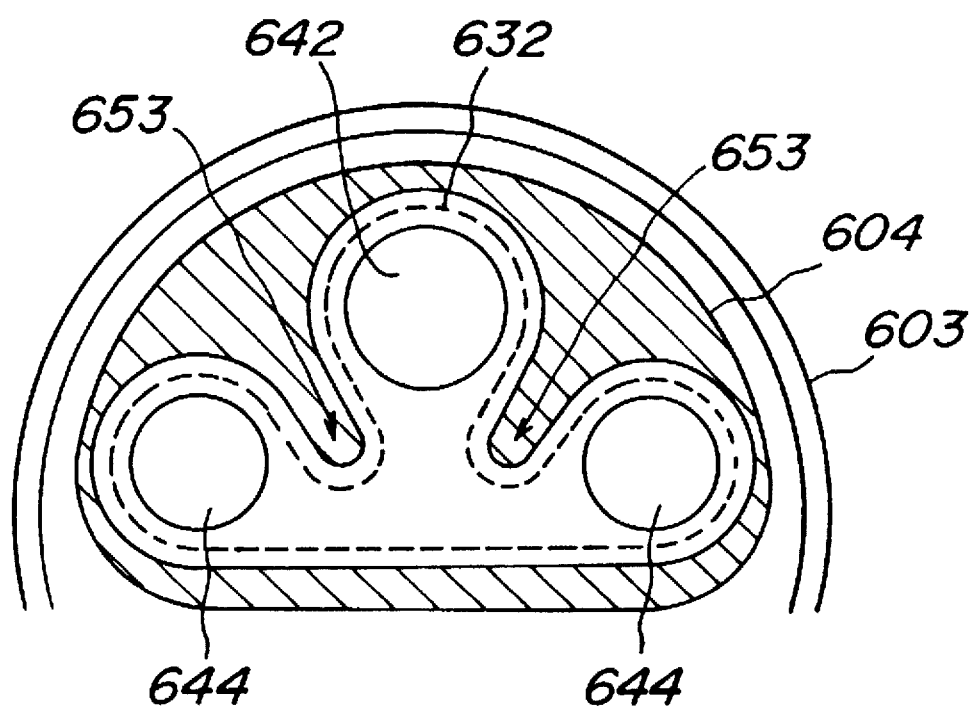
FIG. 58 is a schematic plan view illustrating still another embodiment of the distal end portion of the protection cover according to the invention.

In order to prevent a flare ghost much more positively, the lens cover 632 may be formed to have serration 653 which existent between an objective lens 643 and illuminating optical fiber bundles 644 as illustrated in FIG. 58. In FIG. 58, a hatched portion denotes a contact area between the distal end construction member 604 of the insertion section of the endoscope and the distal end member 631 of the protection tube 603. In this construction, contact areas situating between the objective lens 642 and the illuminating light guide 644 serve as light shielding member and illuminating light is never made incident upon the objective lens.

The present invention is not limited to the specific embodiments as hereinbefore described, and it is understood that the foregoing and other modifications and changes can be made therein without departing from the scope of the invention as defined in the appended claims.

What is claimed is:

1. An endoscope system comprising:
   (a) an endoscope including:
      an inserting section having a proximal end and a distal end and being insertable into a cavity to be inspected, said insertion section comprising a distal end construction member having an objective optical system installed therein, a bendable portion coupled with said distal end construction member and a flexible portion connected to said bendable portion and extending to said proximal end of the insertion section, an outer configuration of said distal end construction member having a non-circular cross-section and an outer configuration of said flexible portion having a substantially circular cross-section, and
      an operation section connected to the proximal end of the insertion section; and
   (b) a protection cover having a proximal end and a digital end and including:
      an insertion section inserting channel into which said insertion section of the endoscope is insertable and which extends from the proximal end to the distal end,
      a distal end member provided at the distal end of said protection cover and including an accommodating portion having a non-circular shape corresponding to said non-circular cross-section of said distal end construction member of the insertion section of said distal end construction member of the insertion section of the endoscope, and
      a conduit channel extending substantially in parallel with said insertion section inserting channel from a proximal end to a distal end, at least one tube being insertable into said conduit channel.

2. An endoscope system according to claim 1, wherein said non-circular cross section of the distal end construction member of said endoscope is formed as a substantially semicircular shape and said conduit channel of said protection cover is formed to have a substantially semicircular cross section.

3. An endoscope system according to claim 2, wherein said protection cover is formed by a double lumen tube having a circular cross section.

4. An endoscope system according to claim 1, wherein said non-circular cross section of the distal end construction member of said endoscope is formed as a substantially oval shape.

5. An endoscope system according to claim 1, wherein an outer configuration of a distal end portion of said bendable portion of said endoscope has said non-circular cross section and an outer configuration of a proximal end of said bendable portion has a circular cross section.

6. An endoscope system according to claim 5, wherein said insertion section of said endoscope comprises an outer sheath made of resilient material.

7. An endoscope system according to claim 1, wherein said distal end member of the protection cover includes a distal end plate member made of opaque material and a transparent optical window member through which light reflected by an object under inspection is made incident upon the objective optical system and an outer surface of said distal end construction member of the insertion section of the endoscope is brought into contact with an inner surface of said distal end member of the protection cover.

8. An endoscope system according to claim 7, wherein a recess is formed in an outer surface of said distal end plate member of said protection cover, said transparent optical window member is clamped into said recess, and at least one opening is formed in said distal end plate member such that said opening is exposed in said recess.

9. An endoscope system according to claim 8, wherein said opening is tapered such that a diameter is increased viewed from inside to outside.

10. An endoscope system according to claim 1, wherein said insertion section inserting channel of said protection cover has an opening at the proximal end, and with said opening is detachably coupled in an airtight manner an inflating tube of a protection cover cleaning apparatus which comprises means for detecting a leakage of an air from the insertion section inserting channel.

11. An endoscope system comprising:

(a) an endoscope including:
an insertion section having a proximal end and a distal end and being insertable into a cavity to be inspected, said insertion section comprising a distal end construction member having an objective optical system installed therein, a bendable portion coupled with said distal end construction member and a flexible portion connected to said bendable portion and extending to said proximal end of the insertion section, an outer configuration of said distal end construction member having a non-circular cross-section and an outer configuration of at least one of said bendable portion and said flexible portion having a substantially circular cross-section, and an operation section connected to the proximal end of the insertion section; and (b) a protection cover having a proximal end and a distal end and including:
an insertion section inserting channel into which said insertion section of the endoscope is insertable and which extends from the proximal end to the distal end, a distal end member provided at the distal end of said protection cover and including an accommodating portion having a non-circular shape corresponding to said non-circular cross-section of said distal end construction member of the insertion section of the endoscope, and a conduit channel extending substantially in parallel with said insertion section inserting channel from a proximal end to a distal end, at least one tube being insertable into said conduit channel.

12. An endoscope system according to claim 11, wherein said distal end of the flexible portion has a non-circular outer configuration.

13. An endoscope system comprising:

(a) an endoscope including:
an insertion section having a proximal end and a distal end and being insertable into a cavity to be inspected, said insertion section comprising a distal end construction member provided on the distal end and having an objective optical system installed therein, an outer configuration of said distal end construction member having a non-circular cross-section and an outer configuration of a remaining portion of the insertion section having a substantially circular cross-section, and an operation section connected to the proximal end of the insertion section; and (b) a protection cover having a proximal end and a distal end and including:
an insertion section inserting channel into which said insertion section of the endoscope is insertable and which extends from the proximal end to the distal end, a distal end member provided at the distal end of said protection cover and including an accommodating portion having a non-circular shape corresponding to said non-circular cross-section of said distal end construction member of the insertion section of the endoscope, and a conduit channel extending substantially in parallel with said insertion section inserting channel from a proximal end to a distal end, at least one tube being insertable into said conduit channel.

* * * * *